United States Patent
Pulman et al.

(10) Patent No.: US 6,333,296 B1
(45) Date of Patent: Dec. 25, 2001

(54) DIARYL ETHERS AND PROCESSES FOR THEIR PREPARATION AND HERBICIDAL AND DESICCANT COMPOSITIONS CONTAINING THEM

(75) Inventors: David A. Pulman; Bai-Ping Ying, both of Mentor, OH (US); Shao-Yong Wu, Fremont, CA (US); Sandeep Gupta, Concord, OH (US); Hiroshi Shimoharada, Shiga (JP); Masamitsu Tsukamoto, Mayfield Heights, OH (US)

(73) Assignee: ISK Americas Incorporated, Concord, OH (US)

( * ) Notice: Subject to any disclaimer, the term of this patent is extended or adjusted under 35 U.S.C. 154(b) by 0 days.

(21) Appl. No.: 09/380,830

(22) PCT Filed: Jan. 14, 1998

(86) PCT No.: PCT/US98/00209

§ 371 Date: Sep. 10, 1999

§ 102(e) Date: Sep. 10, 1999

(87) PCT Pub. No.: WO98/41093

PCT Pub. Date: Sep. 24, 1998

Related U.S. Application Data

(63) Continuation-in-part of application No. 08/947,900, filed on Oct. 9, 1997, now abandoned, and a continuation-in-part of application No. 08/917,682, filed on Aug. 26, 1997, now abandoned, said application No. 08/947,900, is a continuation-in-part of application No. 08/818,061, filed on Mar. 14, 1997, now abandoned.

(51) Int. Cl.$^7$ ................. C07D 239/46; C07D 239/52; A01N 43/54

(52) U.S. Cl. ................. 504/243; 544/295; 544/296; 544/312; 544/314

(58) Field of Search .................. 504/243; 544/295, 544/296, 312, 314

(56) References Cited

U.S. PATENT DOCUMENTS

| | | | |
|---|---|---|---|
| 4,452,981 | 6/1984 | Nagano et al. | 544/236 |
| 4,677,127 | 6/1987 | Boger | 514/346 |
| 4,859,229 | * 8/1989 | Wenger et al. | 71/92 |
| 4,902,337 | 2/1990 | Hirai et al. | 71/92 |
| 4,985,065 | 1/1991 | Theodoridis | 71/92 |

(List continued on next page.)

FOREIGN PATENT DOCUMENTS

| | | |
|---|---|---|
| 2 227 762 | 2/1997 | (CA) . |
| 32 40 975A | 5/1983 | (DE) . |
| 195 27 570A | 1/1997 | (DE) . |
| 196 15 259A | 10/1997 | (DE) . |
| 0 648 722A | 4/1995 | (EP) . |

(List continued on next page.)

OTHER PUBLICATIONS

Chem. abstr., vol. 109, 1988 (Columbus, OH, USA), abstract 109: 73464, Wenger et al. 'Preparation of 3–Phenyluracils as Herbicides.' EP 255047. 1998 (Copy submitted to USPTO by WIPO).
Chem. abstr., vol. 119, 1993 (Columbus, OH, USA), abstract 119: 180805, Kawamura et al. 'Preparation of Pyrimidinedione Derivatives as Herbicides.' JP 05039272. 1993 (Copy submitted to USPTO by WIPO).
Wenger et al. CA 109:73464 (1988).
Kawamura et al. CA 119:180805 (1993).
Watanabe et al. CA 120:191720 (1994).
Moustafa et al. CA 100:61313.
G. Theodoridis "Herbicidal 1–(2,4dihalo–5–phenoxyphenyl)–4–difluoromethyl–4,5–dih.–3–methyl–1,2,4–triazolins(1H)–one derivatives" p. 386, column 1; XP002173953 Chemical Abstracts vol. 122, No. 11, 1995, abstract No. 125877k.

*Primary Examiner*—Mukund J. Shah
*Assistant Examiner*—Deepak R. Rao
(74) *Attorney, Agent, or Firm*—Sughrue, Mion, Zinn, Macpeak & Seas, PLLC

(57) ABSTRACT

Diaryl ether compounds useful in the control of weeds are described. An exemplary compound is represented by the general formula (I):

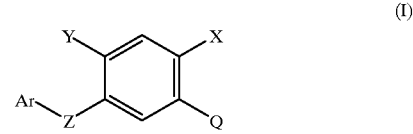

(I)

In this formula Q is represented by $Q_9$:

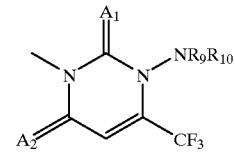

$Q_9$

X and Y represent a hydrogen atom, halogen atom, cyano group, nitro group or $(C_{1-6})$haloalkyl group. $A_1$ and $A_2$ are independently oxygen or sulfur atoms. $R_9$ and $R_{10}$ represent a hydrogen atom, a $(C_{1-6})$alkyl group, an acyl group, or a $(C_{1-6})$alkylsulfonyl group; or $R_9$ and $R_{10}$ may form a ring consisting of polymethylene, $(CH_2)_m$ groups, where m is an integer of 2, 3, 4 or 5, together with the nitrogen atom of $NR_9R_{10}$, which may or may not have a $(C_{1-6})$alkyl substituent. Methods of making the compounds are also described.

20 Claims, No Drawings

U.S. PATENT DOCUMENTS

| | | | |
|---|---|---|---|
| 5,125,958 | 6/1992 | Poss | 71/92 |
| 5,280,010 | 1/1994 | Enomoto et al. | 504/243 |
| 5,281,571 | 1/1994 | Woodard | 504/225 |
| 5,298,502 | 3/1994 | Halling et al. | 514/185 |
| 5,489,571 | 2/1996 | Woodard et al. | 504/280 |
| 5,496,956 | 3/1996 | Woodard et al. | 548/377.1 |

FOREIGN PATENT DOCUMENTS

| | | |
|---|---|---|
| 57-197268 | 12/1982 | (JP) . |
| 5-25173 | 2/1993 | (JP) . |
| 05/39272 * | 2/1993 | (JP) . |
| 5-202031 | 8/1993 | (JP) . |
| 05202031 * | 10/1993 | (JP) . |
| 6-256312 | 9/1994 | (JP) . |
| WO 88 01133A | 2/1988 | (WO) . |
| WO/96/02523 | 2/1996 | (WO) . |
| WO 96/07323 | 3/1996 | (WO) . |
| WO 96/08151 | 3/1996 | (WO) . |
| WO 96/14315 * | 5/1996 | (WO) . |
| WO 96/24590 * | 8/1996 | (WO) . |
| WO 98/27068 | 6/1998 | (WO) . |

* cited by examiner

DIARYL ETHERS AND PROCESSES FOR THEIR PREPARATION AND HERBICIDAL AND DESICCANT COMPOSITIONS CONTAINING THEM

This application is the U.S. national stage application under 37 C.F.R. §371 of International Application No. PCT/US98/00209 filed Jan. 14, 1998 and is a continuation-in-part application of U.S. Ser. No. 08/947,900 filed Oct. 9, 1997, now abandoned, which is a continuation-in-part of U.S. Ser. No. 08/818,061 filed Mar. 14, 1997 now abandoned; and also is a continuation-in-part of U.S. Ser. No. 08/917,682, filed Aug. 26, 1997, now abandoned.

TECHNICAL FIELD

A class of diaryl ethers and compositions thereof which are useful in the control of weeds is of the general formula

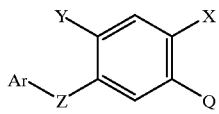

(I)

wherein

X, Y are hydrogen, halogen, cyano, nitro, or $(C_{1-6})$ haloalkyl;

Z is oxygen or sulfur;

Q is selected from

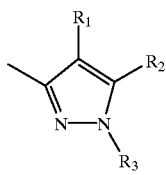

$Q_1$

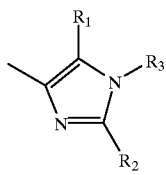

$Q_2$

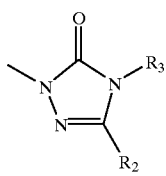

$Q_3$

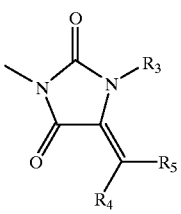

$Q_4$

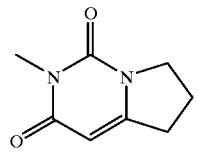

$Q_5$

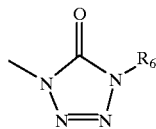

$Q_6$

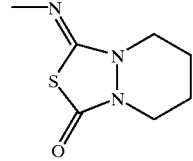

$Q_7$

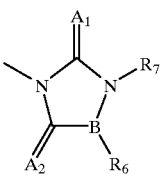

$Q_8$

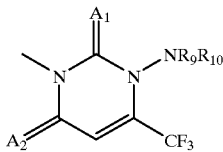

$Q_9$

Ar is a substituted or unsubstituted aryl or heteroaryl ring;

When Q is $Q_3$ or $Q_6$, substituted phenyl is excluded.

BACKGROUND ART

Various substituted phenyl ethers ($I^1$) are known in the literature.

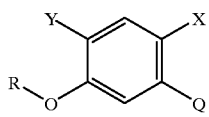

(I')

Q may be pyrazole, imidazole, imidazolidine-2,4-dione, triazolinone, tetrazolinone, aminouracil, etc. R may be hydrogen, alkyl, cycloalkyl, alkenyl or alkynyl. U.S. Pat. No. 5,496,956 discloses arylpyrazoles with the R group selected from propargyl, allyl, or substituted alkyl. JP 6,256,312 discloses phenylimidazoles with the R group selected from hydrogen, $(C_{1-10})$alkyl, $(C_{1-5})$haloalkyl, $(C_{3-5})$alkenyl, $(C_{3-5})$alkynyl, or $(C_{3-6})$cycloalkyl. U.S. Pat. No. 5,125,958 discloses triazolinones with the R group selected from substituted phenyl group. JP 57,197,268 discloses hydantoins with the R group selected lower alkyl. U.S. Pat. No. 4,902,337 discloses hydantoins with the R group selected from hydrogen, alkyl, cycloalkyl, alkenyl or alkynyl. JP 525173 discloses pyrimidinediones with the R group selected from hydrogen, $(C_{1-10})$alkyl, $(C_{1-5})$haloalkyl, ($C_{3-5}$)alkenyl, ($C_{3-5}$)alkynyl, or ($C_{3-6}$)cycloalkyl. U.S. Pat. No. 4,985,065 discloses phenyltetrazolinones with the R group selected from substituted phenyl group. No heteroaryl derivatives were claimed as R. WO 9,602,523 discloses substituted aryliminothiadiazoles with the R group selected from hydrogen, alkyl, cycloalkyl, alkenyl or alkynyl. U.S. Pat. No. 4,452,981 discloses phenylurazoles with the R group selected from ($C_{1-3}$)alkyl, allyl, or propargyl. EP-A-517181(which corresponds to U.S. Pat. No. 5,280,010) discloses aminouracil compounds wherein Q is amino uracil and R is a lower alkyl group. WO96/07323 and WO96/08151 disclose some known uracil compounds. In WO96/08151 the generic representation is significantly broader than the disclosures set forth in it, and in the prior art patents. The specific aminouracil compounds of the formula (I) mentioned below are not known and are novel.

The present invention reveals that some diaryl ethers represented by the general formula (I) or their salts have a potent herbicidal activity with good crop safety.

DISCLOSURE OF THE INVENTION

The need continues for novel and improved herbicidal compounds and compositions. This invention relates to novel diaryl ethers, compositions comprising diaryl ethers, and the use of diaryl ethers and compositions thereof as broad spectrum herbicides which are effective against both monocot and dicot weed species in preemergence and postemergence application and are sometimes safe to crops. The compounds and compositions of the present invention can also be sometimes used as desiccants. This invention also includes methods of preparing these compounds and intermediates thereof as well as methods of using the compound as herbicides.

This invention relates to diaryl ether compounds having the general formula I and their salts (I)

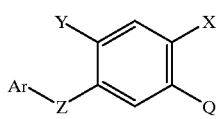

wherein
X, Y are independently hydrogen, halogen, cyano, nitro, or ($C_{1-6}$)haloalkyl and
Z is oxygen or sulfur and
Q is selected from $Q_1$

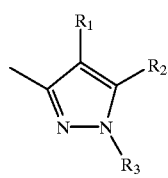

$Q_2$

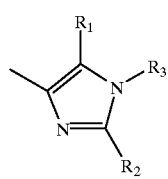

-continued $Q_3$

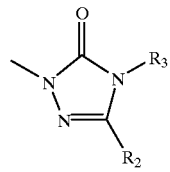

$Q_4$

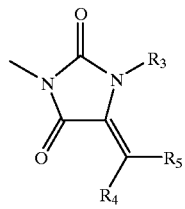

$Q_5$

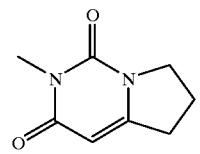

$Q_6$

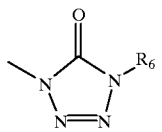

$Q_7$

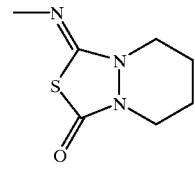

$Q_8$

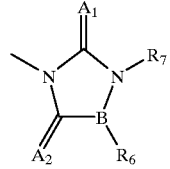

$Q_9$

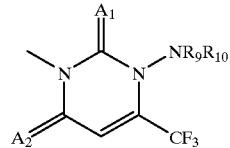

$R_1$ is halogen;
$R_2$, $R_3$, $R_4$ and $R_5$ are independently hydrogen, ($C_{1-6}$)alkyl, or ($C_{1-6}$)haloalkyl;
When $R_3$ and $R_5$ are taken together with the atoms to which they are attached, they represent a four to seven membered substituted or unsubstituted ring optionally interrupted by O, S(O)$_n$ or N—$R_4$, and optionally substituted with one to three ($C_{1-6}$)alkyl group or one or more halogen atoms;
$R_6$ is hydrogen, ($C_{1-6}$)alkyl, ($C_{2-6}$)alkenyl, ($C_{2-6}$)alkynyl, ($C_{1-6}$)haloalkyl, ($C_{2-6}$)haloalkenyl, ($C_{2-6}$)haloalkynyl, ($C_{1-6}$)cyanoalkyl, ($C_{1-6}$)alkoxy-($C_{1-6}$)alkyl, or ($C_{1-6}$)alkylthio-($C_{1-6}$)alkyl;

$A_1$ and $A_2$ are independently oxygen or sulfur;

B is CH or N;

$R_7$ and $R_8$ are each independently hydrogen, $(C_{1-6})$alkyl optionally substituted with one or more halogen atoms, or $(C_{3-6})$cycloalkyl optionally substituted with one or more halogen atoms, and when $R_7$ and $R_8$ are taken together with the atoms to which they are attached, they represent a four to seven membered substituted or unsubstituted ring optionally interrupted by O, $S(O)_n$ or N—$R_4$, and optionally substituted with one to three $(C_{1-6})$alkyl groups or one or more halogen atoms;

n is an integer of 0, 1, or 2.

$R_9$ and $R_{10}$ are hydrogen, $(C_{1-6})$alkyl, acyl, or $(C_{1-6})$alkylsulfonyl or $R_9$ and $R_{10}$ may form a ring consisting of polymethylene, $(CH_2)_m$ groups, where m is an integer of 2, 3, 4 or 5, together with the nitrogen atom of $NR_9R_{10}$, which may or may not have a $(C_{1-6})$alkyl substituent.

Some compounds of formula (1) and their intermediates may occasionally exist as geometrical or optical isomers and the present invention includes all of these isomeric forms Some compounds of the formula (I) and their intermediates may form a salt with an acidic substance or a basic substance. The salt with an acidic substance may be an inorganic acid salt such as a hydrochloride, a hydrobromide, a phosphate, a sulfate or a nitrate. The salt with a basic substance may be a salt of an inorganic or organic base such as a sodium salt, a potassium salt, a calcium salt, a quarternary ammonium salt such as ammonium salt or a dimethylamine salt.

Ar is a substituted or unsubstituted aryl or heteroaryl ring; When Q is $Q_3$ or $Q_6$, substituted phenyl is excluded.

This invention also relates to compositions containing those compounds and methods for using those compounds and compositions. The compounds and compositions of the present invention are especially useful for the selective control of undesirable plant species occasionally in the presence of crops. The compounds and compositions of the present invention can also be used as desicants.

DETAILED DESCRIPTION OF THE INVENTION

The present invention provides a method for controlling undesirable plant species by preemergence or postemergence application.

The diaryl ether compounds of this invention have the general formula I

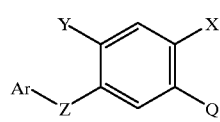

(I)

wherein X, Y, Z, Ar, and Q are as described above.

The aryl in the definition of Ar may be phenyl or naphthyl, and the heteroaryl in the definition of Ar may be a five or six membered ring having at least one heterogeneous atom of nitrogen, oxygen or sulfur, and for example may be pyridyl, pyrimidyl, pyridazinyl, triazolyl, thiazolyl or isothiazolyl. The substituents for the substituted aryl or heteroaryl ring may, for example, be halogen, $(C_{1-6})$alkyl, halo$(C_{1-6})$alkyl, $(C_{1-6})$alkoxy, halo$(C_{1-6})$alkoxy, $(C_{1-6})$alkylthio, $(C_{1-6})$alkylsulfonyl, $(C_{1-6})$alkylsulfinyl, $(C_{1-6})$dialkylaminocarbonyl, cyano, nitro, amino, hydroxy, $(C_{1-6})$alkylsulfonylamino, $(C_{1-6})$alkoxycarbonyl$(C_{1-6})$alkoxy, $(C_{1-6})$ alkylcarbonylamino, bisbenzoylamino, aminoacetyl, aminotifluoroacetyl, or amino$(C_{1-6})$allylsulfonate. The number of substituents is one or more, for example up to five. When the number is two or more, the substituents may be same or different.

The alkyl group and alkyl part in the definition related to X, Y, $R_2$ to $R_{10}$ and the substituents for the substituted aryl and heteroaryl ring as Ar have the straighted or branched chains with $C_{1-6}$, preferably $C_{1-4}$ such as methyl, ethyl, propyl, butyl, pentyl, or hexyl. The alkenyl or alkynyl group and their parts in the definition for $R_6$ have also the straighted or branched chains with $C_{2-6}$, preferably $C_{2-4}$ such as vinyl, propenyl, butenyl, pentenyl, hexenyl, ethynyl, propynyl, butynyl, pentynyl, or hexynyl.

The halogen atom and halogeno part in the definition related to X, Y, $R_1$ to $R_8$ are fluorine, chlorine, bromine, or iodine. The haloalkyl, haloalkenyl or haloalkynyl group constitutes the alkyl, alkenyl or alkynyl group and one or more halogen atoms as mentioned above. When the number of halogen atom is two or more, halogen atoms may be same or different.

Preferred formula I compounds of this invention are those wherein

X, Y are independently hydrogen, or halogen;

Z is oxygen or sulfur;

Q is selected from $Q_1$, $Q_2$, $Q_4$, $Q_6$, $Q_7$, $Q_8$, or $Q_9$.

Ar is pyridyl, pyrimidyl, triazolyl, thiazolyl, isothiazolyl, or phenyl or pyridyl, pyrimidyl, triazolyl, thiazolyl, isothiazolyl, or phenyl substituted with up to five substituents independently selected from bromo, chloro, fluoro, iodo, $(C_1-C_4)$alkyl, halo$(C_{1-4})$alkyl, $(C_{1-4})$ alkoxy, $(C_{1-4})$alkylthio, halo$(C_{1-4})$alkoxy, $(C_{1-4})$ alkylsulfonyl, $(C_1-C_3)$alkylsulfinyl, di$(C_{1-4})$ alkylaminocarbonyl, cyano, nitro, amino, hydroxy, $(C_{1-4})$ alkylsulfonylamino, $(C_{1-4})$alkoxycarbonyl$(C_{1-4})$ alkoxy, or $(C_{1-4})$alkoxycarbonylamino; When Q is $Q_6$, substituted phenyl is excluded.

The most preferred formula I compounds of this invention are those wherein

X is fluorine;

Y is chlorine;

Z is oxygen or sulfur;

Q is selected from $Q_1$, $Q_2$, $Q_4$, $Q_6$, $Q_7$, $Q_8$, or $Q_9$.

Ar is 2-pyridyl, 3-pyridyl, 4-pyridyl, 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 5-amino-2-pyridyl, 3-dimethylaminocarbonyl-2-pyridyl, 3-methylsulfonyl-2-pyridyl, 3-isopropylsulfonyl-2-pyridyl, 6-chloro-3-trifluorometbyl-2-pyridyl, 3,5,6-trifluoropyridyl, 2-pyrimidyl, 4-pyrimidyl, 5-bromo-2-pyrimidyl, 4-chloro-2-pyrimidyl, 4-trifluoromethyl-2-pyrimidyl, 4,6-dimethoxy-2-pyrimidyl, 2,6-dimethoxy-4-pyrimidyl, 4,6-dimethoxy-2-triazinyl, phenyl, 2-iodophenyl, 2-trifluoromethoxyphenyl, 2-nitrophenyl, 4-nitrophenyl, 4-aminophenyl, 4-hydroxyphenyl, 4-methylsulfonylaminophenyl, 4-(1-ethoxycarbonylethoxy)phenyl, 2-cyanophenyl, 2-cyano-3-fluorophenyl, 2-cyano-4-fluorophenyl, 2-amino-4-(1-ethoxycarbonylethoxy)-phenyl, 2-cyano-4-nitrophenyl, 4-amino-2-cyanophenyl, 4-nitro-2-trifluoromethylphenyl, 4-amino-2-trifluoromethylphenyl, 4-acetylamino-2-trifluoromethylphenyl, 4-(1-ethoxycarbonylethoxy)-2-nitrophenyl, 5-chloro- 4-(1-ethoxycarbonylethoxy)-2-nitrophenyl, 3-methyl-4-nitro-5-isothiazolyl,or 5-nitro-2-thiazolyl; When Q is $Q_6$, substituted phenyl is excluded.

The intermediates II and III can be prepared by the methods mentioned in Process (1).

Process 1

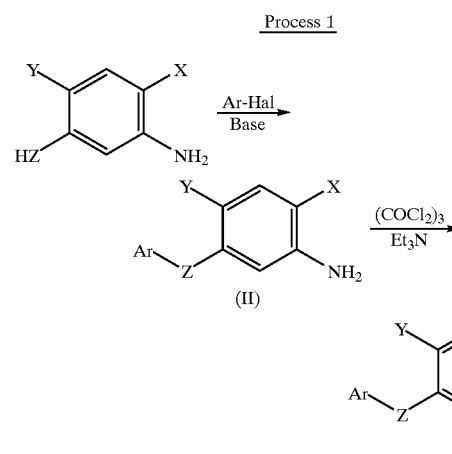

Process (1) is carried out in two stages. The first step is the reaction of an aminophenol with an aryl halide or an heteroaryl halide with or without solvents. The solvents may include acetonitrile, tetrahydrofuran, dimethyl imidazolidine, dimethylsulfoxide, hexamethylphosphoric triamide, N,N-dimethylformamide, acetone, butan-2-one, benzene, toluene or xylene, in the presence of a base such as potassium carbonate, sodium carbonate, potassium hydroxide, sodium hydroxide, potassium t-butoxide, potassium fluoride, or sodium hydride. Catalysts may or may not be used. Such catalysts include copper(1)chloride, copper (1)oxide, copper, copper(1)alkoxide, alkyl cuprate, palladium(0), tetrabutylammonium halides, or 8-quinolinol. The reaction temperature is usually from 0° C. to 250° C., preferably from 20° C. to 120° C. The reaction time is from 1 to 12 hours, preferably from 2 to 6 hours. The diaryl ethers (II) may also be prepared by treatment of an aminophenol with aryl-lead tricarboxylates, triphenylbismuth-diacetate, triphenylbismuth-trifluoroacetate or diphenyliodonium halides in the presence of solvents such as benzene, toluene, dichloromethane, dichloroethane, chloroform or water, with or without catalysts such as copper, or a transition metal. The temperature is usually from 0° C. to the reflux temperature of the mixture, and the reaction time from 10 minutes to 72 hours. The temperature is preferably from 20° C. to the reflux temperature of the mixture, and the time preferably 2 to 6 hours.

The second step requires treatment of the amine (II) with phosgene or triphosgene in a solvent such as hexane, heptane, benzene, toluene, xylene, or ethyl acetate. The reaction temperature is usually from 0° C. to the reflux temperature of the mixture, preferably at the reflux temperature of the mixture. The reaction time is usually from 30 minutes to 6 hours, preferably from 2 to 3 hours.

Process 2

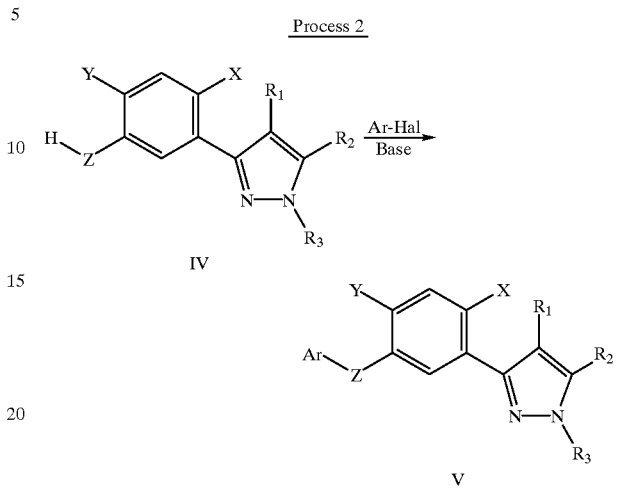

In Process (2) the ether linkage is formed using the conditions described in the first stage of Process (1).

Process 3

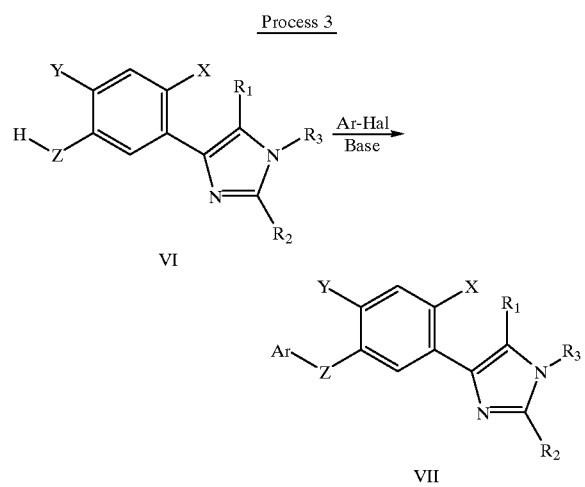

In Process (3) the ether linkage is formed using the conditions described in the first stage of Process (1).

Process 4

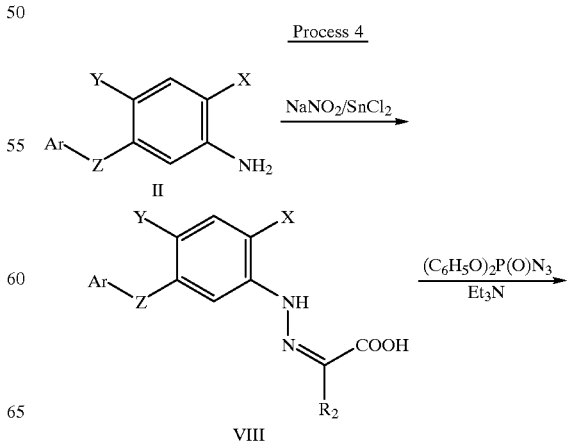

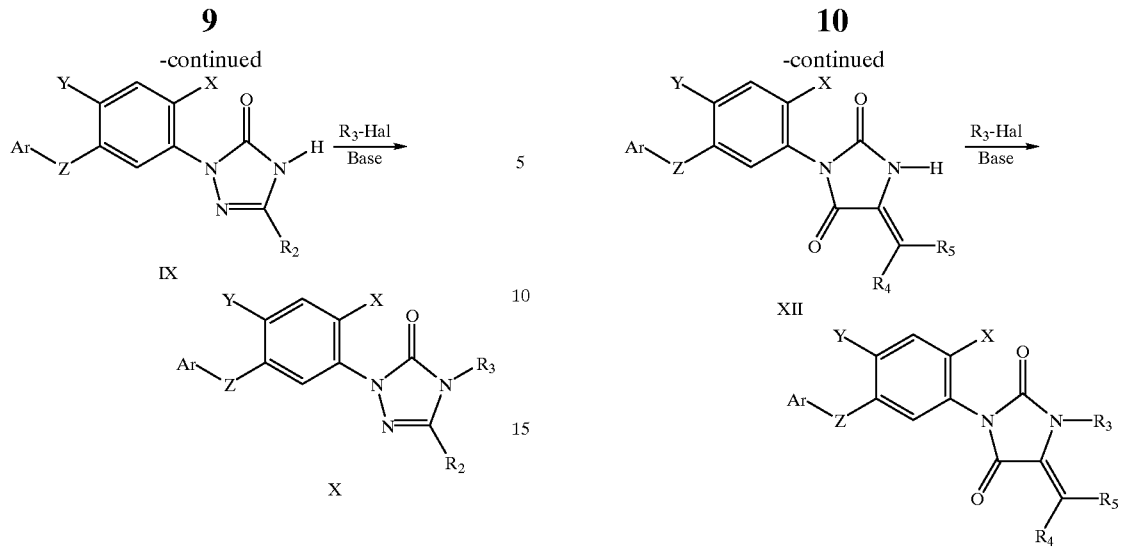

Process (4) proceeds in three stages. The first step is the formation of a diazonium salt of aniline (II) usually in an acidic medium such as conc. hydrochloric acid when treated with aqueous sodium nitrite solution. It is reduced in the presence of a reducing agent to give the corresponding hydrazine derivative. Such a reducing agent could be an inorganic compound such as hydrated tin(II)chloride. This is treated with a ketoacid such as pyruvic acid in aqueous solution. The reaction temperature is between −15° C. to 30° C. and the time from 30 minutes to 4 hours. The preferred temperature initially is between 0° C. and 5° C. and later at 20° C. to 30° C. and the preferred time is from 30 to 60 minutes.

In the second step the prepared hydrazone (VIII) is treated with diphenylphos-phoryl azide in an inert solvent such as benzene, toluene, xylene, hexane, in the presence of a base such as triethylamine or pyridine. The reaction temperature is between 20° C. and the reflux temperature of the mixture and the time from 30 minutes to 6 hours. Preferably the temperature is the reflux temperature of the mixture and the time is from 1 to 2 hours.

The final stage is the alkylation of (IX) in an inert solvent such as diethyl ether, dioxane or tetrahydrofuran with an alkylating agent such as an alkyl halide, haloalkyl halide, or alkyl sulfate, in the presence of a base such as sodium or potassium hydroxide, sodium or potassium carbonate, pyridine or triethylamine with or without a catalytic amount of a tetraalkylammonium salt. The reaction temperature is between −40° C. to 50° C. and the time from 30 minutes to 4 days. The preferred reaction temperature is between 20° C. to 30° C., the preferred reaction time is 2 days.

Process (5) proceeds in three stages. The first step is the treatment of the isocyanate (IIIa) with ammonia in an inert solvent such as hexane, benzene, toluene, xylene, diethyl ether, tetrahydrofuran or dioxane. The reaction temperature is between −10° C. to 100° C. and the time from 15 minutes to 6 hours. The reaction temperature is preferably between 0° C. and 10° C., and the time from 30 to 60 minutes.

The second step is the treatment of the urea (XI) with an acid catalyst such as p-toluenesulfonic acid or amberlyst resin. and a ketoester, in an inert solvent such as benzene, toluene, xylene, hexane, at a temperature between 20° C. and the reflux temperature of the mixture, from 10 to 24 hours, to give the imidazolidinone (XII). The temperature is preferably the reflux temperature of the mixture and the time 12 to 16 hours.

The final stage is the alkylation of (XII) in an inert solvent such as diethyl ether, dioxane, tetrahydrofuran, benzene, toluene, xylene or hexane, with an alkylating agent such as an alkyl halide or haloalkyl halide, in the presence of a base such as sodium or potassium hydroxide, sodium or potassium carbonate, pyridine or triethylamine. The reaction temperature is between 20° C. to the reflux temperature of the mixture, and the time from 30 minutes to 20 hours. Preferably the temperature is between 50° C. and 100° C. and the time from 12 to 16 hour.

Process 5

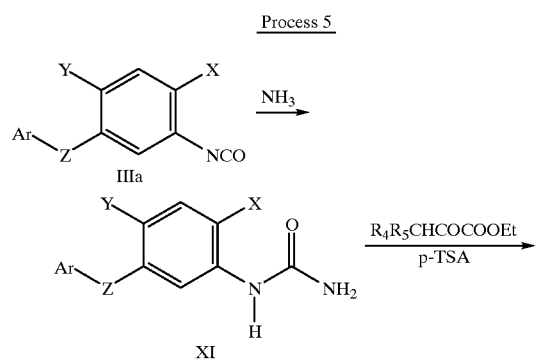

Process 6

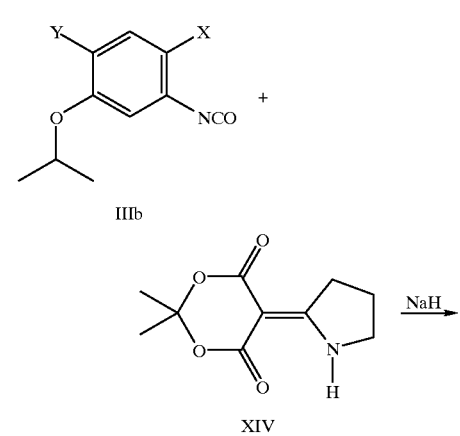

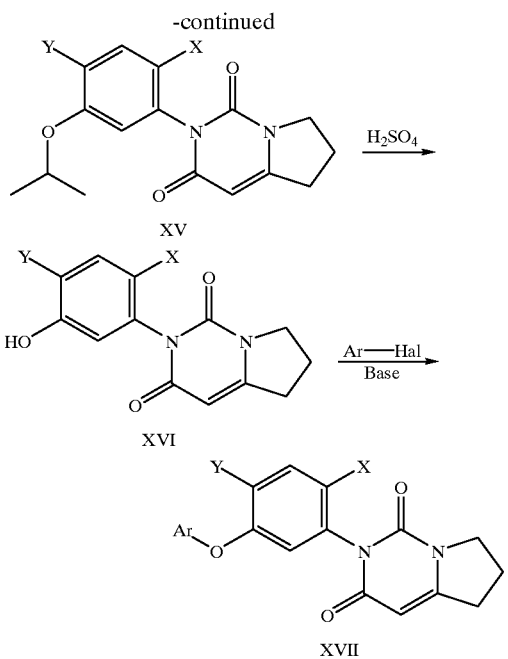

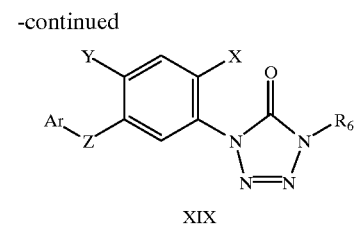

Process (6) proceeds in three stages. The first step is the treatment of the isocyanate (IIIb) with 2,2-dimethyl-5-(2-tetrahydropyrrolylidene)-1,3-dioxane-4,6-dione in the presence of a base such as sodium methoxide, sodium ethoxide, potassium t-butoxide, or sodium hydride in a solvent such as toluene, N,N-dimethylformamide or dimethylsulfoxide. The reaction temperature is between −40° C. to the reflux temperature of the mixture and the time from 30 minutes to 14 hours. Preferably the initial temperature of the addition is between −30° C. to −20° C., and further reaction requires temperatures of between 100° C. and 120° C. The preferred time is from 4 to 5 hours.

The second step is the hydrolysis of the ether linkage under acidic conditions in an inert solvent such as chloroform or ethylene chloride, using conc. sulfuric acid. The reaction temperature is between −20° C. to 50° C. and the time from 30 minutes to 6 hours. Preferably the addition is done at between 0° C. to 5° C., and further reaction requires temperatures of between 20° C. and 30° C. The preferred time is from 1 to 2 hours.

In the final step the ether linkage is formed using the conditions described in the first stage of Process (1).

Process 7

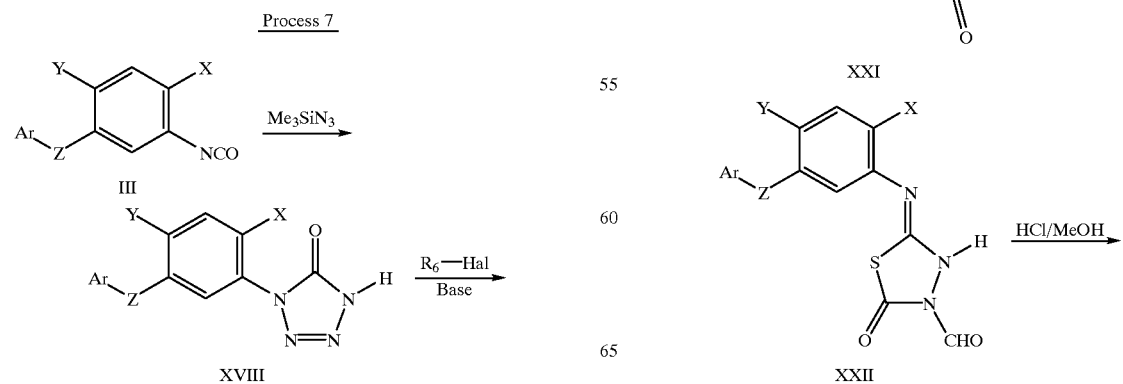

Process (7) proceeds in two stages. The first step is the formation of the tetrazole ring (XVIII) by treatment of the isocyanate (III) with trimethylsilyl azide with or without solvent. The reaction temperature is between 100° C. to the reflux temperature of the mixture and the time from 1 to 48 hours. Preferably the temperature is the reflux temperature of the mixture and the time 24 hours.

The final stage is the alkylation of (XVIII) in an inert solvent such as acetone, diethyl ether, dioxane, tetrahydrofuran, benzene, toluene, xylene, hexane, N,N-dimethyl-formamide or dimethylsulfoxide, with an alkylating agent such as an alkyl halide or an haloalkyl halide in the presence of a base such as sodium or potassium hydroxide, sodium or potassium carbonate, pyridine or triethylamine. The reaction temperature is between 50° C. to 150° C. and the time from 30 minutes to 2 days. The preferred temperature range is between 70° C. and 90° C. and the time from 20 to 30 hours.

Process 8

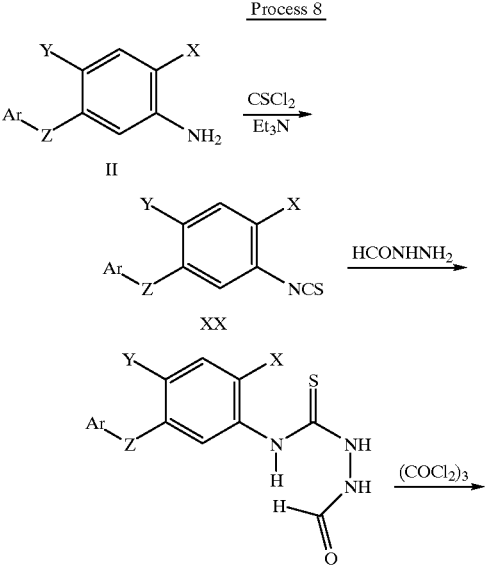

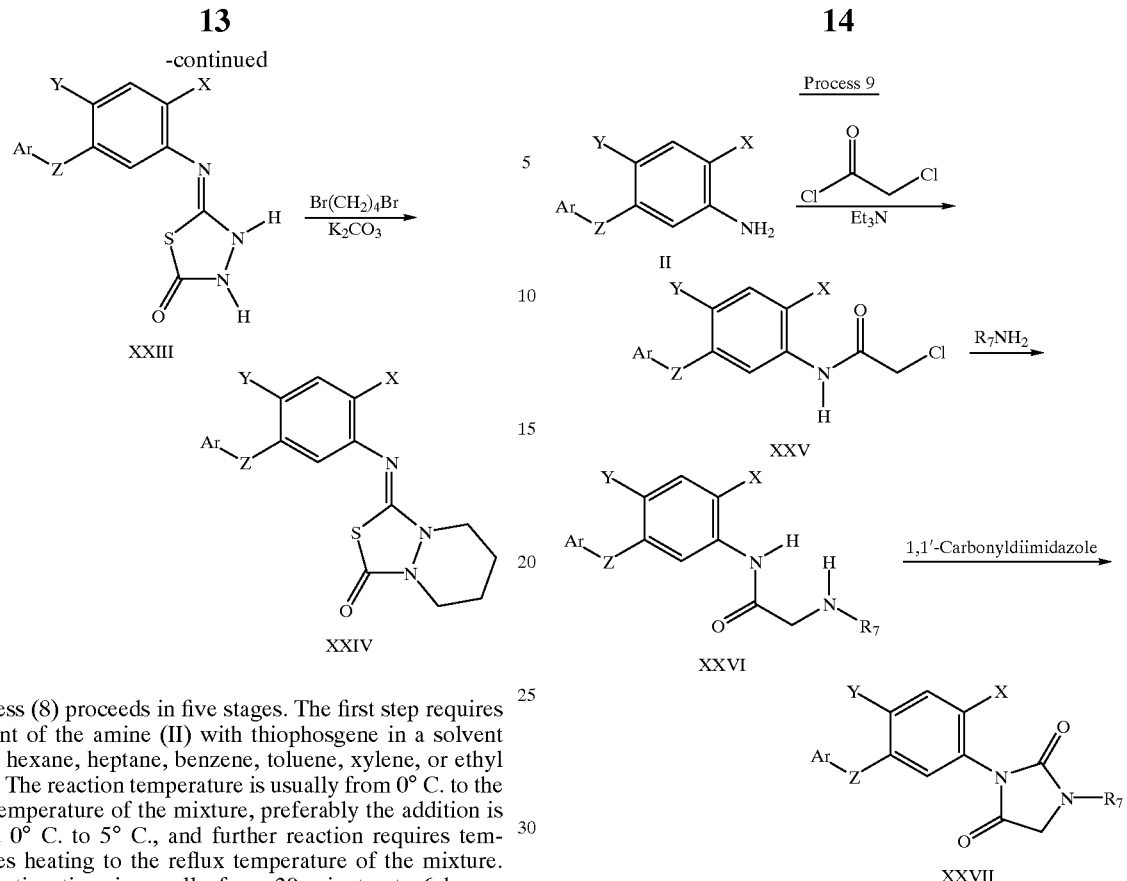

Process (8) proceeds in five stages. The first step requires treatment of the amine (II) with thiophosgene in a solvent such as hexane, heptane, benzene, toluene, xylene, or ethyl acetate. The reaction temperature is usually from 0° C. to the reflux temperature of the mixture, preferably the addition is done at 0° C. to 5° C., and further reaction requires temperatures heating to the reflux temperature of the mixture. The reaction time is usually from 30 minutes to 6 hours, preferably from 2 to 3 hours.

In the second step the isothiocyanate (XX) was treated with formic hydrazide in an inert solvent such as toluene, tetrahydrofuran, dioxane or diethyl ether. The reaction temperature is usually from 0° C. to the reflux temperature of the mixture, preferably at ambient temperature. The reaction time is usually from 30 minutes to 10 hours, preferably from 3 to 4 hours.

The formyl hydrazines (XXI) were treated with phosgene or triphosgene in a solvent such as hexane, heptane, benzene, toluene, xylene, acetone, or ethyl acetate. The reaction temperature is usually from −20° C. to 50° C., preferably between 0° C. and 25° C. The reaction time is usually from 30 minutes to 6 hours, preferably from 1 to 2 hours.

The hydrolysis of the 3-formylthiadiazolidinones (XXII) is done under acidic conditions in such solvents as acetone, butan-2-one, methanol, ethanol, tetrahydrofuran, or N,N-dimethylformamide. The acids may be sulfuric, hydrochloric or acetic acids and may be diluted. The reaction temperature is usually from −20° C. to 50° C., preferably between 0° C. and 25° C. The reaction time is usually from 15 minutes to 6 hours, preferably from 30 minutes to 2 hours.

The final stage is the alkylation of (XXIII) in an inert solvent such as acetone, diethyl ether, dioxane, tetrahydrofuran, benzene, toluene, xylene, hexane, N,N-dimethyl-formamide or dimethylsulfoxide, with an alkylating agent such as an alkyl halide or a haloalkyl halide, in the presence of a base such as sodium or potassium hydroxide, sodium or potassium carbonate, pyridine or triethylamine. The reaction temperature is between 30° C. to the reflux temperature of the mixture and the time from 30 minutes to 6 hours. The preferred temperature range is between 50° C. and 90° C. and the time from 1 to 3 hours.

In Process (9) amines (II) are transformed into the 2,4-imidazolidinediones (XXVII) in three stages. In the first step treatment with a haloacetyl halide, such as chloroacetyl chloride and an organic base such as triethylamine or pyridine, in an inert solvent such as benzene, toluene, xylene, tetrahydrofuran, or N,N-dimethylformamide gave the chloroamides (XXV). The preferred acylating agent is chloroacetyl chloride and the preferred base triethylamine. The preferred solvent is toluene. The reaction may be carried out at temperatures between −20° C. and 150° C., preferably between 25° C. and 50° C. The reaction time may be from 30 minutes to 10 ten hours, preferably between 2 and 4 hours.

In the second step reaction of these chloroamides (XXV) with suitable amines in a solvent such as $C_{1-5}$ alcohols, tetrahydrofuran, or dioxane gave amino-amides (XXVI). The preferred solvent is ethanol, and the reaction may be carried out at temperatures between −20° C. and 150° C., preferably between 25° C. and 70° C. The reaction time may be from 30 minutes to ten hours, preferably between 2 and 3 hours.

In the third step the amino-amides (XXVI) are treated with 1,1¹-carbonyldi-imidazole in an inert solvent such as benzene, toluene, xylene, tetrahydrofuran, or N,N-dimethylformamide and yielded the 2,4-imidazlidinediones (XXVII). The preferred solvent is toluene, and the reaction may be carried out at temperatures between −20° C. and 150° C., preferably between 100° C. and 120° C. The reaction time may be from 30 minutes to ten hour, preferably between 2 and 3 hours.

Process 10

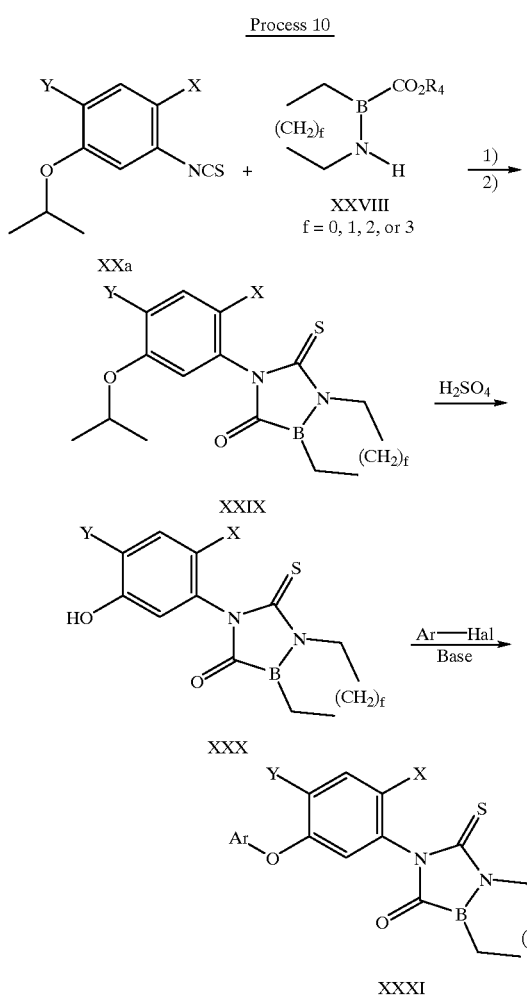

Process (10) proceeds in three stages. The first is the reaction of isothiocyanates (XXa) with a saturated cyclic heterocycle (XXVIII) such as 1-ethyloxycarbonylhexahydropyridazine, where B=N and f=2, and may or may not be done in two parts, (1) and (2). In part (1) they are stirred together in an inert solvent such as benzene, toluene, xylene, dioxane, hexane, ethyl acetate, tetrahydrofuran, diethyl ether, or acetone. The reaction temperature is usually from −70° C. to the reflux temperature of the mixture, depending on the nature of B, f, and $R_4$. The reaction time is usually from 30 minutes to 20 hours, depending on the nature of B, f, and $R_4$. In part (2) after removal of the solvent toluene, xylene, or dioxane may be added, and also a weakly basic compound such as sodium acetate. The reaction proceeds at a temperature of between 50° C. to the reflux temperature of the mixture and the time from 6 hours to 3 days. The preferred temperature is the reflux temperature of the mixture and the time from 20 to 30 hours.

The second step is the hydrolysis of the ether linkage under acidic conditions in an inert solvent such as chloroform or methylene chloride, using conc. sulfuric acid. The reaction temperature is between −20° C. to 50° C. and the time from 30 minutes to 6 hours. Preferably at 0° C. and a time of 1 to 2 hours.

The final step is the formation of the ether linkage to give (XXXI). This is done using the conditions described in the first stage of Process (1).

Process 11

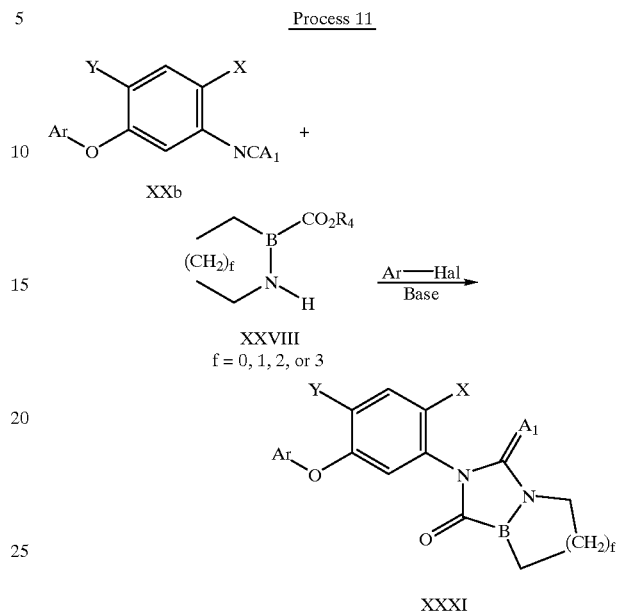

Process (11) is a one step process where a compound (XXb), which may be an isocyanate or an isothiocyanate, reacts with a saturated cyclic heterocycle (XXVIII), with or without solvents, to give the product (XXXI). The reaction is enhanced by the presence of solvents such as hexane, pentane, benzene, toluene, xylene, diethyl ether, tetrahydrofuran, dioxane, acetone, butan-2-one, ethyl acetate, N,N-dimethylformamide or dimethyl-sulfoxide, and is conducted between −70° C. to the reflux temperature of the mixture and from 15 minutes to 20 hours. The temperature is preferably between 0° C. and 30° C., and the time from 15 minutes to 12 hours.

Process 12

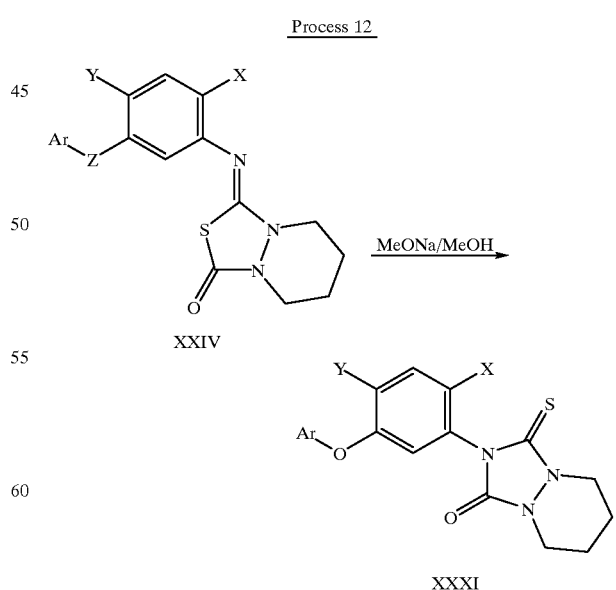

In Process (12) the thiadiazabicyclononanones (XXIV) are treated with a catalytic amount of a base such as sodium methoxide, sodium ethoxide, or potassium t-butoxide in a C$_{1-5}$ alcohol such as methanol, ethanol or t-butanol, at a temperature between 0° C. and the reflux temperature of the mixture from 15 minutes to 3 hours. Preferably at the reflux temperature of the mixture and from 30 to 60 minutes.

Process 13

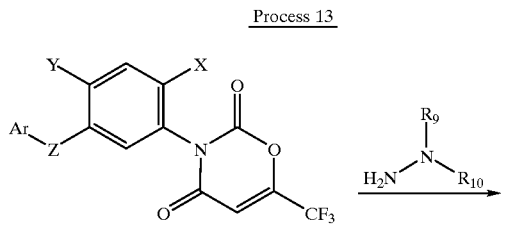

XXXII

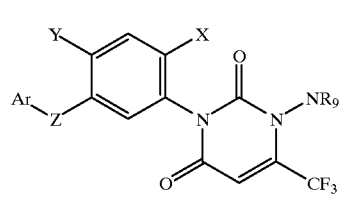

XXXIII

Process (13) is carried out using 0.5 to 10 equivalents (preferably 0.8 to 3) of the hydrazines relative to the oxazines (XXXII). Examples of hydrazines include hydrazine, alkyl hydrazines such as methyl, ethyl, or t-butylhydrazine, and cyclic hydrazines such as 1-aminopyrrolidine. The reaction proceeds without any solvents but is normally accelerated by employing solvent.

Further reaction requires solvents such as aliphatic hydrocarbons e,g, hexane, heptane, ligroin and petroleum ether, aromatic hydrocarbons such as benzene, toluene, xylene, and chlorobenzene, halogenated hydrocarbons such as chloroform and methylene chloride, ethers such as diethyl ether, dioxane, and tetrahydrofuran, ketones such as acetone and methyl ethyl ketones, nitrites such as acetonitrile and isobutyronitrile, tertiary amines such as pyridine and N,N-dimethylaniline, acid amides such as N,N-dimethylacetamide, N,N-dimethylformamide, and N-methylpyrrolidone, sulfur containing compounds such as dimethylsulfoxide and sulfolane, alcohols such as methanol, ethanol, propanol, and butanol, water and the mixtures thereof.

The reaction temperature is usually from −30° C. to 150° C., preferably from −10° C. to the reflux temperature of the reaction mixture. The reaction time requires normally from 10 minutes to 96 hours, preferably from 30 minutes to 48 hours.

Process 14

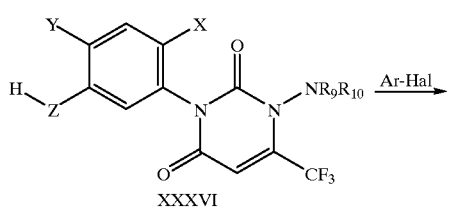

XXXVI

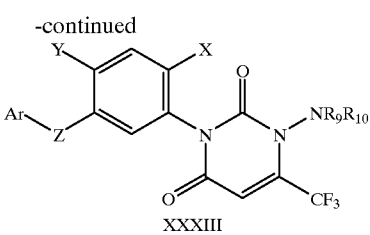

XXXIII

In Process (14) the ether linkage is formed using the conditions described in the first stage of Process (1).

Process 15

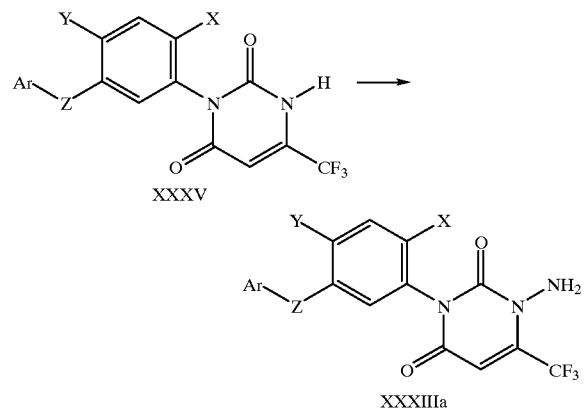

XXXIIIa

Process (15) is carried out in a solvent such as dioxane, dimethylsulfoxide, hexamethylphosphoric triamide or N,N-dimethylformamide in the presence of a base such as sodium carbonate, potassium carbonate, sodium hydroxide, potassium hydroxide, or sodium hydride. A number of aminating agents may be used such as 2,4-dinitro-phenoxyamine; O-arylsulfonylhydroxyamines such as 2,3,6-trimethyl- and triisopropyl-phenylhydroxyamine; O-picoylhydroxyamine; and O-mesitylhydroxyamine. The reaction temperature is usually from −30° C. to 110° C., and the reaction time is from 12 hours to 7 days. The reaction temperature is preferably from 20° C. to 30° C. The reaction time is preferably from 12 hours to 3 days.

Process 16

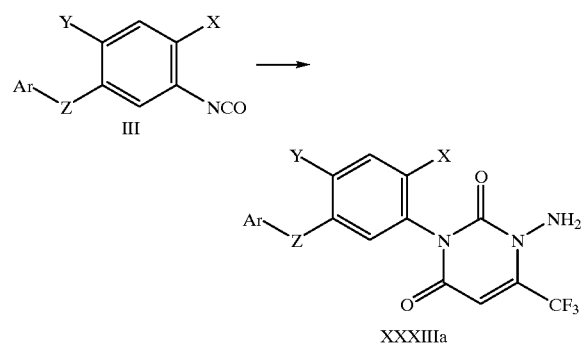

XXXIIIa

Using Process (16) the isocyanate (III) may be used to form the aminouracil (XXXIIIa) in a one pot synthesis without isolating the uracil (XXXV). The uracil ring is formed by reacting the prepared isocyanate (III) with an alkyl 3-amino-4,4,4-trifluoro-crotonate and a base such as sodium hydride, sodium methoxide or sodium ethoxide, in a solvent such as dimethylsulfoxide, N,N-dimethylformamide, benzene, toluene, xylene, tetrahydrofuran, dioxane, or diethyl ether, at temperatures usually from −50° C. to 50° C., with a reaction time from 10 minutes to 14 hours. Preferably between −30° C. to 30° C., with a reaction time of 15 minutes to 6 hours. Aminating agents, such as 2,4-dinitro-phenoxyamine; O-arylsulfonylhydroxyamines such as 2,3,6-trimethyl- and triisopropyl-phenylhydroxyamine; O-picoylhydroxyamine; and O-mesitylhydroxyamine are then introduced, as described for Process (15). The reaction temperature is usually from −30° C. to 110° C., and the reaction time is from 12 hours to 7 days. The reaction temperature is preferably from 20° C. to 30° C. The reaction time is preferably from 12 hours to 3 days.

Process 17

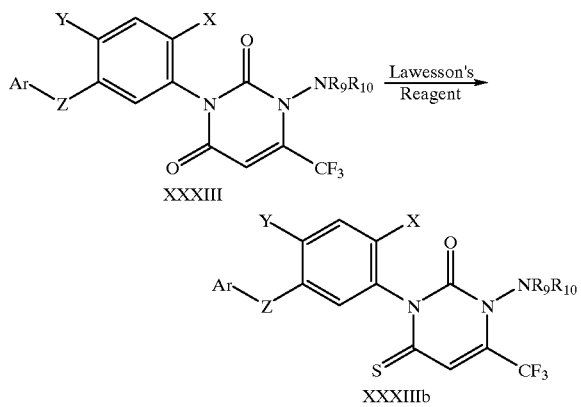

Using Process (17) a compound of formula ($Q_9$) wherein $A_1$ and/or $A_2$ are/is a sulfur atom, can be prepared by reacting a compound of the above formula (XXXIII) with a sulfurizing agent such as Lawesson's reagent or phosphorus pentasulfide. Further sulfurization may occur with prolonged heating and with excess reagent. The reaction uses solvents such as benzene, toluene and xylene. The reaction time is usually 2 to 12 hours, preferably 3 to 4 hours The reaction temperature is usually 0° C. to 150° C., preferably between 60° C. and the reflux temperature of the mixture.

Process 18

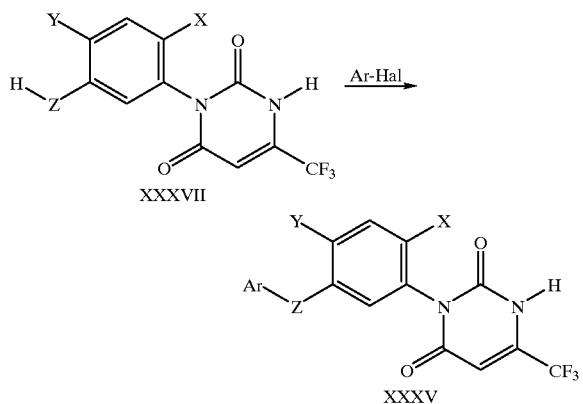

In Process (18) the ether linkage is formed using the conditions described in the first stage of Process (1).

Process 19

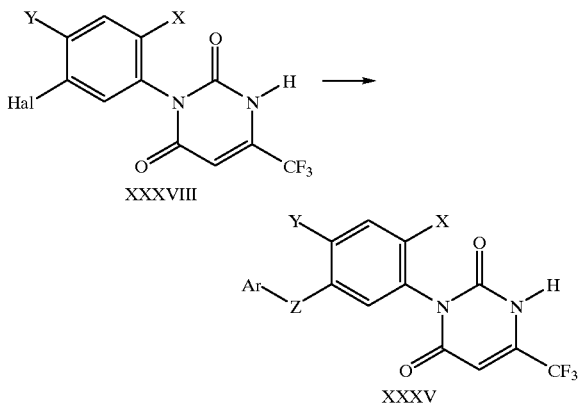

Process (19) requires the reaction of the sodium or potassium salt of an aromatic- or heterocyclic hydroxyl compound with the haloaromatic uracil (XXXVIII). The reaction proceeds without any solvent but is normally accelerated by employing solvent. These include toluene, xylene, N,N-dimethylformamide, and dimethylsulfoxide, and a catalyst is used such as copper, copper bronze, or a transition metal. The temperature is usually from 0° C. to 150° C., and the reaction time from 10 minutes to 72 hours. The temperature is preferably from 150° C. to the reflux temperature of the mixture, and the time preferably 2 to 6 hours.

Process 20

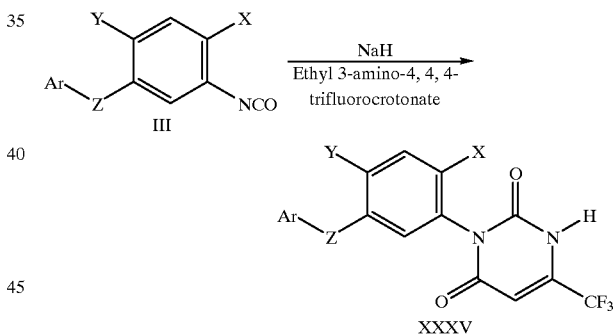

Process (20) shows how the uracil ring may be formed by reacting the prepared isocyanate (III) with an alkyl 3-amino-4,4,4-trifluorocrotonate and a base such as sodium hydride, sodium methoxide, sodium ethoxide, or potassium t-butoxide, in a solvent such as dimethylsulfoxide, N,N-dimethylformamide, benzene, toluene, xylene, tetrahydrofuran, dioxane, or diethyl ether, at temperatures usually from −50° C. to 50° C., with a reaction time from 10 minutes to 14 hours. Preferably from −30° C. to 30° C., with a reaction time of 15 minutes to 6 hours.

Process 21

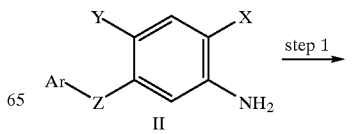

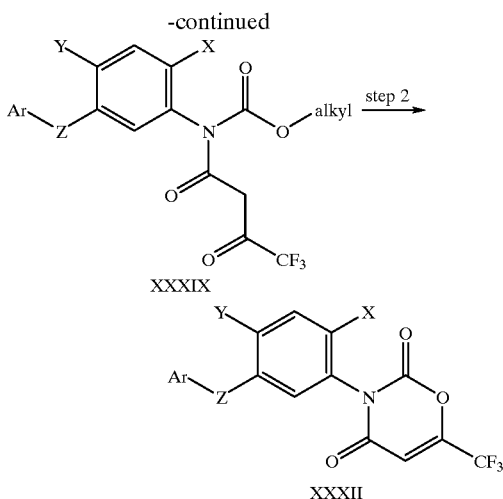

Process (21) is carried out in two stages. The first step is the preparation of N-phenyl-acetamide (XXXIX) using conventional methodology.

The second step is the cyclization to give the oxazines (XXXII). This is carried out in solvents which are aliphatic hydrocarbons such as hexane, heptane, ligroin, and petroleum ether, aromatic hydrocarbons such as benzene, toluene, xylene, and chloro-benzene, tertiary amines such as pyridine, and N,N-diethylaniline, acid amides such as N,N-dimethylacetamicle, N,N-dimethylformamide, and N-methylpyrrolidone, sulfur containing compounds such as dimethylsulfoxide and sulfolane, and organic acids such as formic acid, acetic acid, lactic acid, and acetic anhydride. Preferably used are the above mentioned aliphatic hydrocarbons, aromatic hydrocarbons and organic acids. The reaction temperature is usually from 0° C. to 200° C., preferably from 20° C. to the reflux temperature of the mixture. The reaction time is from 10 minutes to 72 hours, preferably from 30 minutes to 24 hours.

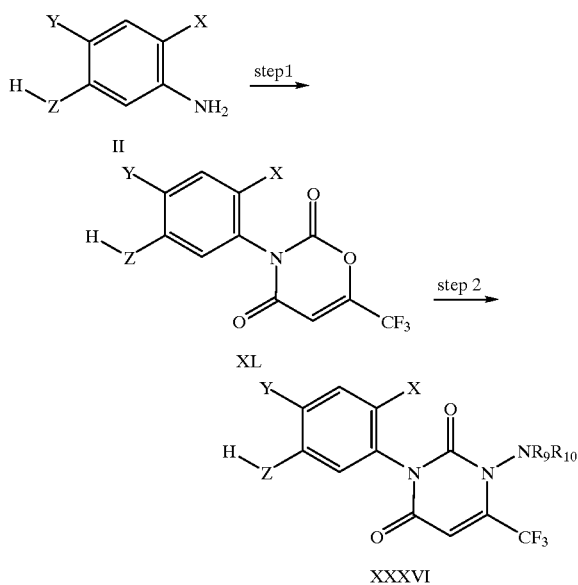

Process (22) is carried out in two stages. The first step is the formation of the phenolic oxazine (XL) using the methodology described in Process (21). This is carried out in solvents which are aliphatic hydrocarbons such as hexane, heptane, ligroin, and petroleum ether, aromatic hydrocarbons such as benzene, toluene, xylene, and chlorobenzene, tertiary amines such as pyridine, and N,N-diethylaniline, acid amides such as N,N-dimethylacetamide, N,N-dimetbylformamide, and N-methylpyrrolidone, sulfur containing compounds such as dimethylsulfoxide and sulfolane, and organic acids such as formic acid, acetic acid, lactic acid, and acetic anhydride. Preferably used are the above mentioned aliphatic hydrocarbons, aromatic hydrocarbons and organic acids. The reaction temperature is usually from 0° C. to 200° C., preferably from 20° C. to the reflux temperature of the mixture. The reaction time is from 10 minutes to 72 hours, preferably from 30 minutes to 24 hours.

The second step is carried out under the same conditions described for Process (13).

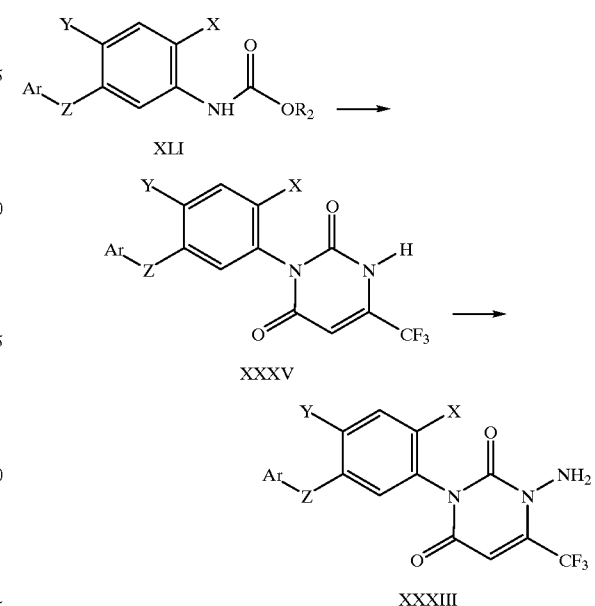

Process (23) is carried out in two stages. The starting material for the first step, carbamates (XLI), are prepared by conventional methodology. These are treated with an alkyl 3-amino-4,4,4-trifluorocrotonate under the conditions described for Process (20). The second step is carried out under the same conditions described for Process (15).

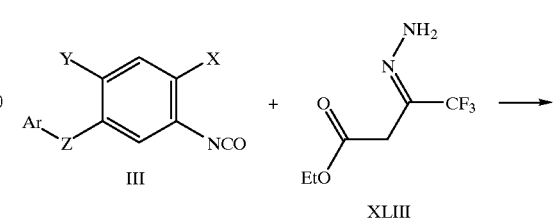

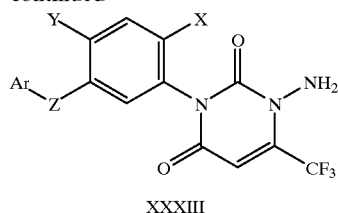

XXXIII

In Process (24) the isocyanate (III) is treated with the hydrazono compound (XLIII) under the conditions described for Process (20) to give the desired product (XXXIII).

Although some embodiments of the present invention are described as follows, the scope of the present invention is not limited to such an embodiment.

Preparation Examples for the compounds of the present invention will be described. The preparation of 3-(4-chloro-2-fluoro-5-hydroxyphenyl)-6-trifluoromethyl-1,2,3,4-tetrahydropyrimidine-2,4-dione is described in U.S. Pat. No. 4,859,229. Lawesson's reagent, [2,4-bis(4-methoxyphenyl)-1,3-dithia-2,4-diphosphetane-2,4-disulfide], was obtained from Aldrich.

EXAMPLES

General

All temperatures are measured in ° C., conc. means concentrated, and mp represents the melting point. Processed indicates that water and ethyl acetate were added, the solutions separated and the organic phase was dried over sodium sulfate, filtered, and the filtrate was evaporated under reduced pressure. The preparation of 5-amino-2-chloro-4-fluorophenol is described in U.S. Pat. No. 4,484,941. Purity was assessed by thin layer chromatography, liquid chromatography, and checked using $^1$H and $^{13}$C nuclear magnetic resonance spectrometry (NMR) which were obtained on a Varian 300 MHz instrument.

Example 1

Synthesis of 4-chloro-2-fluoro-5-(2-pyrimidyloxy) phenyl Isocyanate (Intermediate IIIc) (Process 1).

1.1

2-(5-Amino-2-chloro-4-fluorophenoxy)pyrimidine (Intermediate IIp).

A mixture of 5-amino-2-chloro-4-fluorophenol (3.57 g), potassium carbonate (3.04 g), and 2-chloropyrimidine (3.20 g) suspended in butan-2-one (100 ml) and dimethylsulfoxide (10 ml) was heated at reflux overnight. The solution was processed and chromatographed on silica gel eluting with ethyl acetate:hexane, 1:2, to yield yellow crystals (4.0 g). $^1$H NMR (acetoned-$d_6$, TMS): 4.75(2H, br s), 6.78(1H, d, J=8.4 Hz), 7.09(1H, d, J=10.6 Hz), 7.15(1H, t, J=4.8 Hz), 8.56(2H, d, J=4.8 Hz).

The following can be similarly prepared:
- 2-(5-Amino-2-chloro-4-fluorophenoxy)-4-chloro-pyrimidine (Intermediate IIq).
- 2-(5-Amino-2-chloro-4-fluorophenoxy)-4,6-dimethoxy-pyrimidine (intermediate IIr).
- 2-(5-Amino-2,4-dichlorophenoxy)-4-chloro-pyrimidine (Intermediate IIs).
- 2-(5-Amino-2-chloro-4-fluorophenoxy)-nitrobenzene (Intermediate IIt).
- 2-(5-Amino-2-chloro-4-fluorophenoxy)-benzonitrile (Intermediate IIu).
- 2-(5-Amino-2-chloro-4-fluorophenoxy)-6-fluoro-benzonitrile (Intermediate IIv).

1.2

4-Chloro-2-fluoro-5-(2-pyrimidyloxy)phenyl isocyanate (intermediate IIIc).

A solution of triphosgene (1.21 g) in ethyl acetate (10 ml) was stirred at 0° C. under nitrogen while a solution of 2-(5-amino-2-chloro-4-fluorophenoxy)pyrimidine (0.96 g) and triethylamine (1.2 ml) in ethyl acetate (10 ml) was added dropwise. The mixture was heated at reflux for 3.5 hours, cooled, filtered, and the filtrate evaporated to give the corresponding isocyanate. $^1$H NMR (CDCl$_3$, TMS): 7.03 (1H, d, J=7.2 Hz), 7.10(1H, t, J=4.8 Hz), 7.31(1H, d, J=8.9 Hz), 8.57(2H, d, J=4.8 Hz).

The following can be similarly prepared:
- 4-Chloro-2-fluoro-5-(3-trifluoromethyl-2-pyrimidyloxy) phenyl isocyanate (Intermediate IIId).
- 4-Chloro-2-fluoro-5-(2-nitrophenoxy)phenyl isocyanate (Intermediate IIIe).
- 4-Chloro-2-fluoro-5-(2-cyanophenoxy)phenyl isocyanate (Intermediate IIIf).
- 4-Chloro-2-fluoro-5-(6-fluoro-2-cyanophenoxy)phenyl isocyanate (Intermediate IIIg).

Example 2

Synthesis of 4-chloro-3-(4-chloro-2-fluoro-5-(4,6-dimethoxy-2-triazinyloxy)phenyl)-1-methyl-5-trifluoromethyl-1H-pyrazole (Compound 1-8) (Process 2).

4-Chloro-3-(4-chloro-2-fluoro-5-hydroxyphenyl)-1-methyl-5-trifluoromethyl-1H-pyrazole (prepared according to the procedure as described in U.S. Pat. No. 5,281,571) (0.25 g, 0.76 mMol) was dissolved in N,N-dimethylformamide (5 ml) and potassium carbonate (0.13 g, 0.91 mMol) and 2-chloro-4,6-dimethoxytriazine (0.16 g, 0.91 mMol) were added. The suspension was stirred at 90° C. for 2 hours under a nitrogen atmosphere and processed. The residue was subjected to column chromatography on silica gel eluting with methylene chloride:methanol, 99:1, to give the title compound (0.29 g, 81.6%). $^1$H NMR (CDCl$_3$, TMS): 4.01 (6H, s), 4.07 (3H, m), 7.35 (1H, d, J=9.1 Hz), 7.45 (1H, d, J=6.6 Hz).

Example 3

Synthesis of 5-chloro-4-(4-chloro-2-fluoro-5-(4,6-dimethoxy-2-triazinyloxy)phenyl)-1-difluoromethyl-2-methylimidazole (Compound 2-4) (Process 3).

5-Chloro-4-(4-chloro-2-fluoro-5-hydroxyphenyl)-1-difluoromethyl-2-methylimidazole (prepared according to the procedure as described in EP 590,834) (0.31 g, 1 mMol) was dissolved in N,N-dimethylformamide (5 ml). Potassium carbonate (0.17 g, 1.2 mMol) and 2-chloro-4,6-dimethoxytriazine (0.21 g, 1.2 mMol) were added and the suspension stirred at 110° C. for 2 hours under an atmosphere of nitrogen. The mixture was processed. and the residue chromatographed on silica gel eluting with methylene chloride:methanol, 98:2, to give the title compound (0.25 g, 55%). $^1$H NMR (CDCl$_3$, TMS): 2.61 (3H, br s), 4.00 (6H, s), 7.17 (1H, t, J=58.1 Hz), 7.29 (1H, d, J=9.3 Hz), 7.53 (1H, d, J=6.6 Hz).

Example 4

Synthesis of 1-[4-chloro-2-fluoro-5-(2-pyrimidyloxy)phenyl]-4-difluoromethyl-3-methyl-1,4-dihydro-1,2,4-triazolin-5-one (Compound 3-1) (Process 4).

4.1

Pyruvic acid, 4-chloro-2-fluoro-5-(2-pyrimidyloxy) phenyl hydrazone.

A solution of sodium nitrite (2.01 g) in water (15 ml) was added dropwise over 10 minutes to a solution of 2-(5-amino-2-chloro-4-fluorophenoxy)pyrimidine (7.0 g) in conc. hydrochloric acid (40 ml) cooled to −10° C. and stirred under an atmosphere of nitrogen. Stirring was continued for 30 minutes at this temperature and a solution of tin(II) chloride dihydrate (16.3 g) in hydrochloric acid (20 ml) was added over 10 minutes. The resulting mixture was stirred for 2 hours at room temperature. Water (20 ml) was added and a solution of pyruvic acid (2.55 g) in water (10 ml) added dropwise. The resulting mixture was stirred for 30 minutes and the yellow precipitate was collected by filtration to give 11.24 g (wet weight) of the desired product.

4.2

1-[4-Chloro-2-fluoro-5-(2-pyrimidyloxy)phenyl]-3-methyl-1,4-dihydro-1,2,4-triazolin-5-one.

Triethylamine (0.4 g) was added to a suspension of pyruvic acid, 4-chloro-2-fluoro-5-(2-pyrimidyloxy)phenyl hydrazone (1.24 g) in toluene (30 ml) at room temperature. Diphenylphosphoryl azide (1.05 g) was added and the resulting mixture was heated at reflux for 1 hour. The solution was processed and the residue chromatographed on silica gel eluting with ethyl acetate to give a yellow solid (0.75 g).

4.3

1-[4-Chloro-2-fluoro-5-(2-pyrimidyloxy)phenyl]-4-difluoromethyl-3-methyl-1,4-dihydro-1,2,4-triazolin-5-one (Compound 3-1).

Chlorodifluoromethane gas was bubbled over several hours through a solution of 1-[4-chloro-2-fluoro-5-(2-pyrimidyloxy)phenyl]-3-methyl-1,4-dihydro-1,2,4-triazolin-5-one (0.43 g) in tetrahydrofuran (100 ml) stirred at room temperature, until the solution was saturated. Potassium hydroxide (0.4 g) and a catalytic amount of tetrabutylammonium bromide were added and the cold bath removed. The mixture was stirred at room temperature for 48 hours. The solution was processed and the resulting oil chromatographed on silica gel eluting with ethyl acetate:hexane:methylene chloride, 1:2:2, to give a colorless oil (0.25 g).

Example 5

Synthesis of 3-[4-chloro-2-fluoro-5-(3-trifluoromethyl-2-pyridyloxy)phenyl]-5-isopropylidineimidazolidine-2,4-dione (Compound 4-1) (Process 5).

5.1

4Chloro-2-fluoro-5-(3-trifluoromethyl-2-pyridyloxy) phenylurea.

A solution 4-chloro-2-fluoro-5-(3-trifluoromethyl-2-pyridyloxy)phenylisocyanate (1.3 g) in toluene (30 ml) was cooled to 5° C. and ammonia gas was bubbled through for 15 minutes. Stirring was continued for a further 30 minutes and the mixture filtered and the filtrate evaporated to give a white solid (1.3 g), $^1$H NMR (CDCl$_3$) 2.40(3H, s), 7.20(5H, m).

5.2

3-[4-Chloro-2-fluoro-5-(3-trifluoromethyl-2-pyridyloxy) phenyl]-5-isopropylideneimidazolidine-2,4-dione (Compound 4-1).

A solution 4-chloro-2-fluoro-5-(3-trifluoromethyl-2-pyridyloxy)phenylurea (1.24 g), ethyl 3-methyl-2-oxobutyrate (0.9 g) and p-toluenesulphonic acid (0.1 g) in toluene (30 ml) was heated at reflux for 14 hours and processed to give a white solid (0.55 g), mp>220° C., $^1$H NMR (CDCl$_3$) 1.90(3H, s), 2.30(3H, s), 7.12(1H, dd, J=5,7 Hz), 7.30(1H d, J=9 Hz), 8.00(1H, d, J=7 Hz), 8.25(1H, m), 8.62(1H, s).

Example 6

Synthesis of 2-[4-chloro-2-fluoro-5-(3-trifluoromethyl-2-pyridyloxy)phenyl]-6,7-dihydropyrrolo[1,2-c]pyrimidine-1,3(2H,5H)-dione (Compound 5-10) (Process 6).

6.1

2-4-Chloro-2-fluoro-5-isopropyloxyphenyl)-6,7-dihydropyrrolo[1,2-c]pyrimidine-1,3(2H,5H)-dione.

4-Chloro-2-fluoro-5-isopropyloxyaniline (9.4 g) and triethylamine (9.4 g) in dry ethyl acetate (110 ml) was stirred at 0° C. and a solution of triphosgene (13.8 g) in ethyl acetate (110 ml) was added dropwise. The mixture was heated at reflux for 2 hours, cooled to room temperature, filtered, and the filtrate evaporated. The crude isocyanate was dissolved in N,N-dimethylformamide (70 ml) and added dropwise to a mixture of sodium hydride (1.2 g) and 2, 2-dimethyl-5-(2-tetrahydropyrrolylidene)-1,3-dioxane-4,6-dione (9.9 g) in N,N-dimethylformamide (50 ml) stirred at −30° C. The mixture was stirred at room temperature for 0.5 hours and at 110° C. for 4 hours. The volume was reduced under reduced pressure and the residue processed. Column chromatography (silica gel, hexane:ethyl acetate, 2:3) yielded 2-(4-chloro-2-fluoro-5-isopropyloxyphenyl)-6,7-dihydro-pyrrolo[1,2-c]pyrimidine-1,3(2H,5H)-dione, (9.0 g, 60%) $^1$H NMR (CDCl$_3$, TMS): 1.36(6H, d, J=6.1 Hz), 2.19(2H, m), 2.99(2H, t, J=7.9 Hz), 3.99(2H, m), 4.46(1H, m), 5.74(1H, s), 6.85(1H, d, J=6.6 Hz), 7.29(1H, d, J=6.6 Hz).

6.2

2-(4-Chloro-2-fluoro-5-hydroxyphenyl)-6,7-dihydropyrrolo[1,2-c]pyrimidine-1,3(2H,5H)-dione.

This was synthesized from 2-(4-chloro-2-fluoro-5-isopropyloxyphenyl)-6,7-dihydropyrrolo[1,2-c]pyrimidine-1,3(2H,5H)-dione in 86% yield under similar conditions as described below for the preparation of 2-(4-chloro-2-fluoro-5-hydroxyphenyl)hexa-hydro-3-thioxo-1H-[1,2,4]triazolo [1,2-a]pyridazin-1-one (Example 10.2). $^1$H NMR (CDCl$_3$, TMS): 2.22(2H, m), 3.06(2H, t, J=7.5 Hz), 3.13(1H, br), 4.01(2H, t, J=6.5 Hz), 5.71(1H, s), 6.87)1H, d, J=6.9 Hz), 7.18(1H, d, J=9.3 Hz).

6.3

2-[4-Chloro-2-fluoro-5-(3-trifluoromethyl-2-pyridyloxy) phenyl]-6,7-dihydropyrrolo[1,2-c]pyrimidine-1,3(2H,5H)-dione (Compound 5-10) (Process 1).

This was synthesized from 2-(4-chloro-2-fluoro-5-hydroxyphenyl)-6,7-dihydropyrrolo-[1,2-c]pyrimidine-1,3 (2H,5H)-dione and 2-chloro-3-trifluoromethylpyridine in 90% yield under similar conditions described below for the preparation of 2-[4-chloro-2-fluoro-5-(2-pyrimidyloxy) phenyl]hexabydro-3-thioxo-1H-[1,2,4]triazolo[1,2-a] pyridazin-1-one (Example 10.3) (compound (8-29).

Example 7

Synthesis of 1-[4-chloro-2-fluoro-5-(2-pyrimidyloxy)phenyl]-4-(3-fluoropropyl)-1,4-dihydro-5-oxo-5H-tetrazole (Compound 6-10) (Process 7).

7.1

1-[4-Chloro-2-fluoro-5-(2-pyrimidyloxy)phenyl]-1,4-dihydro-5-oxo-5H-tetrazole.

4-Chloro-$^2$-fluoro-5-(2-pyrimidyloxy)phenylisocyanate (0.96 g) and trimethylsilyl azide (5 ml) were heated at reflux overnight under nitrogen. The reaction mixture was processed and the resulting oil chromatographed on silica gel eluting with ethyl acetate:methylene chloride, 1:4, to give a yellow semi-solid (0.54 g). $^1$H NMR (CDCl$_3$, TMS): 7.16 (1H, dd, J=4.8 Hz), 7.49(1H, d, J=9.3 Hz), 7.64(1H, d, J=6.8 Hz), 8.59(2H, d, J=4.8 Hz).

7.2

1-[4-Chloro-2-fluoro-5-(2-pyrimidyloxy)phenyl]-4-(3-fluoropropyl)-1,4-dihydro-5-oxo-5H-tetrazole (Compound 6-10) (Process 1).

A suspension of potassium carbonate (0.36 g), 1-[4-chloro-2-fluoro-5-(2-pyrimidyloxy)phenyl]-1,4-dihydro-5-oxo-5H-tetrazole (0.54 g) and 1-bromo-3-fluoropropane (0.37 g) in N,N-dimethylformamide (10 ml) was stirred in an oil bath at 80° C. for 26 hours. The reaction mixture was processed and the resulting oil chromatographed on silica gel eluting with hexane:ethyl acetate, 2:1, to give the product, mp 111–3° C. $^1$H NMR (CDCl$_3$, TMS): 2.30(2H, m), 4.20(2H, t, J=6.9 Hz), 4.59(2H, dt, J=46.9, 6.6 Hz), 7.13(1H, dd, J=4.8 Hz), 7.48(1H, d, J=9.3 Hz), 7.58(1H, d, J=6.8 Hz), 8.58(2H, d, J=4.8 Hz).

Example 8

Synthesis of 9-[4-chloro-2-fluoro-5-(3-trifluoromethyl-2-pyridyloxy)phenylimino]-8-thia-1,6-diazabicyclo[4,3,0]nonane-7-one (Compound 7-1) (Process 8).

8.1

N-[4-Chloro-2-fluoro-5-(3-trifluoromethyl-2-pyridyloxy)phenylaminothiocarbonyl]-N$^1$-formylhydrazine.

Formic hydrazide (0.6 g) was added to a mixture of 4-chloro-2-fluoro-5-(3-trifluoromethyl-2-pyridyloxy)phenyl isothiocyanate (3.4 g) in tetrahydrofuran (20 ml) and the mixture was stirred for 3 hours at room temperature. The solvent was removed under reduced pressure and the residue processed. The resulting oil was dissolved in ethanol (30 ml), and hexane added to induce crystallization. The crystals were filtered and dried to give the product, (3.5 g, 69%).

8.2

5-[4-Chloro-2-fluoro-5-(3-trifluoromethyl-2-pyridyloxy)phenylimino]-3-formyl-1,3,4-thiadiazolidin-2-one.

Triphosgene (0.7 g) in toluene (20 ml) was dropwise added to a solution of N-[4-chloro-2-fluoro-5-(3-trifluoromethyl -2-pyridyloxy)phenylaminothiocarbonyl)-N$^1$-formyl-hydrazine (2.8 g) in acetone (70 ml) stirred at 0° C. Stirring was continued at room temperature for 1 hour and the solvents removed under reduced pressure. Column chromatography (methylene chloride:ethyl acetate, 3:1) yielded the product (3.3 g).

8.3

5-[4-Chloro-2-fluoro-5-(3-trifluoromethyl-2-pyridyloxy)phenylimino]-1,3,4-thiadiazol-idin-2-one.

A solution of 10% hydrochloric acid in methanol (8 ml) was added to a solution of 5-[4-chloro-2-fluoro-5-(3-trifluoromethyl-2-pyridyloxy)phenylimino]-3-formyl-1,3,4-thiadiazolidin-2-one (3.3 g) in acetone (60 ml). After stirring for 0.5 hour, the solvents were removed and the residue processed. A minimal amount of ethanol was used to dissolved the residue and hexane added to induce crystallization. The crystals were filtered off and dried to give the product (1.0 g, 36%).

8.4

9-[4-Chloro-2-fluoro-5-(3-trifluoromethyl-2-pyridyloxy)phenylimino]-8-thia-1,6-diazabicyclo[4,3,0]nonane-7-one (Compound 7-1).

1,4-Dibromobutane (0.64 g) was mixed with 5-[4-chloro-2-fluoro-5-(3-trifluoromethyl-2-pyridyloxy)phenylimino]-1,3,4-thiadiazolidin-2-one (1.0 g) in acetone (25 ml) and potassium carbonate (0.85 g) added. The mixture was heated at reflux for 2 hours and the solvent evaporated. The residue was processed and the resulting oil chromatographed (silica gel, hexane:ethyl acetate, 4:1) to give the product (0.65 g, 57%).

Example 9

Synthesis of 3-[4-chloro-2-fluoro-5-(trifluoromethyl-2-pyridyloxy)phenyl]-1-ethylimidazolidine-2,4-dione (Compound 8-1) (Process 9).

9.1

N-[4-Chloro-2-fluoro-5-(3-trifluoromethyl-2-pyridyloxy)phenyl]-2-chloroacetamide.

A solution of 2-(5-amino-2-chloro-4-fluorophenoxy)-3-trifluoromethylpyridine (1.32 g) and triethylamine (0.8 ml) in toluene (20 ml) was stirred at 0° C. while a solution of chloroacetyl chloride (0.4 ml) in toluene (10 ml) was added. The mixture was stirred over night at room temperature and processed. Column chromatography on silica gel using methylene chloride as eluent gave a white solid (1.4 g), mp 146–9° C. $^1$H NMR (CDCl$_3$, TMS): 4.20(2H, s), 7.12(1H, dd, J=5,8 Hz), 7.30(1H, d, J=9 Hz), 8.01(1H, m), 8.22(1H, m), 8.34(1H, d, J=7 Hz).

9.2

N-[4-Chloro-2-fluoro-5-(3-trifluoromethyl-2-pyridyloxy)phenyl]-2-ethylaminoacetamide.

A solution of N-[4-chloro-2-fluoro-5-(3-trifluoromethyl-2-pyridyloxy)phenyl]-2-chloroacetamide (1.4 g) and 70% ethylamine (5 ml) in ethanol (25 ml) was heated at reflux for 3 hours and evaporated to dryness. The residue was processed to give a yellow solid (1.0 g). $^1$H NMR (CDCl$_3$, TMS): 1.16(3H, t, J=7 Hz), 2.72(2H, q, J=7 Hz), 3.39(2H, s), 7.10(1H, dd, J=6,8 Hz), 7.26(1H, d, J=8 Hz), 8.00(1H, m), 8.24(1H, m), 8.45(1H, d, J=8 Hz), 9.86(1H, s).

9.3

3-[4-Chloro-2-fluoro-5-(trifluoromethyl-2-pyridyloxy)phenyl-1-ethylimidazolidine-2,4-dione (Compound 8-1).

A solution of N-[4-chloro-2-fluoro-5-(3-trifluoromethyl-2-pyridyloxy)phenyl]-2-ethylaminoacetamide (0.82 g) and 1,1$^1$-carbonyldiimidazole (0.43 g) in toluene (20 ml) was heated at reflux for 2 hours, cooled and processed. Column chromatography on silica gel eluting with 2.5% methanol-methylene chloride gave a buff colored solid (0.8 g), mp 162–3° C. $^1$H NMR (CDCl$_3$, TMS): 1.24(3H, t, J=7 Hz), 3.53(2H, q, J=7 Hz), 4.05(2H, s), 7.13(1H, m), 7.30(1H, d, J=7 Hz), 7.38(1H, d, J=9 Hz), 8.01(1H, m), 8.24(1H, m).

Example 10

Synthesis of 2-[4-chloro-2-fluoro-5-(2-pyrimidyloxy)phenyl]hexahydro-3-thioxo-1H-[1,2,4]triazolo[1,2-a]pyridazin-1-one (Compound 8-29). (Process 10).

10.1

2-[4-Chloro-2-fluoro-5-(isopropyloxy)phenyl]hexahydro-3-thioxo-1H-[1,2,4]triazolo[1,2-a]pyrdazin-1-one.

A solution of 4-chloro-2-fluoro-5-isopropyloxyaniline (12.1 g) and triethylamine (12.0 g) in ethyl acetate (120 ml) was cooled to 0° C. and stirred while a solution of thiophosgene (6.8 g) in ethyl acetate (100 ml) was added dropwise. The reaction was heated at reflux for 2 hours and the mixture filtered and the filtrate evaporated. The crude isothiocyanate was dissolved in benzene (70 ml) and treated with a solution of 1-ethyloxycarbonylhexahydropyridazine (9.5 g) in benzene (10 ml). After stirring for 3 hours the solvent was evaporated and the residue dissolved in m-xylene (250 ml) containing sodium acetate (1.6 g) and heated at reflux for 22 hours. The solvents were removed under reduced pressure and the residue chromatographed (silica gel, hexane:ethyl acetate, 60:40) to give the product (17.2 g, 81%). $^1$H NMR (CDCl$_3$, TMS): 1.37(6H, d, J=7.8 Hz), 1.96(4H, m), 3.71(2H, m), 4.02(2H, m), 4.47(1H, m), 6.95(1H, d, J=6.4 Hz), 7.30(1H, d, J=9.0 Hz).

10.2

2-(4-Chloro-2-fluoro-5-hydroxyphenyl)hexahydro-3-thioxo-1H-[1,2,4]triazolol[1,2-a]pyridazin-1-one.

Conc. sulfuric acid (22 ml) was added dropwise to a solution of 2-[4-chloro-2-fluoro-5-(isopropyloxy)phenyl]hexahydro-3-thioxo-1H-[1,2,4]triazolo[1,2-a]pyridazin-1-one (17.2 g) in methylene chloride (120 ml) stirred at 0° C. The mixture was stirred at room temperature for 1 hour and ice-water (200 g) added. The aqueous phase was extracted with methylene chloride and the organic phases combined, dried over sodium sulfate and chromatographed (silica gel, ethyl acetate) to give the product (14.5 g, 96%). $^1$H NMR (CDCl$_3$, TMS): 1.84(4H, m), 3.82(4H, m), 7.06(1H, d, J=6.5 Hz), 7.58(1H, d, J=8.8 Hz), 10.6(1H, s).

10.3

2-[4-Chloro-2-fluoro-5-(2-pyrimidyloxy)phenyl]hexahydro-3-thioxo-1H-[1,2,4]-triazolol[1,2-a]pyridazin-1-one (Compound 8-29).

2-(4-Chloro-2-fluoro-5-hydroxyphenyl)hexahydro-3-thioxo-1H-[1,2,4]triazolo-[1,2-a]pyridazin-1-one (0.5 g) was mixed with 2-chloropyrimidine (1 equiv) and potassium carbonate (2 equiv) in dimethylsulfoxide (20 ml) and the resulting mixture stirred at 100° C. for 1.5 hour and at room temperature overnight. The mixture was processed and the residue column chromatographed (silica gel, methylene chloride:ethyl acetate, 3:1) to give the product (0.34 g, 55%). $^1$H NMR (CDCl$_3$, TMS): 1.92(4H, m), 3.69(2H, m), 3.99(2H, m), 7.05(1H, m), 7.37(1H, d, J=6.5 Hz), 7.39(1H, d, J=9.0 Hz), 8.53(2H, d, J=4.8 Hz).

Example 11

Synthesis of 2-[4-chloro-2-fluoro-5-(3-trifluoromethyl-2-pyridyloxy)phenyl]hexahydro-3-thioxo-1H-[1,2,4]triazolo[1,2-a]pyridazin-1-one (Compound 8-18) (Process 11).

9-[4-Chloro-2-fluoro-5-(3-trifluoromethyl-2-pyridyloxy)phenylimino]-8-thia-1,6-diazabicyclo[4,3,0]nonan-7-one (see Example 8) (0.2 g) was mixed with methanol (18 ml) and a catalytic amount of sodium methoxide added. The mixture was heated at reflux for 0.5 hour and the solvent removed under reduced pressure. Column chromatography (silica gel, hexane:ethyl acetate, 3:2) yielded the product (0.2 g, 100%).

Example 12

(R,S)-2-[4-Chloro-2-fluoro-5-(2-pyrimidyloxy)phenyl]-hexahydro-3-thioxo-imidazo[1,5-a]pyridin-1(5H)-one (Compound 8-47) (Process 11).

Thiophosgene (0.192 g) was added to a solution of 4-chloro-2-fluoro-5-(2-pyrimidyloxy)aniline (0.4 g) and triethylamine (0.34 g) in dry ethyl acetate (10 ml) and the solution was heated under reflux for 1.5 hours. After cooling, the solution was filtered and the filtrate evaporated under reduced pressure. The residue was dissolved in dry ethyl acetate (10 ml) and ethyl pipecolinate (0.288 g) was added. The solution was heated under reflux for 1 hour and evaporated to give a brown solid. This was purified using column chromatography eluting with dichloromethane to give white crystals (0.35 g). mp 238–239° C.

The following were similarly prepared:

(R,S)-2-[4-Chloro-2-fluoro-5-(2-pyrimidyloxy)phenyl]-hexahydro-imidazo[1,5-a]pyridin-1,3-dione (Compound 8-48).

(S)-2-[4-Chloro-2-fluoro-5-(2-pyrimidyloxy)phenyl]-hexahydro-3-thioxo-imidazo[1,5-a]pyridin-1(5H)-one (Compound 8-49).

(S)-2-[4-Chloro-2-fluoro-5-(2-pyrimidyloxy)phenyl]-hexahydro-3-thioxo-pyrro[1,2-c]imidazol-1-(1H)-one (Compound 8-50).

(R,S)-2-(4-Chloro-2-fluoro-5-phenoxyphenyl)-hexahydro-3-thioxo-imidazo[1,5-a]pyridin-1(5H)-one (Compound 8-51).

(R,S)-2-[4-Chloro-2-fluoro-5-(2-nitrophenoxy)phenyl]-hexahydro-3-thioxo-imidazo[1,5-a]pyridin-1(5H)-one (Compound 8-52).

(R,S)-2-4-Chloro-5-(2-cyanophenoxy)-2-fluorophenyl]-hexahydro-3-thioxo-imidazo[1,5-a]pyridin-1(5H)-one (Compound 8-53).

(R,S)-2-[4-Chloro-2-fluoro-5-(2-pyrazinyloxy)phenyl]-hexahydro-3-thioxo-imidazo[1,5-a]pyridin-1(5H)-one (Compound 8-54).

(R,S)-2-[4-Chloro-2-fluoro-5-(2-pyridyloxy)phenyl]-hexahydro-3-thioxo-imidazo[1,5-a]pyridin-1(5H)-one (Compound 8-55).

(R,S)-2-[4-Chloro-5-(3-chloro-2-pyridyloxy)-2-fluorophenoxy]-hexahydro-3-thioxo-imidazo[1,5-a]pyridin-1(5H)-one (Compound 8-56).

(R,S)-2-[4-Chloro-5-(3-chloro-5-trifluoromethyl-2-pyridyloxy)-2-fluorophenyl]-hexahydro-3-thioxo-imidazo[1,5-a]pyridin-1(5H)-one (Compound 8-57).

(R,S)-2-[4-Chloro-2-fluoro-5-(3-trifluoromethyl-2-pyridyloxy)phenyl]-hexahydro-3-thioxo-imidazo[1,5-a]pyridin-1(5H)-one (Compound 8-58).

(R,S)-2-[4-Chloro-2-fluoro-5-(3-nitropyridyloxy)phenyl]-hexahydro-3-thioxo-imidazo[1,5-a]pyridin-1(5H)-one (Compound 8-59).

(R,S)-2-[4-Chloro-5-(3-cyano-2-pyridyloxy)-2-fluorophenyl]-hexahydro-3-thioxo-imidazo[1,5-a]pyridin-1(5H)-one (Compound 8-60).

Example 13

(R,S)-2-[5-(3-Amino-2-pyridyloxy)-4-chloro-2-fluorophenyl]-hexahydro-3-thioxo-imidazo[1,5-a]pyridin-1(5H)-one (Compound 8-61).

(R,S)-2-[4-Chloro-2-fluoro-5-(3-nitropyridyloxy)phenyl]-hexahydro-3-thioxo-imidazo[1,5-a]pyridin-1(5H)- one (0.21 g) dissolved in ethyl acetate (10 ml) was reduced under an atmosphere hydrogen using palladium-carbon (10%, 50 mg) as catalyst. After 5 hours stirring at room temperature the mixture was filtered and the filtrate evaporated under reduced pressure. The residue was purified by column chromatography eluting with dichloromethane:ethyl acetate, 9:1, to give a yellow oil (0.28 g).
The following was similarly prepared:
(R,S)-2-[5-(2-Aminophenoxy)-4-chloro-2-fluorophenyl]-hexahydro-3-thioxo-imidazo[1,5-a]pyridin-1(5H)-one (Compound 8-62).

Example 14

(R,S)-2-[5-(3-Acetylamino-2-pyridyloxy)-4-chloro-2-fuorophenyl]-hexahydro-3-thioxo-imidazo[1,5-a]pyridin-1(5H)-one (Compound 8-63).

Acetylchloride (0.047 g) was added to a solution of (R,S)-2-[5-(3-amino-2-pyridyloxy)-4-chloro-2-fluorophenyl]-hexahydro-3-thioxo-imidazo[1,5-a]pyridin-1 (5H)-one (0.22 g) and triethylamine (0.066 g) dissolved in dry ethyl acetate (10 ml) stirred at 5° C. The solution was stirred for 1 hour at a room temperature, filtered, and the filtrate evaporated. The residue was purified by column chromatography eluting with dichloromethane: ethyl acetate, 8:2 to give brown crystals (0.24 g).
The following was similarly prepared:
(R,S)-2-[5-[2-[(bis-Benzoyl)amino]phenoxy]4-chloro-2-fluorophenyl]-hexahydro-3-thioxo-imidazo[1,5-a]pyridin-1(5H)-one (Compound 8-64).

Example 15

Synthesis of 1-amino-3-[4-chloro-2-fluoro-5-(3-nitro-2-pyridyloxy)phenyl]-6-trifluoromethyl-1,2,3,4-tetrahydropyrimidine-2,4-dione (Compound 9-1).

15.1
Synthesis of 2-(5-amino-2-chloro-4-fluorophenoxy)-3-nitropyridine (Intermediate IIa) (Process 1).

A mixture of 5-amino-2-chloro-4-fluorophenol (0.64 g), powdered potassium hydroxide (0.24 g), and 2-chloro-3-nitropyridine (0.76 g) in dimethylsulfoxide (15 ml) was heated at 110° C. with stirring for 2 hours. The solution was processed and the resulting oil chromatographed on silica gel eluting with methanol:methylene chloride, 3:97, to yield 2-(5-amino-2-chloro-4-fluorophenoxy)-3-nitropyridine (Intermediate IIa) as a yellow semi-solid (0.45 g).
The following were similarly prepared:
2-(5-Amino-2-chloro-4-fluorophenoxy)-5-bromopyridine (Intermediate IIb).
2-(5-Amino-2-chloro-4-fluorophenoxy)-5-chloropyridine (Intermediate IIc).
2-(5-Amino-2-chloro-4-fluorophenoxy)-6-fluoropyridine (Intermediate IId).
2-(5-Amino-2-chloro-4-fluorophenoxy)-6-chloropyridine (Intermediate IIe).
2-(5-Amino-2-chloro-4-fluorophenoxy)-3,5,6-trifluoropyridine (Intermediate IIf).
2-(5-Amino-2-chloro-4-fluorophenoxy)-3-trifluoromethylpyridine (Intermediate IIg.
2-(5-Amino-2-chloro-4-fluorophenoxy)-4-trifluoromethylpyridine (Intermediate IIh).
2-(5-Amino-2-chloro-4-fluorophenoxy)-3-cyanopyridine (Intermediate IIi).
2-(5-Amino-2-chloro-4-fluorophenoxy)-5-cyanopyridine (Intermediate IIj).
2-(5-Amino-2-chloro-4-fluorophenoxy)-5-nitropyridine (Intermediate IIk).
2-(5-Amino-2,4-difluorophenoxy)-3-trifluoromethylpyridine (Intermediate Il).
2-(5-Amino-2-chloro-4-fluorophenoxy)-3-ethylsulfonylpyridine (Intermediate IIm).
5-(5-Amino-2-chloro-4-fluorophenoxy)-3-methyl-4-nitroisothiazole (Intermediate IIn).
2-(5-Amino-2-chloro-4-fluorophenoxy)pyridine (Intermediate IIo).

15.2
Synthesis of 3-[4-chloro-2-fluoro-5-(3-nitro-2-pyridyloxy)phenyl]-6-trifluoromethyl-1,2,3,4-tetrahydropyrimidine-2,4-dione (Intermediate 11-1) (Process 20).

A solution of triphosgene (0.47 g) in ethyl acetate (10 ml) was stirred under nitrogen while a solution 2-(5-amino-2-chloro-4-fluorophenoxy)-3-nitropyridine (0.45 g) and triethylamine (0.45 ml) in ethyl acetate (15 ml) was added dropwise. The mixture was heated at reflux for 2 hours, cooled, filtered, and the filtrate evaporated to give the corresponding isocyanate.

A suspension of sodium hydride (0.038 g) in N,N-dimethylformamide (2 ml) was stirred at 0° C. under nitrogen while a solution of ethyl 3-amino-4,4,4-trifluorocrotonate (0.26 g) in N,N-dimethylformamide (1 ml) was added dropwise. After 15 minutes a solution of the prepared isocyanate in N,N-dimethylformamide (5 ml) and toluene (5 ml) was added slowly and the solution stirred overnight at room temperature. Dilute hydrochloric acid was added and the solution processed. The resulting solid was chromatographed on silica gel eluting with methanol:methylene chloride, 5:95, to give 3-[4-chloro-2-fluoro-5-(3-nitro-2-pyridyloxy)phenyl]-6-trifluoromethyl-1,2,3,4-tetrahydropyrimidine-2,4-dione (Intermediate 11-1) as a white solid (0.32 g).
The following were similarly prepared:
3-[4-Chloro-2-fluoro-5-(5-bromo-2-pyridyloxy)phenyl]-6-trifluoromethyl-1,2,3,4-tetrahydropyrimidine-2,4-dione (Intermediate 11-2).
3-[4-Chloro-2-fluoro-5-(5-chloro-2-pyridyloxy)phenyl]-6-trifluoromethyl-1,2,3,4-tetrahydropyrimidine-2,4-dione (Intermediate 11-3).
3-[4-Chloro-2-fluoro-5-(6-fluoro-2-pyridyloxy)phenyl]-6-trifluoromethyl-1,2,3,4-tetrahydropyrimidine-2,4-dione (Intermediate 11-4).
3-[4-Chloro-2-fluoro-5-(6-chloro-2-pyridyloxy)phenyl]-6-trifluoromethyl-1,2,3,4-tetrahydropyrimidine-2,4-dione (Intermediate 11-5).
3-[4-Chloro-2-fluoro-5-(3,5,6-trifluoro-2-pyridyloxy)phenyl]-6-trifluoromethyl-1,2,3,4-tetrahydropyrimidine-2,4-dione (Intermediate 11-6).
3-[4-Chloro-2-fluoro-5-(3-trifluoromethyl-2-pyridyloxy)phenyl]-6-trifluoromethyl-1,2,3,4-tetrahydropyrimidine-2,4-dione (Intermediate 11-7).
3-[4-Chloro-2-fluoro-5-(4-trifluoromethyl-2-pyridyloxy)phenyl]-6-trifluoromethyl-1,2,3,4-tetrahydropyrimidine-2,4-dione (Intermediate 11-8).
3-[4-Chloro-2-fluoro-5-(3-cyano-2-pyridyloxy)phenyl]-6-trifluoromethyl-1,2,3,4-tetrahydropyrimidine-2,4-dione (Intermediate 11-9).
3-[4-Chloro-2-fluoro-5-(5-cyano-2-pyridyloxy)phenyl]-6-trifluoromethyl-1,2,3,4-tetrahydropyrimidine-2,4-dione (Intermediate 11-10).
3-[4-Chloro-2-fluoro-5-(5-nitro-2-pyridyloxy)phenyl]-6-trifluoromethyl-1,2,3,4-tetrahydropyrimidine-2,4-dione (Intermediate 11-11).

3-[2,4-Difluoro-5-(3-trifluoromethyl-2-pyridyloxy)phenyl]-6-trifluoromethyl-1,2,3,4-tetrahydropyrimidine-2,4-dione (Intermediate 11-12).

3-[4-Chloro-2-fluoro-5-(3-ethylsulfonyl-2-pyridyloxy)phenyl]-6-trifluoromethyl-1,2,3,4-tetrahydropyrimidine-2,4-dione (Intermediate 11-13).

3-[4-Chloro-2-fluoro-5-(3-methyl-4-nitro-5-isothiazolyloxy)phenyl]-6-trifluoromethyl-1,2,3,4-tetrahydropyrimidine-2,4-dione(Intermediate 11-14).

3-[4-Chloro-2-fluoro-5-(4-chloro-2-pyrimidyloxy)phenyl]-6-trifluoromethyl-1,2,3,4-tetrahydropyrimidine-2,4-dione (Intermediate 11-16).

3-[4-Chloro-2-fluoro-5-(4,6-dimethoxy-2-pyrimidyloxy)phenyl]-6-trifluoromethyl-1,2,3,4-tetrahydropyrimidine-2,4-dione (Intermediate 11-17).

15.3
Synthesis of 1-amino-3-[4-chloro-2-fluoro-5-(3-nitro-2-pyridyloxy)phenyl]-6-trifluoromethyl-1,2,3,4-tetrahydropyrimidine-2,4-dione (Compound 9-1) (Process 15).

A suspension of potassium carbonate (0.23 g), 3-[4-chloro-2-fluoro-5-(3-nitro-2-pyridyloxy)phenyl]-6-trifluoromethyl-1,2,3,4-tetrahydropyrimidine-2,4-dione (0.5 g) and 2,4-dinitrophenoxyamine (0.32 g) in N,N-dimethylformamide (10 ml) was stirred at room temperature overnight. The solution was processed and the resulting oil chromatographed on silica gel eluting with methanol:methylene chloride, 2:98. The product was isolated as a yellow semi-solid (0.3 g), mp 90–6° C.

The following were similarly prepared:

1-Amino-3-[4-chloro-2-fluoro-5-(5-bromo-2-pyridyloxy)phenyl]-6-trifluoromethyl-1,2,3,4-tetrahydropyrimidine-2,4-dione (Compound 9-2).

1-Amino-3-[4-chloro-2-fluoro-5-(5-chloro-2-pyridyloxy)phenyl]-6-trifluoromethyl-1,2,3,4-tetrahydropyrimidine-2,4-dione (Compound 9-3).

1-Amino-3-[4-chloro-2-fuoro-5-(6-fluoro-2-pyridyloxy)phenyl]-6-trifluoromethyl-1,2,3,4-tetrahydropyrimidine-2,4-dione (Compound 9-4).

1-Amino-3-[4-chloro-2-fluoro-5-(6-chloro-2-pyridyloxy)phenyl]-6-trifluoromethyl-1,2,3,4-tetrahydropyrimidine-2,4-dione (Compound 9-5).

1-Amino-3-[4-chloro-2-fluoro-5-(3,5,6-trifluoro-2-pyridyloxy)phenyl]-6-trifluoromethyl-1,2,3,4-tetrahydropyrimidine-2,4-dione (Compound9-6).

1-Amino-3-[4-chloro-2-fluoro-5-(3-trifluoromethyl-2-pyridyloxy)phenyl]-6-trifluoromethyl-1,2,3,4-tetrahydropyrimidine-2,4-dione (Compound 9-7).

1-Amino-3-[4-chloro-2-fluoro-5-(4-trifluoromethyl-2-pyridyloxy)phenyl]-6-trifluoromethyl-1,2,3,4-tetrahydropyrimidine-2,4-dione (Compound 9-8).

1-Amino-3-[4-chloro-2-fluoro-5-(3-cyano-2-pyridyloxy)phenyl]-6-trifluoromethyl-1,2,3,4-tetrahydropyrimidine-2,4-dione (Compound 9-9).

1-Amino-3-[4-chloro-2-fluoro-5-(5-cyano-2-pyridyloxy)phenyl]-6-trifluoromethyl-1,2,3,4-tetrahydropyrimidine-2,4-dione (Compound 9-10).

1-Amino-3-[4-chloro-2-fluoro-5-(5-nitro-2-pyridyloxy)phenyl]-6-trifluoromethyl-1,2,3,4-tetrahydropyrimidine-2,4-dione (Compound 9-11).

1-Amino-3-[2,4-difluoro-5-(3-trifluoromethyl-2-pyridyloxy)phenyl]-6-trifluoromethyl-1,2,3,4-tetrahydropyrimidine-2,4-dione (Compound 9-12).

1-Amino-3-[4-Chloro-2-fluoro-5-(3-ethylsulfonyl-2-pyridyloxy)phenyl]-6-trifluoromethyl-1,2,3,4-tetrahydropyrimidine-2,4-dione (Compound 9-13).

1-Amino-3-[4-Chloro-2-fluoro-5-(3-methyl-4-nitroisothiazol-5-yloxy)phenyl]-6-trifluoromethyl-1,2,3,4-tetrahydropyrimidine-2,4-dione (Compound 9-14).

1-Amino-3-[4-chloro-2-fluoro-5-(2-pyrimidyloxy)phenyl]-6-trifluoromethyl-1,2,3,4-tetrahydropyrimidine-2,4-dione (Compound 9-16).

1-Amino-3-[4-chloro-2-fluoro-5-(4-chloro-2-pyrimidyloxy)phenyl]-6-trifluoromethyl-1,2,3,4-tetrahydropyrimidine-2,4-dione (Compound 9-17).

1-Amino-3-[4-chloro-2-fluoro-5-(4,6-dimethoxy-2-pyrimidyloxy)phenyl]-6-trifluoromethyl-1,2,3,4-tetrahydropyrimidine-2,4-dione (Compound 9-18).

Example 16

Synthesis of 1-amino-3-[4-chloro-2-fluoro-5-(2-pyridyloxy)phenyl]-6-trifluoromethyl-1,2,3,4-tetrahydropyrimidine-2,4-dione (Compound 9-15) (Process 16).

A solution of triphosgene (0.5 g) in ethyl acetate (10 ml) was stirred under nitrogen while a solution of 2-(5-amino-2-chloro-4-fluorophenoxy)pyridine (0.4 g) and triethylamine (0.5 ml) in ethyl acetate (20 ml) was added dropwise. The mixture was heated at reflux for 2 hours, cooled, filtered, and evaporated to give the corresponding isocyanate.

A suspension of sodium hydride (0.05 g) in N,N-dimethylformamide (2 ml) was stirred at 0° C. under nitrogen while a solution of ethyl 3-amino-4,4,4-trifluorocrotonate (0.32 g) in N,N-dimethylfonnamide (1 ml) was added dropwise. After 15 minutes a solution of the prepared isocyanate in N,N-dimethylformamide (5 ml) and toluene (5 ml) was added slowly. The solution was stirred at room temperature for 2 hours and treated with a solution of 2,4-dinitrophenoxyamine (0.42 g) in N,N-dimethylformamide (4 ml). Stirring was continued for 3 days. The solution was processed and gave a solid which was chromatographed on silica gel cluting with methanol:methylene chloride, 5:95. The title compound was obtained as a yellow solid (0.3 g).

The following were similarly prepared:

1-Amino-3-[4-chloro-2-fluoro-5-(3-nitro-2-pyridyloxy)phenyl]-6-trifluoromethyl-1,2,3,4-tetrahydropyrimidine-2,4-dione (Compound 9-1).

1-Amino-3-[4-chloro-2-fluoro-5-(5-chloro-2-pyridyloxy)phenyl]-6-trifluoromethyl-1,2,3,4-tetrahydropyrimidine-2,4-dione (Compound 9-3).

Example 17

Synthesis of 1-amino-3-[4-chloro-2-fluoro-5-(2-nitrophenoxy)phenyl]-6-trifluoromethyl-1,2,3,4-tetrahydropyrimidine-2,4-dione (Compound 9-21).

17.1
3-[4-Chloro-2-fluoro-5-(2-nitrophenoxy)phenyl]-6-trifluoromethyl-1,2,3,4-tetrahydropyrimidine-2,4-dione (Intermediate 11-18) (Process 18).

A mixture of 3-(4-chloro-2-fluoro-5-hydroxyphenyl)-6-trifluoromethyl-1,2,3,4-tetrahydropyrimidine-2,4-dione (2.2 g), 2-chloronitrobenzene (1.3 g) and potassium carbonate (1.4 g) in N,N-dimethylformamide (100 ml) was heated at reflux for 3 hours under an atmosphere of nitrogen. The resulting mixture was poured into water (200 ml) and acidified by the addition of a small portion of conc. hydrochloric acid. The solution was extracted with a mixed solvent (ethyl acetate:hexane, 1:1, 400 ml) and the organic phase dried over anhydrous sodium sulfate. The solvent was removed under reduced pressure and the residue chromatographed on silica gel eluting with ethyl acetate:hexane, 1:1, to give 3-[4-chloro-2-fluoro-5-(2-nitrophenoxy)phenyl]-6-trifluoromethyl-1,2,3,4-tetrahydropyrimidine-2,4-dione (Intennediate 11-18) as an amorphous solid (1.0-g).

The following were similarly prepared:

3-[4-Chloro-2-fluoro-5-(3-methylsulfonyl-2-pyridyloxy)phenyl]-6-trifluoromethyl-1,2,3,4-tetrahydropyrimidine-2,4-dione (Intermediate 11-19).

3-[4-Chloro-2-fluoro-5-(3-isopropylsulfonyl-2-pyridyloxy)phenyl]-6-trifluoromethyl-1,2,3,4-tetrahydropyrimidine-2,4-dione (Intermediate 11-20).

3-[4-chloro-2-fluoro-5-(4-nitrophenoxy)phenyl]-6-trifluoromethyl-1,2,3,4-tetrahydropyrimidine-2,4-dione (Intermediate 11-21)

3-[4-Chloro-2-fluoro-5-(4-nitro-2-trifluoromethylphenoxy)phenyl]-6-trifluoromethyl-1,2,3,4-tetrahydropyrimidine-2,4-dione (Intermediate 11-22).

3-[4-Chloro-2-fluoro-5-(3-nitro-5-trifluoromethylphenoxy)phenyl]-6-trifluoromethyl-1,2,3,4-tetrahydropyrimidine-2,4-dione (Intermediate 11-23).

3-[4-Chloro-2-fluoro-5-(2-cyanophenoxy)phenyl]-6-trifluoro-methyl-1,2,3,4-tetrahydropyrimidine-2,4-dione (Intermediate 11-33).

3-[4-Chloro-2-fluoro-5-(2-cyano-3-fluorophenoxy)phenyl]-6-trifluoromethyl-1,2,3,4-tetrahydropyrimidine-2,4-dione (Intermediate 11-34).

17.2

1-Amino-3-[4-chloro-2-fluoro-5-(2-nitrophenoxy)phenyl]-6-trifluoromethyl-1,2,3,4-tetrahydropyrimidine-2,4-dione (Compound 9-21) (Process 15).

A suspension of 3-[4-chloro-2-fluoro-5-(2-nitrophenoxy)phenyl]-6-trifluoro-methyl-1,2,3,4-tetrahydropyrimidine-2,4,-dione (1.0 g), potassium carbonate (0.37 g), and 2,4-dinitrophenoxyamine (0.54 g) in anhydrous N,N-dimethylformamide (20 ml) was stirred at room temperature for 20 hours. The solution was processed and the resulting oil was chromatographed on silica gel eluting with methylene chloride:hexane:ethyl acetate, 2:3:0.5. The product was crystallized from methylene chloride:hexane:ethyl acetate to give a white solid (0.45 g).

The following were similarly prepared:

1-Amino-3-[4-chloro-2-fluoro-5-(3-methylsulfonyl-2-pyridyloxy)phenyl]-6-trifluoromethyl-1,2,3,4-tetrahydropyrimidine-2,4-dione (Compound 9-19).

1-Amino-3-[4-chloro-2-fluoro-5-(3-isopropylsulfonyl-2-pyridyloxy)phenyl]-6-trifluoromethyl-1,2,3,4-tetrahydropyrimidine-2,4-dione (Compound 9-20).

1-Amino-3-[4-chloro-2-fluoro-5-(4-nitro-2-trifluoromethylphenoxy)phenyl]-6-trifluoromethyl-1,2,3,4-tetrahydropyrimidine-2,4-dione (Compound 9-22).

1-Amino-3-[4-chloro-2-fluoro-5-(3-nitro-5-trifluoromethylphenoxy)phenyl]-6-trifluoromethyl-1,2,3,4-tetrahydropyrimidine-2,4-dione (Compound 9-23).

1-Amino-3-[4-chloro-2-fluoro-5-(2-cyanophenoxy)phenyl]-6-trifluoromethyl-1,2,3,4-tetrahydropyrimidine-2,4-dione (Compound 9-30).

1-Amino-3-[4-chloro-2-fluoro-5-(2-cyano-3-fluorophenoxy)phenyl]-6-trifluoro-methyl-1,2,3,4-tetrahydropyrimidine-2,4-dione (Compound 9-31).

Example 18

Synthesis of 1-amino-3-[4-chloro-2-fluoro-5-(2-trifluoromethylphenoxy)phenyl]-6-trifluoromethyl-1,2,3,4-tetrahydropyrimidine-2,4-dione (Compound 9-24).

18.1

3-[4-Chloro-2-fluoro-5-(4-amino-2-trifluoromethylphenoxy)phenyl]-6-trifluoromethyl-1,2,3,4-tetrahydropyrimidine-2,4-dione (Intermediate 11-24).

A suspension of 10% Pd/C and 3-[4-chloro-2-fluoro-5-(4-nitro-2-trifluoromethylphenoxy)phenyl]-6-trifluoromethyl-1,2,3,4-tetrahydropyrimidine-2,4-dione (4.0 g) in ethyl acetate (100 ml) was stirred overnight under an atmosphere of hydrogen. The mixture was filtered through Celite and the filtrate concentrated. The resulting oil was chromatographed on silica gel eluting with ethyl acetate:hexane, 1:0.8. 3-[4-Chloro-2-fluoro-5-(4-amino-2-trifluoromethylphenoxy)phenyl]-6-trifluoromethyl-1,2,3,4-tetrahydropyrimidine-2,4-dione (Intermediate 11-24) was isolated as an amorphous solid (3.3 g).

The following were similarly prepared:

3-[4-Chloro-2-fluoro-5-(4-aminophenoxy)phenyl]-6-trifluoromethyl-1,2,3,4-tetrahydropyrimidine-2,4-dione (Intermediate 11-25).

3-[4-Chloro-2-fluoro-5-(3-amino-5-trifluoromethylphenoxy)phenyl]-6-trifluoro-methyl-1,2,3,4-tetrahydropyrimidine-2,4-dione (Intermediate 11-26).

3-[4-Chloro-2-fluoro-5-(2-aminophenoxy)phenyl]-6-trifluoromethyl-1,2,3,4-tetrahydropyrimidine-2,4-dione (Intermediate 11-27).

18.2

3-[4-Chloro-2-fluoro-5-(2-trifluoromethylphenoxy)phenyl]-6-trifluoromethyl-1,2,3,4-tetrahydropyrimidine-2,4-dione (Intermediate 11-28).

3-[4-Chloro-2-fluoro-5-(4-amino-2-trifluoromethylphenoxy)phenyl]-6-trifluoromethyl-1,2,3,4-tetrahydropyrimidine-2,4-dione (3.0 g) dissolved in anhydrous N,N-dimethylformamide (10 ml) was added to a solution of t-butyl nitrite (1.28 g) in anhydrous N,N-dimethylformamide (40 ml) kept at 60–5° C. under nitrogen. The resulting mixture was stirred for 30 minutes at this temperature. The solution was poured into water and extracted with ethyl acetate: hexane, 1:1, (300 ml). The organic phase was washed with brine and dried over anhydrous sodium sulfate. After removal of the solvent, the residue was chromatographed on silica gel eluting with ethyl acetate:hexane, 1:2. 3-[4-Chloro-2-fluoro-5-(2-trifluoromethylphenoxy)phenyl]-6-trifluoromethyl-1,2,3,4-tetrahydropyrimid-ine-2,4-dione (Intermediate 11-28) was isolated as an amorphous solid (1.64 g).

The following were similarly prepared:

3-[4-Chloro-2-fluoro-5-(3-trifluoromethylphenoxy)phenyl]-6-trifluoromethyl-1,2,3,4-tetrahydropyrimidine-2,4-dione (Intermediate 11-29).

3-[4-Chloro-2-fluoro-5-phenoxyphenyl]-6-trifluoromethyl-1,2,3,4-tetrahydropyrimidine-2,4-dione (Intermediate 11-30).

18.3

1-Amino-3-[4-chloro-2-fluoro-5-(2-trifluoromethylphenoxy)phenyl]-6-trifluoromethyl-1,2,3,4-tetrahydropyrimidine-2,4-dione (Compound 9-24) (Process 15).

A suspension of 3-[4-chloro-2-fluoro-5-(2-trifluoromthylphenoxy)phenyl]-6-trifluoromethyl-1,2,3,4- tetrahydropyrimidine-2,4,-dione (0.7 g), potassium carbonate (0.27 g) and 2,4-dinitrophenoxyamine (0.39 g) in anhydrous N,N-dimethylformamide (20 ml) was stirred at room temperature for 72 hours. The solution was processed and the resulting oil chromatographed on silica gel eluting with hexane:ethyl acetate, 4:1, containing 0.1% of triethylamine. The product (Compound 9-24) was isolated as a pale yellow amorphous solid (0.6 g).

The following were similarly prepared:
- 1-Amino-3-[4-chloro-2-fluoro-5-(3-trifluoromethylphenoxy)phenyl]-6-trifluoro-methyl-1,2,3,4-tetrahydropyrimidine-2,4-dione (Compound 9-25).
- 1-Amino-3-[4-chloro-2-fluoro-5-phenoxyphenyl-6-trifluoromethyl-1,2,3,4-tetrahydropyrimidine-2,4-dione (Compound 9-26).

Example 19

Synthesis of ethyl 2-[4-[2-chloro-4-fluoro-5-(1-amino-6-trifluoromethyl-1,2,3,4-tetrahydropyrimidine-2,4-dion-3yl)phenoxy]phenoxy]propionate (Compound 9-27).

19.1
3-[4-Chloro-2-fluoro-5-(4-hydroxyphenoxy)phenyl]-6-trifluoromethyl-1,2,3,4-tetrahydropyrimidine-2,4-dione (Intermediate 11-31).

3-[4-Chloro-2-fluoro-5-(4-aminophenoxy)phenyl]-6-trifluoromethyl-1,2,3,4-tetrahydro-pyrimidine-2,4-dione (2.0 g) was mixed with hot 30% sulfuric acid (5 ml) and ic/water (5.0 g) was added. The mixture kept at 10° C. while a solution of sodium nitrite (0.45 g) in water (5 ml) was slowly introduced at the bottom of the stirred mixture. After stirring for 10 minutes, urea (0.1 g) was added, followed by a solution of copper(2)nitrate (18.0 g) in water (170 ml), and copper(1)oxide (0.7 g). The mixture was stirred for 10 minutes, extracted with diethyl ether (50 ml×3), and dried over sodium sulfate. The crude product was purified by column chromatography (hexane:ethyl acetate, 4:1) to give 3-[4-chloro-2-fluoro-5-(4-hydroxyphenoxy)phenyl]-6-trifluoromethyl-1,2,3,4-tetrahydropyrimidine-2,4-dione (Intermediate 11-31), (1.0 g).

19.2
Ethyl 2-[4-[2-chloro-4-fluoro-5-(6-trifluoromethyl-1,2,3,4-tetrahydropyrimidine-2,4-dion-3yl)phenoxy]phenoxy]propionate (Intermediate 11-32).

A solution of 3-[4-chloro-2-fluoro-5-(4-hydroxyphenoxy)phenyl]-6-trifluoro-methyl-1,2,3,4-tetrahydropyrimidine-2,4-dione (1.0 g) in butan-2-one (20 ml) was mixed with ethyl 2-bromopropionate (1 equivalent) and potassium carbonate (1 equivalent) and heated at reflux for 4 hours. The mixture was filtered and evaporated. The crude product was chromatographed to give ethyl 2-[4-[2-chloro-4-fluoro-5-(6-trifluoromethyl-1,2,3,4-tetrahydropyrimidine-2,4-dion-3-yl)phenoxy]phenoxy]propionate (Intermediate 11-32) (0.81 g).

19.3
Ethyl 2-[4-[2-chloro-4-fluoro-5-(1-amino-6-trifluoromethyl-1,2,3,4-tetrahydropyrimidine-2,4-dion-3yl)phenoxy]phenoxy]propionate (Compound 9-27) (Process 15).

A suspension of ethyl 2-[4-[2-chloro4-fluoro-5-(4-trifluoromethyl-1,2,3,6-tetrahydropyrimidine-2,6-dion-3yl)phenoxy]phenoxy]propionate (0.81 g), potassium carbonate (0.24 g) and 2,4-dinitrophenoxyamine (0.35 g) in anhydrous N,N-dimethylformamide (20 ml) was stirred at room temperature for 24 hours. The solution was processed and the resulting oil chromatographed on silica gel eluting with hexane ethyl acetate, 4:1. The product, ethyl 2-[4-[2-chloro-4-fluoro-5-(1-amino-6-trifluoromethyl-1,2,3,4-tetrahydropyrimidine-2,4-dion-3-yl)phenoxy]phenoxy]propionate (Compound 9-27) was isolated as a pale yellow amorphous solid (0.51 g).

Example 20

Synthesis of 1-amino-3-[4-chloro-2-fluoro-5-(5-chloro-2-pyridyloxy)phenyl]-6-trifluoromethyl-1,2,3,4-tetrahydro-2-oxo-4-thioxopyrimidine (Compound 9-28) (Process 17).

A mixture of 1-amino-3-[4-chloro-2-fluoro-5-(5-chloro-2-pyridyloxy)phenyl]-6-trifluoromethyl-1,2,3,4-tetrahydropyrimidine-2,4-dione (0.27 g), sodium bicarbonate (0.19 g) and Lawessons' reagent (0.26 g) in dry toluene (10 ml) was heated at reflux for 4 hours. The mixture was cooled, filtered, and the residue evaporated under reduced pressure. The resulting oil was chromatographed on silica gel eluting with ethyl acetate:hexane, 4:6, to give a yellow viscous oil (0.18 g).

The following were similarly prepared.
- 1-Amino-3-[4-chloro-2-fluoro-5(3-nitro-2-pyridyloxy)phenyl]-6-trifluoromethyl-1,2,3,4-tetrahydropyrimidine-2-oxo-4-thioxopyrimidine (Compound 9-29).

Example 21

Synthesis of 1-amino-3-[4-chloro-2-fluoro-5-(3-nitro-2-pyridyloxy)phenyl]-6-trifluoromethyl-1,2,3,4-tetrahydropyrimidine-2,4-dione (Compound 9-1).

21.1
1-Amino-3-(4-chloro-2-fluoro-5-isopropyloxyphenyl)-6-trifluoromethyl-1,2,3,4-tetrahydropyrimidine-2,4-dione.

A suspension of sodium hydride (1.0 g, 60% in oil) in N,N-dimethylformamide (30 ml) was stirred at 0° C. under nitrogen while a solution of ethyl 3-amino-4,4,4-trifluorocrotonate (4.5 g) in N,N-dimethylformamide (20 ml) was added dropwise. After stirring for 15 minutes, a solution of 4-chloro-2-fluoro-5-isopropyloxyphenylisocyanate (5.6 g) in toluene (25 ml) was added slowly at −35° C. The solution was stirred at room temperature for 2 hours and treated with a solution of 2,4-dinitrophenoxyamine (5.8 g) in N,N-dimethylformamide (20 ml). Stirring was continued for 3 days. The solution was processed and gave a solid which was chromatographed on silica gel eluting with ethyl acetate:hexane, 1:5, containing 0.1% of triethylamine. 1-Amino-3-(4-chloro-2-fluoro-5-isopropyloxyphenyl)-6-trifluoromethyl-1,2,3,4-tetrahydropyrimidine-2,4-dione was obtained as a white solid (5.3 g).

21.2
1-Amino-3-(4-chloro-2-fluoro-5-hydroxyphenyl)-6-trifluoromethyl-1,2,3,4-tetrahydropyrimidine-2,4-dione.

Conc. sulfuric acid (3 ml) was added to a solution of 1-amino-3-(4-chloro-2-fluoro-5-isopropyloxyphenyl)-6-trifluoromethyl-1,2,3,4-tetrahydropyrimidine-2,4-dione (4.5 g) in methylene chloride (50 ml) stirred at 0° C. . After 1 hour the mixture was diluted with water and processed. The oily product was chromatographed on silica gel eluting with ethyl acetate:hexane, 2:3, to give 1-amino-3-(4-chloro-2-fluoro-5-hydroxyphenyl)-6-trifluoromethyl-1,2,3,4-tetrahydropyrimidine-2,4-dione as a pale yellow amorphous solid (3.6 g,). $^1$H NMR (CDCl$_3$, TMS): 7.27(1H, d, J=8.8 Hz), 6.88(1H, d, J=6.5 Hz), 6.28(1H, s), 5.86(1H, br. s), 4.61(2H, s)

21.3

1-Amino-3-[4-chloro-2-fluoro-5-(3-nitro-2-pyridyloxy)phenyl]-6-trifluoromethyl-1,2,3,4-tetrahydropyrimidine-2,4-dione (Compound 9-1) (Process 14).

Sodium hydride (75 mg, 60% in oil) was added at room temperature to a mixture of 1-amino-3-(4-chloro-2-fluoro-5-hydroxyphenyl)-6-trifluoromethyl-1,2,3,4-tetrahydropyrimidine-2,4-dione (0.5 g) and 2-chloro-3-nitropyridine (0.35 g) in anhydrous tetrahydrofuran (50 ml). After stirring for 36 hours water was added and the reaction mixture processed. Chromatography on silica gel eluting with ethyl acetate:hexane, 1:2, gave compound 9-1 as a yellow semi-solid (0.1 g).

The following compounds may be similarly prepared:

1-Amino-3-[4-chloro-2-fluoro-5-(5-trifuoromethyl-2-pyridyloxy)phenyl]-6-trifluoromethyl-1,2,3,4-tetrahydropyrimidine-2,4-dione (Compound 9-32).

1-Amino-3-[2,4-dichloro-5-(5-trifluoromethyl-2-pyridyloxy)phenyl]-6-trifluoromethyl-1,2,3,4-tetrahydropyrimidine-2,4-dione (Compound 9-33).

1-Amino-3-[2,4-difluoro-5-(5-trifluoromethyl-2-pyridyloxy)phenyl]-6-trifluoromethyl-1,2,3,4-tetrahydropyrimidine-2,4-dione (Compound 9-34).

1-Amino-3-[4-chloro-5-(5-trifluoromethyl-2-pyridyloxy)phenyl]-6-trifluoromethyl-1,2,3,4-tetrahydropyrimidine-2,4-dione (Compound 9-35).

1-Amino-3-[4-bromo-2-fluoro-5-(5-trifluoromethyl-2-pyridyloxy)phenyl]-6-trifluoromethyl-1,2,3,4-tetrahydropyrimidine-2,4-dione (Compound 9-36).

1-Amino-3-[4-bromo-5-(5-trifluoromethyl-2-pyridyloxy)phenyl]-6-trifluoromethyl-1,2,3,4-tetrahydropyrimidine-2,4-dione (Compound 9-37).

1-Amino-3-[4-chloro-2-fluoro-5-(3-amino-2-pyridyloxy)phenyl]-6-trifluoro-methyl-1,2,3,4-tetrahydropyrimidine-2,4-dione (Compound 9-38).

1-Amino-3-[4-chloro-2-fluoro-5-(3-aminotrifluoroacetyl-2-pyridyloxy)phenyl]-6-trifluoromethyl-1,2,3,4-tetrahydropyrimidine-2,4-dione (Compound 9-39).

1-Amino-3-[4-chloro-2-fluoro-5-(3-aminoacetyl-2-pyridyloxy)phenyl]-6-trifluoro-methyl-1,2,3,4-tetrahydropyrimidine-2,4-dione (Compound 9-40).

1-Amino-3-[4-chloro-2-fluoro-5-(3-aminomethylsulfonate-2-pyridyloxy)phenyl]6-trifluoromethyl-1,2,3,4-tetrabydropyrimidine-2,4-dione (Compound 9-41).

1-Amino-3-[4-chloro-2-fluoro-5-(3-chloro-2-pyridyloxy)phenyl]-6-trifluoromethyl-1,2,3,4-tetrahydropyrimidine-2,4-dione (Compound 9-42).

1-3-[4-chloro-2-fluoro-5-(6-bromo-2-pyridyloxy)phenyl]-6-trifluoromethyl-1,2,3,4-tetrahydropyrimidine-2,4-dione (Compound 9-43).

1-Amino-3-[4-chloro-2-fluoro-5-(5-chloro-3-trifluoromethyl-2-pyridyloxy)phenyl]-6-trifluoromethyl-1,2,3,4-tetrahydropyrimidine-2,4-dione (Compound 9-44).

1-Amino-3-[4-chloro-2-fluoro-5-(3-nitro-5-trifluoromethyl-2-pyridyloxy)phenyl]6-trifluoromethyl-1,2,3,4-tetrahydropyrimidine-2,4-dione (Compound 9-45).

1-Amino-3-4-chloro-2-fluoro-5-(3-chloro-5-trifluoromethyl-2-pyridyloxy)phenyl]-6-trifluoromethyl-1,2,3,4-tetrabydropyrimidine-2,4-dione (Compound 9-46).

1-Amino-3-[4-chloro-2-fluoro-5-(3,5-dichloro-2-pyridyloxy)phenyl]-6-trifluoro-methyl-1,2,3,4-tetrahydropyrimidine-2,4-dione (Compound 9-47).

1-Amino-3-[4-chloro-2-fluoro-5-(3,5-dinitro-2-pyridyloxy)phenyl]-6-trifluoro-methyl-1,2,3,4-tetrahydropyrimidine-2,4-dione (Compound 9-48).

1-Amino-3-[4-chloro-2-fluoro-5-(4,6-bistrifluoromethyl-2-pyridyloxy)phenyl]-6-trifluoromethyl-1,2,3,4-tetrahydropyrimidine-2,4-dione (Compound 9-49).

1-Amino-3-[4-chloro-2-fluoro-5-(6-chloro-4-cyano-2-pyridyloxy)phenyl]-6-trifluoromethyl-1,2,3,4-tetrahydropyrimidine-2,4-dione (Compound 9-50).

1-Amino-3-[4-chloro-2-fluoro-5-(4,5-bistrifluoromethyl-2-pyridyloxy)phenyl]-6-trifluoromethyl-1,2,3,4-tetrahydropyrimidine-2,4-dione (Compound 9-51).

1-Amino-3-[4-chloro-2-fluoro-5-(3,6-bistrifluoromethyl-2-pyridyloxy)phenyl]-6-trifluoromethyl-1,2,3,4-tetrahydropyrimidine-2,4-dione (Compound 9-52).

1-Amino-3-[4-chloro-2-fluoro-5-(3,5,6-trichloro-4-trifluoromethyl-2-pyridyloxy)-phenyl]-6-trifluoromethyl-1,2,3,4-tetrahydropyrimidine-2,4-dione (Compound 9-53).

1-Amino-3-[4-chloro-2-fluoro-5-(3,4,5-trichloro-6-trifluoromethyl-2-pyridyloxy)-phenyl]-1-methyl-6-trifluoromethyl-2,4-(1H,3H)-pyrimidinedione (Compound 9-54).

1-Amino-3-[4-chloro-2-fluoro-5-(3,5-dichloro-4,6-difluoro-2-pyridyloxy)phenyl]-6-trifluoromethyl-1,2,3,4-tetrahydropyrimidine-2,4-dione (Compound 9-55).

1-Amino-3-[4-chloro-2-fluoro-5-(3,5,6-trifluoro-4-bromo-2-pyridyloxy)phenyl]-6-trifluoromethyl-1,2,3,4-tetrahydropyrimidine-2,4-dione (Compound 9-56).

1-Amino-3-[4-chloro-2-fluoro-5-(3,4,5,6-tetrachloro-2-pyridyloxy)phenyl]-6-trifluoromethyl-1,2,3,4-tetrahydropyrimidine-2,4-dione (Compound 9-57).

1-Amino-3-[4-chloro-2-fluoro-5-(5-bromo-2-pyrimidyloxy)phenyl]-6-trifluoro-methyl-1,2,3,4-tetrahydropyrimidine-2,4-dione (Compound 9-58).

1-Amino-3-[4-chloro-2-fluoro-5-(6-chloro-5-nitro-4-pyrimidyloxy)phenyl]-6-trifluoromethyl-1,2,3,4-tetrahydropyrimidine-2,4-dione (Compound 9-59).

1-Amino-3-[4-chloro-2-fluoro-5-(6-chloro-2-pyridazinyloxy)phenyl]-6-trifluoro-methyl-1,2,3,4-tetrahydropyrimidine-2,4-dione (Compound 9-60).

1-Amino-3-[4-chloro-2-fluoro-5-(2-chloro-6-nitrophenoxy)phenyl]-6 -trifluoromethyl-1,2,3,4-tetrahydropyrimidine-2,4-dione (Compound 9-61).

1-Amino-3-[4-chloro-2-fluoro-5-(4-fluoro-6-nitrophenoxy)phenyl]-6-trifluoromethyl-1,2,3,4-tetrahydropyrimidine-2,4-dione (Compound 9-62).

1-Amino-3-[4-chloro-2-fluoro-5-(3-fluoro-6-nitrophenoxy)phenyl]-6-trifluoromethyl-1,2,3,4-tetrahydropyrimidine-2,4-dione (Compound 9-63).

1-Amino-3-[4-chloro-2-fluoro-5-(3-fluoro-2-nitrophenoxy)phenyl]-6-trifluoromethyl-1,2,3,4-tetrahydropyrimidine-2,4-dione (Compound 9-64).

1-Amino-3-[4-chloro-2-fluoro-5-(2-fluorophenoxy)phenyl]-6-trifluoromethyl-1,2,3,4-trahydropyrimidine-2,4-dione (Compound 9-65).

1-Amino-3-[4-chloro-2-fluoro-5-(3-fluorophenoxy)phenyl]-6-trifluoromethyl-1,2,3,4-tetrahydropyrimidine-2,4-dione (Compound 9-66).

1-Amino-3-[4-chloro-2-fluoro-5-(4-fluorophenoxy)phenyl]-6-trifuoromethyl-1,2,3,4-tetrahydropyrimidine-2,4-dione (Compound 9-67).

1-Amino-3-[4-chloro-2-fluoro-5-(2-chloro-4-nitrophenoxy)phenyl]-6-trifluoromethyl-1,2,3,4-tetrahydropyrimidine-2,4-dione (Compound 9-68).

1-Amino-3-[4-chloro-2-fluoro-5(4-cyano-2,3,5,6-tetrafluorophenoxy)phenyl]-6-trifluoromethyl-1,2,3,4-tetrahydropyrimidine-2,4-dione (Compound 9-69).

1-Amino-3-[4-chloro-2-fluoro-5-(3-chloro-4,6-dinitrophenoxy)phenyl]-6-trifluoromethyl-1,2,3,4-tetrahydropyrimidine-2,4-dione (Compound 9-70).

1-Amino-3-[4-chloro-2-fluoro-5-(4-nitrophenoxy)phenyl]-6-trifluoromethyl-1,2,3,4-tetrahydropyrimidine-2,4-dione (Compound 9-71).

1-Amino-3-[4-chloro-2-fluoro-5-(6-chloro-3-pyridazinyloxy)-phenyl]-6-trifluoro-methyl-1,2,3,4-tetrahydropyrimidine-2,4-dione (Compound 9-72).

Some of the compounds of the present invention produced by the methods described above are shown in Tables 1–9. The physical data on intermediates including the NMR data is shown in Tables 10 and 11. The NMR data of compounds of the present invention are shown in Table 12.

TABLE 1

Examples of formula (I)

| Compound No. | Ar | X | Y | Z | $R_1$ | $Q_1$ $R_2$ | $R_3$ | Physical Properties |
|---|---|---|---|---|---|---|---|---|
| 1-1 | 3-nitro-2-pyridyl | F | Cl | O | Cl | $CF_3$ | $CH_3$ | |
| 1-2 | 3-trifluoromethyl-2-pyridyl | F | Cl | O | Cl | $CF_3$ | $CH_3$ | |
| 1-3 | 3-cyano-2-pyridyl | F | Cl | O | Cl | $CF_3$ | $CH_3$ | |
| 1-4 | 5-cyano-2-pyridyl | F | Cl | O | Cl | $CF_3$ | $CH_3$ | |
| 1-5 | 6-fluoro-2-pyridyl | F | Cl | O | Cl | $CF_3$ | $CH_3$ | |
| 1-6 | 3,5,6-trifluoro-2-pyridyl | F | Cl | O | Cl | $CF_3$ | $CH_3$ | |
| 1-7 | 2-pyrimidyl | F | Cl | O | Cl | $CF_3$ | $CH_3$ | |
| 1-8 | 4,6-dimethoxy-2-triazinyl | F | Cl | O | Cl | $CF_3$ | $CH_3$ | |
| 1-9 | phenyl | CN | $NO_2$ | S | Br | $CH_3$ | $C_2H_5$ | |

TABLE 2

Examples of formula (I)

| Compound No. | Ar | X | Y | Z | $R_1$ | $Q_2$ $R_2$ | $R_3$ | Physical Properties |
|---|---|---|---|---|---|---|---|---|
| 2-1 | 3-nitro-2-pyridyl | F | Cl | O | Cl | $CF_3$ | $CH_3$ | |
| 2-2 | 3-trifluoromethyl-2-pyridyl | F | Cl | O | Cl | $CF_3$ | $CH_3$ | |
| 2-3 | 2-pyrimidyl | F | Cl | O | Cl | $CF_3$ | $CH_3$ | |
| 2-4 | 4,6-dimethoxy-2-triazinyl | F | Cl | O | Cl | $CHF_2$ | $CH_3$ | |
| 2-5 | 2-nitrophenyl | $CF_3$ | F | S | Br | $C_2H_5$ | $n\text{-}C_3H_7$ | |

TABLE 3

Examples of formula (I)

| Compound No. | Ar | X | Y | Z | $R_2$ | $Q_3$ $R_3$ | Physical Properties |
|---|---|---|---|---|---|---|---|
| 3-1 | 2-pyrimidyl | F | Cl | O | $CH_3$ | $CHF_2$ | |

TABLE 4

Examples of formula (I)

| Compound No. | Ar | X | Y | Z | $R_3$ | $Q_4$ $R_5$ | $R_4$ | Physical Properties |
|---|---|---|---|---|---|---|---|---|
| 4-1 | 3-trifluoromethyl-2-pyridyl | F | Cl | O | H | $CH_3$ | $CH_3$ | |
| 4-2 | 3-trifluoromethyl-2-pyridyl | F | Cl | O | —$CH_2CH_2CH_2$— | | H | |
| 4-3 | phenyl | $NO_2$ | $CF_3$ | S | —$CH_2CH_2$— | | $C_2H_5$ | |

TABLE 5

Examples of formula (I)

| Compound No. | Ar | X | Y | Z | Q5 | Physical Properties |
|---|---|---|---|---|---|---|
| 5-1 | 2-nitrophenyl | F | Cl | O | $Q_5$ | |
| 5-2 | 4-nitrophenyl | F | Cl | O | $Q_5$ | |
| 5-3 | 4-aminophenyl | F | Cl | O | $Q_5$ | |
| 5-4 | 4-hydroxyphenyl | F | Cl | O | $Q_5$ | |
| 5-5 | 4-methylsulfonylaminophenyl | F | Cl | O | $Q_5$ | |
| 5-6 | 4-(1-ethoxycarbonylethoxy)phenyl | F | Cl | O | $Q_5$ | |
| 5-7 | 3-chloro-2- | F | Cl | O | $Q_5$ | |
| 5-8 | 3-nitro-2-pyridyl | F | Cl | O | $Q_5$ | |
| 5-9 | 3-cyano-2-pyridyl | F | Cl | O | $Q_5$ | |
| 5-10 | 3-trifluoromethyl-2-pyridyl | F | Cl | O | $Q_5$ | |
| 5-11 | 5-cyano-2-pyridyl | F | Cl | O | $Q_5$ | |
| 5-12 | 2-pyrimidyl | F | Cl | O | $Q_5$ | |
| 5-13 | 5-nitro-2-thiazolyl | $CF_3$ | $NO_2$ | S | $Q_5$ | |
| 5-14 | 3-methyl-4-cyano-5-isothiazolyl | CN | H | S | $Q_5$ | |

TABLE 6

Examples of formula (I)

| Compound No. | Ar | X | Y | Z | $Q_6$ $R_6$ | Physical Properties |
|---|---|---|---|---|---|---|
| 6-1 | 2-pyridyl | F | Cl | O | $CH_2CH_2CH_2F$ | |
| 6-2 | 3-nitro-2-pyridyl | F | Cl | O | $CH_2CH_2CH_2F$ | |
| 6-3 | 3-nitro-2-pyridyl | Cl | Cl | O | $CH_2CH_2CH_2F$ | |
| 6-4 | 3-cyano-2-pyridyl | F | Cl | O | $CH_2CH_2CH_2F$ | |
| 6-5 | 3-cyano-2-pyridyl | Cl | Cl | O | $CH_2CH_2CH_2F$ | |
| 6-6 | 3-trifluoromethyl-2-pyridyl | F | Cl | O | $CH_2CH_2CH_2F$ | |
| 6-7 | 3-trifluoromethyl-2-pyridyl | Cl | Cl | O | $CH_2CH_2CH_2F$ | |
| 6-8 | 5-trifluoromethyl-2-pyridyl | F | Cl | O | $CH_2CH_2CH_2F$ | |
| 6-9 | 5-trifluoromethyl-2-pyridyl | Cl | Cl | O | $CH_2CH_2CH_2F$ | |
| 6-10 | 2-pyrimidyl | F | Cl | O | $CH_2CH_2CH_2F$ | m.p. 111–3° C. |
| 6-11 | 2-pyrimidyl | F | Cl | O | $CH_2CH_3$ | |
| 6-12 | 2-pyrimidyl | F | Cl | O | $CH_2CH_2OCH_3$ | |
| 6-13 | 2-pyrimidyl | F | Cl | O | $CH_2CH_2CN$ | |
| 6-14 | 2-pyrimidyl | Cl | Cl | O | $CH_2CH_2CH_2F$ | |
| 6-15 | 4-6-dimethoxy-2-pyrimidyl | F | Cl | O | $CH_2CH_2CH_2F$ | |
| 6-16 | 5-bromo-2-pyrimidyl | F | Cl | O | $CH_2CH_2CH_2F$ | |
| 6-17 | 3-methyl-4-nitro-5-isothiazolyl | F | Cl | O | $CH_2CH_2CH_2F$ | |
| 6-18 | phenyl | Cl | F | S | $CH_2C \equiv CBr$ | |

TABLE 7

Examples of formula (I)

| Compound No. | Ar | X | Y | Z | $Q_5$ | Physical Properties |
|---|---|---|---|---|---|---|
| 7-1 | 3-trifluoromethyl-2-pyrimidyl | F | Cl | O | $Q_7$ | |
| 7-2 | 2-pyrimidyl | F | Cl | O | $Q_7$ | |
| 7-3 | phenyl | CN | $NO_2$ | S | $Q_7$ | |

TABLE 8

Examples of formula (I)

| Compound No. | Ar | X | Y | Z | $Q_8$ | | | | | Physical Properties |
|---|---|---|---|---|---|---|---|---|---|---|
| | | | | | $A_1$ | $A_2$ | B | $R_7$ | $R_8$ | |
| 8-1 | 3-trifluoromethyl-2-pyridyl | F | Cl | O | O | O | CH | $CH_2CH_3$ | H | |
| 8-2 | 2-pyrimidyl | F | Cl | O | O | O | CH | $CH_2CH_3$ | H | |
| 8-3 | 2-pyrimidyl | F | Cl | O | O | O | CH | $CH_3$ | H | |
| 8-4 | 3-trifluoromethyl-2-pyridyl | F | Cl | O | O | O | CH | —$(CH_2)_4$— | | |
| 8-5 | phenyl | F | Cl | O | S | O | N | —$(CH_2)_4$— | | |
| 8-6 | 2-nitrophenyl | F | Cl | O | S | O | N | —$(CH_2)_4$— | | |
| 8-7 | 2-cyanophenyl | F | Cl | O | S | O | N | —$(CH_2)_4$— | | |
| 8-8 | 4-nitrophenyl | F | Cl | O | S | O | N | —$(CH_2)_4$— | | |
| 8-9 | 4-aminophenyl | F | Cl | O | S | O | N | —$(CH_2)_4$— | | |
| 8-10 | 4-hydroxyphenyl | F | Cl | O | S | O | N | —$(CH_2)_4$— | | |
| 8-11 | 4-(1-ethoxycarbonylethoxy)phenyl | F | Cl | O | S | O | N | —$(CH_2)_4$— | | |
| 8-12 | 2-cyano-4-nitrophenyl | F | Cl | O | S | O | N | —$(CH_2)_4$— | | |

TABLE 8-continued

Examples of formula (I)

| Compound No. | Ar | X | Y | Z | $A_1$ | $A_2$ | B | $Q_8$ $R_7$ | $R_8$ | Physical Properties |
|---|---|---|---|---|---|---|---|---|---|---|
| 8-13 | 4-amino-2-cyanophenyl | F | Cl | O | S | O | N | —(CH$_2$)$_4$— | | |
| 8-14 | 4-nitro-2-trifluoromethylphenyl | F | Cl | O | S | O | N | —(CH$_2$)$_4$— | | |
| 8-15 | 4-amino-2-trifluoromethylphenyl | F | Cl | O | S | O | N | —(CH$_2$)$_4$— | | |
| 8-16 | 4-acetylamino-2-trifluoromethylphenyl | F | Cl | O | S | O | N | —(CH$_2$)$_4$— | | |
| 8-17 | 2-pyridyl | F | Cl | O | S | O | N | —(CH$_2$)$_4$— | | |
| 8-18 | 3-trifluoromethyl-2-pyridyl | F | Cl | O | S | O | N | —(CH$_2$)$_4$— | | |
| 8-19 | 3-nitro-2-pyridyl | F | Cl | O | S | O | N | —(CH$_2$)$_4$— | | |
| 8-20 | 3-cyano-2-pyridyl | F | Cl | O | S | O | N | —(CH$_2$)$_4$— | | |
| 8-21 | 3-methylsulfonyl-2-pyridyl | F | Cl | O | S | O | N | —(CH$_2$)$_4$— | | |
| 8-22 | 5-cyano-2-pyridyl | F | Cl | O | S | O | N | —(CH$_2$)$_4$— | | |
| 8-23 | 5-nitro-2-pyridyl | F | Cl | O | S | O | N | —(CH$_2$)$_4$— | | |
| 8-24 | 5-amino-2-pyridyl | F | Cl | O | S | O | N | —(CH$_2$)$_4$— | | |
| 8-25 | 6-fluoro-2-pyridyl | F | Cl | O | S | O | N | —(CH$_2$)$_4$— | | |
| 8-26 | 6-chloro-2-pyridyl | F | Cl | O | S | O | N | —(CH$_2$)$_4$— | | |
| 8-27 | 3-trifluoromethyl-6-chloro-2-pyridyl | F | Cl | O | S | O | N | —(CH$_2$)$_4$— | | |
| 8-28 | 3,5,6-trifluoro-2-pyridyl | F | Cl | O | S | O | N | —(CH$_2$)$_4$— | | |
| 8-29 | 2-pyrimidyl | F | Cl | O | S | O | N | —(CH$_2$)$_4$— | | |
| 8-30 | 4-trifluoromethyl-2-pyrimidyl | F | Cl | O | S | O | N | —(CH$_2$)$_4$— | | |
| 8-31 | 4-chloro-2-pyrimidyl | F | Cl | O | S | O | N | —(CH$_2$)$_4$— | | |
| 8-32 | 2,6-dimethoxy-4-pyrimidyl | F | Cl | O | S | O | N | —(CH$_2$)$_4$— | | |
| 8-33 | 4,6-dimethoxy-2-pyrimidyl | F | Cl | O | S | O | N | —(CH$_2$)$_4$— | | |
| 8-34 | 4,6-dimethoxy-2-triazinyl | F | Cl | O | S | O | N | —(CH$_2$)$_4$— | | |
| 8-35 | 3-methyl-4-nitro-5-isothiazolyl | F | Cl | O | S | O | N | —(CH$_2$)$_4$— | | |
| 8-36 | 5-nitro-2-thiazolyl | F | Cl | O | S | O | N | —(CH$_2$)$_4$— | | |
| 8-37 | 3-isopropylsulfonyl-2-pyridyl | F | Cl | O | S | O | N | —(CH$_2$)$_4$— | | |
| 8-38 | 5-chloro-4-(1-ethoxycarbonylethoxy)-2-nitrophenyl | F | Cl | O | S | O | N | —(CH$_2$)$_4$— | | |
| 8-39 | 4-(1-ethoxycarbonylethoxy)-2-nitrophenyl | F | Cl | O | S | O | N | —(CH$_2$)$_4$— | | |
| 8-40 | 2-amino-4-(1-ethoxycarbonylethoxy)-phenyl | F | Cl | O | S | O | N | —(CH$_2$)$_4$— | | |
| 8-41 | 4-(1-ethoxycarbonylethoxy)-2-nitrophenyl | F | Cl | O | S | O | N | —(CH$_2$)$_4$— | | |
| 8-42 | 3-amino-2-pyridyl | F | Cl | O | S | O | N | —(CH$_2$)$_4$— | | |
| 8-43 | 3-methylthio-2-pyridyl | F | Cl | O | S | O | N | —(CH$_2$)$_4$— | | |

TABLE 8-continued

Examples of formula (I)

| Compound No. | Ar | X | Y | Z | A₁ | A₂ | B | R₇ | R₈ | Physical Properties |
|---|---|---|---|---|---|---|---|---|---|---|
| 8-44 | 3-dimethyl-aminocarbonyl-2-pyridyl | Br | Cl | S | O | O | N | —(CH₂)₃— | | |
| 8-45 | 2-pyrimidyl | NO₂ | CF₃ | S | O | O | N | —(CH₂)₃— | | |
| 8-46 | phenyl | CF₃ | CN | S | O | O | N | C₂H₅ | C₂H₅ | |
| 8-47 | 2-pyrimidyl | F | Cl | O | S | O | CH | —(CH₂)₄— | | (R, S) |
| 8-48 | 2-pyrimidyl | F | Cl | O | O | O | CH | —(CH₂)₄— | | (R, S) |
| 8-49 | 2-pyrimidyl | F | Cl | O | S | O | CH | —(CH₂)₄— | | (S) |
| 8-50 | 2-pyrimidyl | F | Cl | O | S | O | CH | —(CH₂)₄— | | (S) |
| 8-51 | phenyl | F | Cl | O | S | O | CH | —(CH₂)₄— | | (R, S) |
| 8-52 | 2-nitrophenyl | F | Cl | O | S | O | CH | —(CH₂)₄— | | (R, S) |
| 8-53 | 2-cyanophenyl | F | Cl | O | S | O | CH | —(CH₂)₄— | | (R, S) |
| 8-54 | 2-pyrazinyl | F | Cl | O | S | O | CH | —(CH₂)₄— | | (R, S) |
| 8-55 | 2-pyridyl | F | Cl | O | S | O | CH | —(CH₂)₄— | | (R, S) |
| 8-56 | 3-chloro-2-pyridyl | F | Cl | O | S | O | CH | —(CH₂)₄— | | (R, S) |
| 8-57 | 3-chloro-2-trifluoromethyl-2-pyridyl | F | Cl | O | S | O | CH | —(CH₂)₄— | | (R, S) |
| 8-58 | 3-trifluoromethyl-2-pyridyl | F | Cl | O | S | O | CH | —(CH₂)₄— | | (R, S) |
| 8-59 | 3-nitro-2-pyridyl | F | Cl | O | S | O | CH | —(CH₂)₄— | | (R, S) |
| 8-60 | 3-cyano-2-pyridyl | F | Cl | O | S | O | CH | —(CH₂)₄— | | (R, S) |
| 8-61 | 3-amino-2-pyridyl | F | Cl | O | S | O | CH | —(CH₂)₄— | | (R, S) |
| 8-62 | 2-aminophenyl | F | Cl | O | S | O | CH | —(CH₂)₄— | | (R, S) |
| 8-63 | 3-acetylamino-2-pyridyl | F | Cl | O | S | O | CH | —(CH₂)₄— | | (R, S) |
| 8-64 | 2-(bisbenzoyl)-aminophenyl | F | Cl | O | S | O | CH | —(CH₂)₄— | | (R, S) |

TABLE 9

Examples of Formula (1).

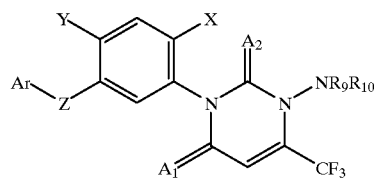

(Q₉)

| Compd. No. | Ar | X | Y | Z | A₁ | A₂ | R₉ | R₁₀ | Physical property |
|---|---|---|---|---|---|---|---|---|---|
| 9-1 | 3-nitro-2-pyridyl | F | Cl | O | O | O | H | H | mp 90–96 |
| 9-2 | 5-bromo-2-pyridyl | F | Cl | O | O | O | H | H | mp 69–70 |
| 9-3 | 5-chloro-2-pyridyl | F | Cl | O | O | O | H | H | amorphous |
| 9-4 | 6-fluoro-2-pyridyl | F | Cl | O | O | O | H | H | amorphous |
| 9-5 | 6-chloro-2-pyridyl | F | Cl | O | O | O | H | H | amorphous |
| 9-6 | 3,5,6-trifluoro-2-pyridyl | F | Cl | O | O | O | H | H | amorphous |
| 9-7 | 3-trifluoromethyl-2-pyridyl | F | Cl | O | O | O | H | H | amorphous |
| 9-8 | 4-trifluoromethyl-2-pyridyl | F | Cl | O | O | O | H | H | amorphous |
| 9-9 | 3-cyano-2-pyridyl | F | Cl | O | O | O | H | H | amorphous |
| 9-10 | 5-cyano-2-pyridyl | F | Cl | O | O | O | H | H | amorphous |
| 9-11 | 5-nitro-2-pyridyl | F | Cl | O | O | O | H | H | amorphous |
| 9-12 | 3-trifluoromethyl-2-pyridyl | F | F | O | O | O | H | H | amorphous |
| 9-13 | 3-ethylsulfonyl-2-pyridyl | F | Cl | O | O | O | H | H | mp 277–279 |
| 9-14 | 3-methyl-4-nitro-5-isothiazolyl | F | Cl | O | O | O | H | H | amorphous |
| 9-15 | 2-pyridyl | F | Cl | O | O | O | H | H | amorphous |
| 9-16 | 2-pyrimidyl | F | Cl | O | O | O | H | H | white solid |
| 9-17 | 4-chloro-2-pyrimidyl | F | Cl | O | O | O | H | H | amorphous |
| 9-18 | 4,6-dimethoxy-2-pyrimidyl | F | Cl | O | O | O | H | H | amorphous |

TABLE 9-continued

Examples of Formula (1).

(Q₉)

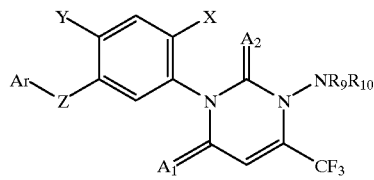

| Compd. No. | Ar | X | Y | Z | A₁ | A₂ | R₉ | R₁₀ | Physical property |
|---|---|---|---|---|---|---|---|---|---|
| 9-19 | 3-methylsulfonyl-2-pyridyl | F | Cl | O | O | O | H | H | mp 276–278 |
| 9-20 | 3-isopropylsulfonyl-2-pyridyl | F | Cl | O | O | O | H | H | mp 155–158 |
| 9-21 | 2-nitrophenyl | F | Cl | O | O | O | H | H | mp 155–158 |
| 9-22 | 4-nitro-2-trifluoromethylphenyl | F | Cl | O | O | O | H | H | amorphous |
| 9-23 | 3-nitro-5-trifluoromethylphenyl | F | Cl | O | O | O | H | H | amorphous |
| 9-24 | 2-trifluoromethylphenyl | F | Cl | O | O | O | H | H | amorphous |
| 9-25 | 3-trifluoromethylphenyl | F | Cl | O | O | O | H | H | amorphous |
| 9-26 | phenyl | F | Cl | O | O | O | H | H | amorphous |
| 9-27 | 4-(1-ethoxycarbonylethoxy)-phenyl | F | Cl | O | O | O | H | H | amorphous |
| 9-28 | 5-chloro-2-pyridyl | F | Cl | O | S | O | H | H | amorphous |
| 9-29 | 3-nitro-2-pyridyl | F | Cl | O | S | O | H | H | amorphous |
| 9-30 | 2-cyanophenyl | F | Cl | O | O | O | H | H | mp 220–222 |
| 9-31 | 2-cyano-3-fluorophenyl | F | Cl | O | O | O | H | H | mp 230–233 |
| 9-32 | 5-trifluoromethyl-2-pyridyl | F | Cl | O | O | O | H | H | |
| 9-33 | 5-trifluoromethyl-2-pyridyl | Cl | Cl | O | O | O | H | H | |
| 9-34 | 5-trifluoromethyl-2-pyridyl | F | F | O | O | O | H | H | |
| 9-35 | 5-trifluoromethyl-2-pyridyl | H | Cl | O | O | O | H | H | |
| 9-36 | 5-trifluoromethyl-2-pyridyl | F | Br | O | O | O | H | H | |
| 9-37 | 5-trifluoromethyl-2-pyridyl | H | Br | O | O | O | H | H | |
| 9-38 | 3-amino-2-pyridyl | F | Cl | O | O | O | H | H | |
| 9-39 | 3-aminotrifluoroacetyl-2-pyridyl | F | Cl | O | O | O | H | H | |
| 9-40 | 3-aminoacetyl-2-pyridyl | F | Cl | O | O | O | H | H | |
| 9-41 | 3-aminomethylsulfonate-2-pyridyl | F | Cl | O | O | O | H | H | |
| 9-42 | 3-chloro-2-pyridyl | F | Cl | O | O | O | H | H | |
| 9-43 | 6-bromo-2-pyridyl | F | Cl | O | O | O | H | H | |
| 9-44 | 5-chloro-3-trifluoromethyl-2-pyridyl | F | Cl | O | O | O | H | H | |
| 9-45 | 3-nitro-5-trifluoromethyl-2-pyridyl | F | Cl | O | O | O | H | H | |
| 9-46 | 3-chloro-5-trifluoromethyl-2-pyridyl | F | Cl | O | O | O | H | H | |
| 9-47 | 3,5-dichloro-2-pyridyl | F | Cl | O | O | O | H | H | |
| 9-48 | 3,5-dinitro-2-pyridyl | F | Cl | O | O | O | H | H | |
| 9-49 | 4,6-bistrifluoromethyl-2-pyridyl | F | Cl | O | O | O | H | H | |
| 9-50 | 6-chloro-4-cyano-2-pyridyl | F | Cl | O | O | O | H | H | |
| 9-51 | 4,5-bistrifluoromethyl-2-pyridyl | F | Cl | O | O | O | H | H | |
| 9-52 | 3,6-bistrifluoromethyl-2-pyridyl | F | Cl | O | O | O | H | H | |
| 9-53 | 3,5,6-trichloro-4-trifluoromethyl-2-pyridyl | F | Cl | O | O | O | H | H | |
| 9-54 | 3,4,5-trichloro-6-trifluoromethyl-2-pyridyl | F | Cl | O | O | O | H | H | |
| 9-55 | 1,3,5-dichloro-4,6-difluoro-2-pyridyl | F | Cl | O | O | O | H | H | |
| 9-56 | 4-bromo-3,5,6-trifluoro-2-pyridyl | F | Cl | O | O | O | H | H | |
| 9-57 | 3,4,5,6-tetrachloro-2-pyridyl | F | Cl | O | O | O | H | H | |
| 9-58 | 5-bromo-2-pyrimidyl | F | Cl | O | O | O | H | H | |
| 9-59 | 6-chloro-5-nitro-4-pyrimidyl | F | Cl | O | O | O | H | H | |
| 9-60 | 6-chloro-4-pyridazinyl | F | Cl | O | O | O | H | H | |
| 9-61 | 2-chloro-6-nitrophenyl | F | Cl | O | O | O | H | H | |
| 9-62 | 4-fluoro-6-nitrophenyl | F | Cl | O | O | O | H | H | |
| 9-63 | 3-fluoro-6-nitrophenyl | F | Cl | O | O | O | H | H | |
| 9-64 | 3-fluoro-2-nitrophenyl | F | Cl | O | O | O | H | H | |
| 9-65 | 2-fluorophenyl | F | Cl | O | O | O | H | H | |
| 9-66 | 3-fluorophenyl | F | Cl | O | O | O | H | H | |
| 9-67 | 4-fluorophenyl | F | Cl | O | O | O | H | H | |
| 9-68 | 2-chloro-4-nitrophenyl | F | Cl | O | O | H | H | | |
| 9-69 | 4-cyano-2,3,5,6-tetrafluoro-phenyl | F | Cl | O | O | O | H | H | |
| 9-70 | 3-chloro-4,6-dinitrophenyl | F | Cl | O | O | O | H | H | |

TABLE 9-continued

Examples of Formula (1).

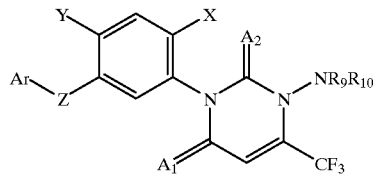

(Q$_9$)

| Compd. No. | Ar | X | Y | Z | A$_1$ | A$_2$ | R$_9$ | R$_{10}$ | Physical property |
|---|---|---|---|---|---|---|---|---|---|
| 9-71 | 4-nitrophenyl | F | Cl | O | O | O | H | H | |
| 9-72 | 6-chloro-3-pyridazinyl | F | Cl | O | O | O | H | H | |

TABLE 10

Examples of Intermediate (II), (III), and (XX)

| Intermediate No. | Ar | Y | X | Z | Physical property | $^1$H NMR (CDCl$_3$) |
|---|---|---|---|---|---|---|
| IIa | 3-nitro-2-pyridyl | Cl | F | O | amorphous | 3.93(2H, s), 6.67(1H, d, J=8.2Hz), 7.08(1H, d, J=10.5Hz), 7.18(1H, dd, J=7.9, 4.8Hz), 8.31(1H, dd, J=4.8, 1.8Hz), 8.38(1H, dd, J=7.9, 1.8Hz). |
| IIb | 5-bromo-2-pyridyl | Cl | F | O | brown solid | 3,80(2H, br s), 6.62(1H, d, J=7.Hz), 6.87(1H, d, J=8.7Hz), 7.71(1H, d, J=10.4Hz), 7.77(1H, dd, J=8.7, 2.5Hz), 8.18(1H, d, J=2.5Hz). |
| IIc | 5-chloro-2-pyridyl | Cl | F | O | colorless crystals | 3.83(2H, br s), 5.61(1H, d, J=8.3Hz), 6.90(1H, d, J=8.7Hz), 7.10(1H, d, J=10.4Hz), 7.64(1H, m), 808(1H, m). |
| IId | 6-fluoro-2-pyridyl | Cl | F | O | amorphous | 3.81(2H, br s), 6.60(1H, dd, J=2.7, 8.0Hz), 6.63(1H, d, J=8.2Hz), 6.75(1H, dd, J=1.2, 7.7 Hz), 7.09(1H, d, J=10.4Hz), 7.76(1H, dd, J=8.0, 15.9Hz). |
| IIe | 6-chloro-2-pyridyl | Cl | F | O | mp 114–116 | 3.80(2H, br s), 6.64(1H, d, J=8.3Hz), 6.77(1H, d, J=8.1Hz), 7.05(2H, m), 7.61(1H, m). |
| IIf | 3, 5, 6-trifluoro-2-pyridyl | Cl | F | O | amorphous | 3.83(2H, br s), 6.64(1H, d, J=8.1Hz), 7.10(1H, d, J=10.2Hz), 7.51(1H, m). |
| IIg | 3-trifluoromethyl-2-pyridyl | Cl | F | O | crystals | 3.78(2H, br), 6.64(1H, d, J=8.2Hz), 7.09(1H, m), 7.09(1H, d, J=10.3Hz), 7.99(1H, m), 8.26(1H, m). |
| IIh | 4-trifluoromethyl-2-pyridyl | Cl | F | O | mp 73–74 | 3.83(2H, m), 6.64(1H, d, J=8.2Hz), 7.12(1H, d, J=10.3Hz), 7.20(2H, m), 8.29(1H, d, J=5.2Hz); |
| IIi | 3-cyano-2-pyridyl | Cl | F | O | amorphous | 3.85(2H, br s), 6.69(1H, d, J=8.2Hz), 7.12(1H, dd, J=7.6, 5.0Hz), 7.12(1H, d, J=10.9Hz), 8.02(1H, dd, J=1.9, 7.6Hz), 8.31(1H, dd, J=1.9, 5.0Hz). |
| IIj | 5-cyano-2-pyridyl | Cl | F | O | amorphous | 3.69(2H, br s), 6.67(1H, d, J=8.2Hz), 7.07(1H, d, J=8.6Hz), 7.12(1H, d, J=10.4Hz), 7.98(1H, dd, J=2.3, 8.7Hz), 8.45(1H, d, J=2.3Hz). |
| IIk | 5-nitro-2-pyridyl | Cl | F | O | amorphous | 3.89(2H, br s), 6.65(1H, d, J=8.2Hz), 7.08(1H, d, J=9.5Hz), 7.13(1H, d, J=10.4Hz), 8.50(1H, dd, J=2,8, 9.0Hz), 9.02(1H, d, J=2.8Hz). |
| IIl | 3-trifluoromethyl-2-pyridyl | F | F | O | amorphous | 3.65(2H, br s), 6.66(1H, dd, J=8.6, 7.6Hz), 6.90(1H, dd, J=10.1, 10.1Hz), 7.10(1H, m), 7.98(1H, m), 8.27(1H, m). |
| IIm | 3-ethylsulfonyl-2-pyridyl | Cl | F | O | mp 189~191 | 1.33(3H, t), 3.56(2H, q), 3.88(2H, br s), 6.72(1H, d) 7.10~7.27(2H, m), 8.31~8.39(2H, m). |
| IIn | 3-methyl-4-nitro-5-isothiazolyl | Cl | F | O | amorphous | 2.68(3H, s), 4.11(2H, br s), 6.79(1H, d, J=8.0 Hz), 7.15(1H, d, J=10.2Hz). |
| IIo | 2-pyridyl | Cl | F | O | mp 124–126 | 3.82(2H, br s), 6.62(1H, s), 6.98(2H, m), 7.10(1H, d, J=10.5Hz), 7.69(1H, m), 8.15(1H, m). |
| IIp | 2-pyrimidyl | Cl | F | O | yellow crystals | 4.75(2H, br s), 6.78(1H, d, J=8.4Hz), 7.09(1H, d, J=10.6Hz), 7.15(1H, t, J=4.8Hz), 8.56(2H, d, J=4.8Hz). |

TABLE 10-continued

Examples of Intermediate (II), (III), and (XX)

| Intermediate No. | Ar | Y | X | Z | Physical property | ¹H NMR (CDCl₃) |
|---|---|---|---|---|---|---|
| IIq | 4-chloro-2-pyrimidyl | Cl | F | O | amorphous | 5.61(2H, br s), 6.82(1H, d, J=5.7Hz), 6.84(1H, d, J=8.2Hz), 7.08(1H, d, J=10.5Hz), 8.42(1H, d, J=5.7Hz). |
| IIr | 4-6-dimethoxy-2-pyrimidyl | Cl | F | O | amorphous | 3.81(6H, s), 5.77(1H, s), 6.67(1H, d, J=8.4Hz), 7.06(1H, d, J=10.4Hz). |
| IIs | 4-chloro-2-pyrimidyl | Cl | Cl | O |  | 6.69(1H, s), 7.34(1H, s), 7.08(1H, t, J=4.8Hz), 8.56(1H, d, J=4.8Hz). |
| IIt | 2-nitrophenyl | Cl | F | O |  | 3.85(2H, br s), 6.55(1H, d, J=8.4Hz), 6.82(1H, dd, J=8.5, 1.0Hz), 7.12(1H, dd, J=10.4, 1.0Hz), 7.17(1H, ddd, J=8.2, 7.4, 1.2Hz), 7.48(1H, ddd, J=8.5, 7.4, 1.7Hz), 7.96(1H, dd, J=8.1, 1.7Hz). |
| IIIc | 2-pyrimidyl | Cl | F | O |  | 7.03(1H, d, J=7.2Hz), 7.10(1H, t, J=4.8Hz), 7.31(1H, d, J=8.9Hz), 8.57(1H, d, J=4.8Hz), |
| IIId | 3-trifluoromethyl-2-pyrimidyl | Cl | F | O |  | 7.02(1H, d, J=7.3Hz), 7.14(1H, dd, 6.9, 5.0Hz,), 7.31(1H, d, J=8.9Hz), 8.02(1H, d, J=6.9Hz), 8.25(1H, d, J=5.0Hz). |
| XX | 3-trifluoromethyl-2-pyridyl | Cl | F | O |  | 7.12(1H, d, J=6.9Hz), 7.16(1H, m), 7.31(1H, d, J=8.9Hz), 8.03(1H, m), 8.24(1H, m). |

TABLE 11

Examples of Intermediates (XXXV)

(XXXV)

| Intermediate No. | Ar | X | Y | Physical property | ¹H NMR (CDCl₃) |
|---|---|---|---|---|---|
| 11-1 | 3-nitro-2-pyridyl | F | Cl | mp 220–223 | 1.55(1H, br s), 6.24(1H, s), 7.23(2H, m), 7.43(1H, d, J = 7.9 Hz), 8.33(1H, m), 8.43(1H, m). |
| 11-2 | 5-bromo-2-pyridyl | F | Cl | amorphous | 3.30(1H, br), 6.21(1H, s), 6.92(1H, m), 7.20(1H, d, J = 6.7 Hz), 7.38(1H, d, J = 9.0 Hz), 7.81(1H, m), 8.13(1H, m). |
| 11-3 | 5-chloro-2-pyridyl | F | Cl | oil | 6.19(1H, s), 6.96(1H, d, J = 8.7 Hz), 7.20(1H, d J = 6.7 Hz), 7.37(1H, d, J = 8.9 Hz), 7.68(1H, dd, J = 8,7,2.6 Hz), 8.03(1H, d, J = 2.6 Hz). |
| 11-4 | 6-fluoro-2-pyridyl | F | Cl | amorphous | 6.22(1H, s), 6.64(1H, dd, J = 2.5, 8.0 Hz), 6.81(1H d, J = 8.0 Hz), 7.21(1H, d, J = 6.7 Hz), 7.38(1H, d, J = 9.0 Hz), 7.79(1H, d, J = 7.9, 15.8 Hz). |
| 11-5 | 6-chloro-2-pyridyl | F | Cl | amorphous | 6.17(1H, s), 6.80(1H, m), 7.04(1H, m), 7.20(1H, m), 7.35(1H, m), 7.63(1H, m). |
| 11-6 | 3,5,6-trifluoro-2-pyridyl | F | Cl | amorphous | 6.22(1H, s), 7.23(1H, d, J = 6.6 Hz), 7.40(1H, d, J = 8.9 Hz), 7.54(1H, m), 8.04(1H, br s). |
| 11-7 | 3-trifluoromethyl-2-pyridyl | F | Cl | amorphous | (acetone-d₆-CDCl₃) 6.22(1H, s), 7.20(1H, m), 7.36(1H, d, J = 6.7 Hz), 7.42(1H, d, J = 9.0 Hz), 8.06(1H, m), 8.24(1H, m). |
| 11-8 | 4-trifluoromethyl-2-pyridyl | F | Cl | amorphous | 6.22(1H, s), 7.23(3H, Hz), 7.40(1H, J = 9.0 Hz), 8.25(1H, d, J = 5.1 Hz). |
| 11-9 | 3-cyano-2-pyridyl | F | Cl | amorphous | 6.22(1H, s), 7.16(1H, dd, J = 5.0, 7.5 Hz), 7.27(1H, d, J = 6.6 Hz), 7.40(1H, d, J = 9.0 Hz), 8.05(1H, dd, J = 1.9, 7.5 Hz), 8.27(1H, dd, J = 1.9, 5.0 Hz). |
| 11-10 | 5-cyano-2-pyridyl | F | Cl | amorphous | 6.23(1H, s), 7.12(1H, d, J = 8.6 Hz), 7.21(1H, d, J = 6.6 Hz), 7.41(1H, d, J = 8.9 Hz), 7.97(1H, dd, J = 2.3, 8.6 Hz) 8.41(1H, d, J = 2.3 Hz). |
| 11-11 | 5-nitro-2-pyridyl | F | Cl | amorphous | (CDCl₃ + CD₃OD) 6.21(1H, s), 7.16(1H, d, J = 9.1 Hz), 7.27(1H, d, J = 6.6 Hz), 7.45(1H, d, J = 8.8 Hz), 8.55(1H, dd, J = 2.8, 9.0 Hz), 8.99(1H, d, J = 2.7 Hz). |

TABLE 11-continued

Examples of Intermediates (XXXV)

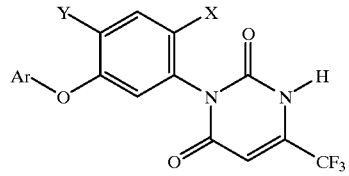

(XXXV)

| Intermediate No. | Ar | X | Y | Physical property | $^1$H NMR (CDCl$_3$) |
|---|---|---|---|---|---|
| 11-12 | 3-trifluoro-methyl-2-pyridyl | F | F | amorphous | 6.2(1H, s), 7.11(1H, m), 7.14(1H,m), 7.23(1H, m), 7.99(1H, d, J = 7.6 Hz), 8.23(1H, d, J = 5.0 Hz). |
| 11-13 | 3-ethyl-sulfonyl-2-pyridyl | F | Cl | amorphous | 1.32(3H, t), 3.57(2H, q), 6.24(1H, s), 7.26(2H, d), 7.42(1H,d), 8.30(1H, d), 8.37(1H, d), 10.20(1H, br s). |
| 11-14 | 3-methyl-4-nitro-5-isothiazolyl | F | Cl | amorphous | 2.70(3H, s), 6.27(1H, s), 7.39(1H, d, J = 6.4 Hz), 7.51(1H, d, J = 8.6 Hz). |
| 11-15 | 2-pyrimidyl | F | Cl | amorphous | 6.22(1H, s), 7.18(1H, t, J = 4.8 Hz), 7.37(1H, d, J = 6.8 Hz), 7.44(1H, d, J = 9.0 Hz), 8.58(2H, d,J = 4.8 Hz), 8.01(1H, br). |
| 11-16 | 4-chloro-2-pyrimidyl | F | Cl | amorphous | (acetone-d$_6$-CDCl$_3$) 4.73(1H, s), 6.22(1H, s), 6.95(1H, d, J = 5.6 Hz), 7.29(1H, d, J = 6.6 Hz), 7.43(1H, d, J = 8.9 Hz), 8.51(1H, d, J = 5.6 Hz). |
| 11-17 | 4,6-dime-thoxy-2-pyrimidyl | F | Cl | amorphous | (DMSO-d$_6$-CDCl$_3$), 3.81(6H, s), 5.85(1H, s), 6.20(1H, s), 7.45(1H, d, J = 6.8 Hz), 7.54(1H, d, J = 9.1 Hz). |
| 11-18 | 2-nitro-phenyl | F | Cl | mp 177–179 | 6.24(1H,s), 6.93(1H, d, J = 8.4 Hz), 7.06(1H, d, J = 6.4 Hz), 7.24(1H, t, J = 8.0 Hz), 7.44(1H, d, J = 8.9 Hz), 7.53(1H, ddd, J = 8.4, 8.0, 1.6 Hz), 7.99(1H, dd, J = 8.0, 1.6 Hz), 9.10(1H, br s). |
| 11-19 | 3-methyl-sulfonyl-2-pyridyl | F | Cl | mp 262–264 | 3.40(3H, s), 6.16(1H, s), 7.27~7.36(2H, m), 7.45(1H, d), 8.34~8.40(2H, m), 12.70(1H, br. s). |
| 11-20 | 3-i-propyl-sulfonyl-2-pyridyl | F | Cl | mp 275–277 | 1.36(6H, d), 3.95(1H, q), 6.16(1H, s), 7.27~7.35(3H, m) 7.45(1H, d), 8.35(1H, d), 12.7(1H, br.s). |
| 11-21 | 4-nitrophenyl | F | Cl | amorphous | 6.17(1H, s), 7.09(2H, d, J = 9.2 Hz), 7.24(1H, d, J = 6.5 Hz), 7.50(1H, d, J = 8.9 Hz), 8.23(2H, d, J = 9.2 Hz), 12.6(1H, br). |
| 11-22 | 4-nitro-2-trifluorome-thylphenyl | F | Cl | amorphous | 6.28(1H, s), 6.86(1H, d, J = 9.1 Hz), 7.21(1H, d,J = 6.5 Hz), 7.50(1H, d, J = 8.7 Hz), 8.34(1H, dd, J = 9.1, 2.7 Hz), 8 61(1H, d, J = 2.5 Hz). |
| 11-23 | 3-nitro-5-trifluorome-thylphenyl | F | Cl | amorphous | 6.28(1H, s), 7.16(1H, d, J = 6.4 Hz), 7.51(1H, d, J = 8.8 Hz), 7.54(1H, br s), 7.94(1H, t, J = 2.0 Hz), 8.23(1H, br s), 9.60(1H, br s). |
| 11-24 | 4-amino-2-trifluoromo-thylphenyl | F | Cl | amorphous | 6.21(1H, s), 6.75(3H, m), 6.97(1H, s), 7.40(1H, d, J = 9.0 Hz). |
| 11-25 | 4-amino-phenyl | F | Cl | amorphous | 5.95(2H, br), 6.14(1H, s), 6.60(2H, d, J = 8.6 Hz), 6.69(1H, d, J = 6.7 Hz), 6.71(2H, d, J = 8.6 Hz), 7.32(1H, d, J = 8.9 Hz). |
| 11-26 | 3-amino-5-trifluorome-thylphenyl | F | Cl | amorphous | 6.19(1H, s), 6.69(1H, br s), 6.81(1H, br s), 6.92(1H, br s) 6.97(1H, d, J = 6.4 Hz), 7.30(1H, br s), 7.38(1H, d, J = 9.0 Hz). |
| 11-27 | 2-amino phenyl | F | Cl | amorphous | 6.19(1H, s), 6.69(1H, ddd, J = 9.4, 8.7, 1.2 Hz), 6.80(3H, m), 6.98(1H, ddd, J = 9.4, 8.5, 1.4 Hz), 7.38(1H, d, J = 8.9 Hz). |
| 11-28 | 2-trifluoro-methyl-phenyl | F | Cl | amorphous | 6.24(1H, s), 6.83(1H, d, J = 8.2 Hz), 7.01(1H, d, J = 6.5 Hz), 7.20(1H, t, J = 7.6 Hz), 7.43(1H, d, J = 8.9 Hz), 7.47(1H, m), 7.70(1H, d, J = 7.6 Hz), 9.10(1H, br s). |
| 11-29 | 3-trifluoro methyl-phenyl | F | Cl | amorphous | 6.25(1H, s), 6.98(1H, d, J = 6.6 Hz), 7.11(1H, d, m), 7.27(1H, br s), 7.44(1H, d, J = 8.8 Hz), 7.38–7.48(2H, m), 10.2(1H, br s). |
| 11-31 | 4-hydroxy-phenyl | F | Cl | amorpbous | |
| 11-32 | 1,4-(1-ethoxy-1-carbonyl-1-ethoxy)-phenyl | F | Cl | amorphous | 1.25(3H, dd, J = 1.5, 7.1 Hz), 1.60(3H, d, J = 6.8 Hz), 4.12(2H, dq, J = 1.5, 7.1 Hz), 4.68(1H, q, J = 6.8 Hz), 6.20(1H, s), 6.73(1H, d, J = 6.6 Hz), 6.84(2H, d, J = 9.1 Hz), 6.95(2H, d, J = 9.1 Hz), 7.37(1H, d, J = 8.9 Hz). |

TABLE 11-continued

Examples of Intermediates (XXXV)

(XXXV)

| Intermediate No. | Ar | X | Y | Physical property | ¹H NMR (CDCl₃) |
|---|---|---|---|---|---|
| 11-33 | 1,2-cyano-phenyl | F | Cl | mp 240–246 | 6.26(1H, s), 6.75(1H, d, J = 8.4 Hz), 7.14(1H, d, J = 6.5 Hz), 7.20(1H, t, J = 7.4 Hz), 7.45(1H, d, J = 8.8 Hz), 7.45(1H, ddd, J = 8.4, 7.4, 1.7 Hz), 7.68(1H, dd, J = 7.4, 1.7 Hz), 9.98(1H, br s). |
| 11-34 | 2-cyano-3-fluorophenyl | F | Cl | mp 215–218 | 6.26(1H, s), 6.52(1H, d, J = 8.8 Hz), 6.94(1H, t, J = 8.4 Hz), 7.20(1H, d, J = 6.6 Hz), 7.41–7.49(2H, m). |

TABLE 12

¹H NMR data

| Compd No. | ¹H NMR (CDCl₃, TMS) |
|---|---|
| 1-1 | 4.06(3H, brs), 7.22(1H, dd, J=4.9, 8.0 Hz), 7.37(1H, d, J=9.1 Hz), 7.48(1H, d, J=6.4 Hz), 8.32(1H, dd, J=1.7, 4.8 Hz), 8.42(1H, dd, J=1.7, 7.9 Hz). |
| 1-2 | 4.05(3H, m), 7.13(1H, m), 7.36(1H, d, J=9.1 Hz), 7.45(1H, d, J=6.6 Hz), 8.02(1H, m), 8.26(1H, m). |
| 1-3 | 4.06(3H, s), 7.16(1H, dd, J=5.0, 7.5 Hz), 7.36(1H, d, J=9.1 Hz), 7.48(1H, d, J=6.5 Hz), 8.06(1H, br dd, J=1.7, 7.5 Hz), 8.3(1H, br dd, J=1.7, 5.0 Hz). |
| 1-4 | 4.06(3H, s), 7.14(1H, d, J=8.6 Hz), 7.37(1H, d, J=9.1 Hz), 7.42(1H, d, J=6.5 Hz), 7.98 (1H, dd, J=2.3, 8.6 Hz), 8.43(1H, br d, J=2.1 Hz). |
| 1-5 | 4.05(3H, s), 6.63(1H, dd, J=2.6, 8.0 Hz), 6.84(1H, br d, J=7.8 Hz), 7.34(1H, d, J=9.2 Hz), 7.42(1H, d, J=6.6 Hz), 7.80(1H, dd, J=8.0, 16.0 Hz). |
| 1-6 | 4.05(3H, s), 7.33(1H, d, J=9.1 Hz), 7.44(1H, d, J=6.4 Hz), 7.52(1H, br dd, J=7.7, 14.8 Hz). |
| 1-7 | 4.06(3H, s), 7.08(1H, dd, J=4.8 Hz), 7.36(1H, d, J=9.1 Hz), 7.47(1H, d, J=6.6 Hz), 8.58(2H, d, J=4.8 Hz). |
| 1-8 | 4.01(6H, s), 4.07(3H, m), 7.35(1H, d, J=9.1 Hz), 7.45(1H, d, J=6.6 Hz). |
| 2-1 | 2.60(3H, br s), 7.18(1H, t, J=58.1 Hz), 7.20(1H, dd, J=4.8, 7.9 Hz), 7.32(1H, d, J=9.3 Hz), 7.57(1H, d, J=6.6 Hz), 8.30(1H, dd, J=1.8, 4.8 Hz), 8.41(1H, dd, J=1.8, 7.9 Hz). |
| 2-2 | 2.60(3H, br s), 7.11(1H, m), 7.15(1H, t, J=58.1 Hz), 7.31(1H, d, J=9.5 Hz), 7.54(1H, d, J=6.7 Hz), 8.01(1H, m), 8.24(1H, m). |
| 2-3 | 2.61(3H, br s), 7.07(1H, t, J=4.8 Hz), 7.17(1H, t, J=58.1 Hz), 7.32(1H, d, J=9.5 Hz), 7.56(1H, d, J=6.7 Hz), 8.56(2H, d, J=4.8 Hz). |
| 2-4 | 2.61(3H, br s), 4.00(6H, s), 7.17(1H, t, J=58.1 Hz), 7.29(1H, d, J=9.3 Hz), 7.53(1H, d, J=6.6 Hz). |
| 3-1 | 2.48(3H, br s), 7.05(1H, t, J=58.0 Hz), 7.09(1H, t, J=4.8 Hz), 7.37(1H, d, J=9.5 Hz), 7.48(1H, d, J=6.8 Hz), 8.57(2H, d, J=4.8 Hz). |
| 4-1 | 1.90(3H, s), 2.30(3H, s), 7.12(1H, dd, J=5.7 Hz), 7.30(1H, d, J=7 Hz), 7.40(1H, d, J=9 Hz), 8.00(1H, d, J=7 Hz), 8.25(1H, m), 8.62(1H, s). |
| 4-2 | 1.98(2H, m), 2.41(2H, m), 3.75(2H, m), 6.24(1H, t, J=4.5 Hz), 7.14(1H, m), 7.31(1H, d, J=6.7 Hz), 7.41(1H, d, J=9.1 Hz), 8.01(1H, m), 8.25(1H, m). |
| 5-1 | 2.20(2H, m), 3.00(2H, m), 3.99(2H, m), 5.71(1H, s), 6.92(1H, m), 7.08(1H, d, J=6.6 Hz), 7.20(1H, m), 7.39(1H, d, J=8.8 Hz), 7.50(1H, m), 7.94(1H, m). |
| 5-2 | 2.21(2H, m), 3.01(2H, t, J=8.1 Hz), 3.99(2H, m), 5.73(1H, s), 7.02(2H, d, J=9.3 Hz), 7.11(1H, d, J=6.6 Hz), 7.41(1H, d, J=8.9 Hz), 8.20(2H, d, J=9.3 Hz). |
| 5-3 | 2.18(2H, m), 2.95(2H, t, J=7.7 Hz), 3.6(2H, br), 3.95(2H, m), 5.67(1H, s), 6.62(2H, d, J=8.9 Hz), 6.70(1H, d, J=6.7 Hz), 6.85(2H, d, J=8.9 Hz), 7.31(1H, d, J=8.9 Hz). |
| 5-5 | 2.22(2H, m), 3.10(2H, m), 3.52(3H, s), 3.99(2H, m), 5.69(1H, s), 7.08(2H, d, J=9.1 Hz), 7.37(1H, d, J=6.8 Hz), 7.56(2H, d, J=9.1 Hz), 7.67(1H, d, J=9.3 Hz). |
| 5-6 | 2.17(2H, m), 2.97(2H, m), 3.96(2H, m), 6.65(2H, d, J=8.9 Hz), 6.72(1H, d, J=6.7 Hz), 6.84(2H, d, J=9.0 Hz), 7.02(1H, s), 7.32(1H, d, J=8.9 Hz). |
| 5-7 | 2.21(2H, m), 3.01(2H, t, J=7.8 Hz), 4.01(2H, m), 5.74(1H, s), 6.97(1H, m), 7.21(1H, d, J=6.7 Hz), 7.37(1H, d, J=9.0 Hz), 7.75(1H, m), 7.98(1H, m). |
| 5-8 | 2.21(2H, m), 3.01(2H, t, J=7.8 Hz), 4.02(2H, m), 5.73(1H, s), 7.18(1H, m), 7.22(1H, d, J=6.8 Hz), 7.37(1H, d, J=8.9 Hz), 8.30(1H, m), 8.39(1H, m). |
| 5-9 | 2.19(2H, m), 3.00(2H, m), 3.99(2H, m), 5.73(1H, s), 7.12(1H, m), 7.23(1H, d, J=6.6 Hz), 7.35(1H, d, J=8.9 Hz), 8.00(1H, m), 8.26(1H, m). |
| 5-10 | 2.20(2H, m), 3.00(2H, t, J=8.0 Hz), 3.99(2H, m), 5.74(1H, s), 7.10(1H, m), 7.24(1H, m), 7.36(1H, d, J=8.9 Hz), 7.99(1H, d, J=6.6 Hz), 8.25(1H, m). |
| 5-11 | 2.20(2H, m), 3.00(2H, t, J=7.9 Hz), 4.00(2H, m), 5.74(1H, s), 7.09(1H, d, J=8.6 Hz), 7.18(1H, d, J=6.7 Hz), 7.37(1H, d, J=8.9 Hz), 7.94(1H, m), 8.41(1H, d, J=2.3 Hz). |

TABLE 12-continued

¹H NMR data

| Compd No. | ¹H NMR (CDCl₃, TMS) |
|---|---|
| 5-12 | 2.20(2H, m), 3.00(2H, t, J=7.8 Hz), 4.00(2H, m), 5.73(1H, s), 7.05(1H, t, J=4.8 Hz), 7.22(1H, d, J=6.8 Hz), 7.36(1H, d, J=9.0 Hz), 8.54(2H, d, J=4.7 Hz). |
| 6-1 | 2.29(2H, dtt, J=26.4, 6.9, 5.6 Hz), 4.20(2H, t, J=6.9 Hz), 4.60(2H, dt, J=46.9, 5.6 Hz), 6.65(1H, d, J=8.3 Hz), 6.90–7.15(3H, m), 7.72(1H, m), 8.18(1H, m). |
| 6-2 | 2.29(2H, dtt, J=26.4, 6.9, 5.6 Hz), 4.20(2H, t, J=6.9 Hz), 4.58(2H, dt, J=47.0, 5.6 Hz), 7.27(1H, dd, J=8.0, 4.8 Hz), 7.49(1H, d, J=9.3 Hz), 7.61(1H, d, J=6.7 Hz), 8.31(1H, dd, J=4.8, 1.7 Hz), 8.45(1H, dd, J=8.0, 1.7 Hz). |
| 6-6 | 2.28(2H, dtt, J=26.4, 7.0, 5.8 Hz), 4.19(2H, t, J=7.0 Hz), 4.58(2H, dt, J=46.7, 5.8 Hz), 7.16(1H, dd, J=7.5, 5.0 Hz), 7.47(1H, d, J=9.4 Hz), 7.58(1H, d, J=6.7 Hz), 8.03(1H, d, J=7.5 Hz), 8.24(1H, d, J=5.0 Hz). |
| 6-7 | 2.29(2H, dtt, J=26.4, 5.9, 5.6 Hz), 4.20(2H, t, J=5.9 Hz), 4.58(2H, dt, J=47.0, 5.6 Hz), 7.15(1H, m), 7.47(1H, s), 7.58(1H, s), 8.03(1H, m), 8.24(1H, m). |
| 6-8 | 2.29(2H, dtt, J=26.4, 6.9, 5.6 Hz), 4.20(2H, t, J=6.9 Hz), 4.58(2H, dt, J=47.0, 5.6 Hz), 7.16(1H, d, J=8.6 Hz), 7.47(1H, d, J=9.3 Hz), 7.54(1H, d, J=6.7 Hz), 7.97(1H, dd, J=8.6, 2.5 Hz), 8.38(1H, d, J=2.5 Hz). |
| 6-9 | 2.30(2H, dtt, J=26.4, 6.9, 5.6 Hz), 4.20(2H, t, J=6.9 Hz), 4.58(2H, dt, J=47.0, 5.6 Hz), 7.16(1H, dd, J=8.7, 0.7 Hz), 7.44(1H, s), 7.73(1H, s), 7.97(1H, dd, J=8.7, 2.5 Hz), 8.38(1H, dd, J=2.5, 0.7 Hz). |
| 6-10 | 2.30(2H, m), 4.20(2H, t, J=6.9 Hz), 4.59(2H, dt, J=46.9, 6.6 Hz), 7.13(1H, dd, J=4.8 Hz), 7.48(1H, d, J=9.3 Hz), 7.58(1H, d, J=6.8 Hz), 8.58(2H, d, J=4.8 Hz). |
| 6-11 | 1.51(3H, t, J=7.3 Hz), 4.08(2H, q, J=7.3 Hz), 7.12(1H, dd, J=4.8 Hz), 7.47(1H, d, J=9.3 Hz), 7.58(1H, d, J=6.7 Hz), 8.58(2H, d, J=4.8 Hz). |
| 6-12 | 3.79(2H, t, J=5.4 Hz), 4.20(2H, t, J=5.4 Hz), 7.10(1H, dd, J=5.8 Hz), 7.45(1H, d, J=9.3 Hz), 7.58(1H, d, J=6.8 Hz), 8.56(2H, d, J=5.8 Hz). |
| 6-13 | 3.07(2H, t, J=6.7 Hz), 4.38(2H, t, J=6.7 Hz), 7.20(2H, m), 7.55(1H, d, J=9.3 Hz), 8.58(2H, d, J=5.8 Hz). |
| 6-14 | 2.29(2H, dtt, J=26.5, 5.9, 5.6 Hz), 4.20(2H, t, J=5.9 Hz), 4.58(2H, dt, J=47.0, 5.6 Hz), 7.14(1H, dd, J=4.8 Hz), 7.52(1H, s), 7.74(1H, s), 8.57(2H, d, J=4.8 Hz). |
| 6-15 | 2.30(2H, dtt, J=26.4, 6.9, 5.5 Hz), 3.84(6H, s), 4.20(2H, t, J=6.9 Hz), 4.59(2H, dt, J=47.0, 5.5 Hz), 5.82(1H, s), 7.46(1H, d, J=9.3 Hz), 7.57(1H, d, J=6.8 Hz). |
| 6-16 | 2.30(2H, dtt, J=26.3, 7.1, 5.5 Hz), 4.19(2H, t, J=7.1 Hz), 4.58(2H, dt, J=46.9, 5.5 Hz), 7.49(1H, d, J=9.3 Hz), 7.59(1H, d, J=6.6 Hz), 8.58(2H, s). |
| 6-17 | 2.30(2H, dtt, J=26.4, 6.9, 5.6 Hz), 2.69(3H, s), 4.20(2H, t, J=6.9 Hz), 4.58(2H, dt, J=47.0, 5.6 Hz), 7.61(1H, s), 7.84(1H, s). |
| 7-1 | 1.86(4H, m), 3.76(4H, m), 6.90(1H, d, J=7.6 Hz), 7.13(1H, m), 7.25(1H, d, J=9.7 Hz), 8.02(1H, m), 8.27(1H, m). |
| 7-2 | 1.85(4H, m), 3.74(4H, m), 6.89(1H, d), 7.04(1H, t), 7.25(1H, d), 8.56(2H, d). |
| 8-1 | 1.24(3H, t, J=7 Hz), 3.53(2H, q, J=7 Hz), 4.05(2H, s), 7.13(1H, m), 7.30(1H, d, J=7 Hz), 7.38(1H, d, J=9 Hz), 8.01(1H, m), 8.24(1H, m). |
| 8-2 | 1.25(3H, t, J=7.3 Hz), 3.54(2H, q, J=7.3 Hz), 4.08(2H, s), 7.09(1H, t, J=4.8 Hz), 7.31(1H, d, J=6.7 Hz), 7.40(1H, d, J=9.2 Hz), 8.56(2H, d, J=4.8 Hz). |
| 8-3 | 3.05(3H, s), 4.09(2H, s), 7.09(1H, t, J=4.8 Hz), 7.30(1H, d, J=6.7 Hz), 7.39(1H, d, J=9.2 Hz), 8.54(2H, d, J=4.8 Hz). |
| 8-4 | 1.47(3H, m), 1.78(1H, m), 2.03(1H, m), 2.27(1H, m), 2.91(1H, m), 3.96(1H, m), 4.22(1H, m), 7.11(1H, m), 7.28(1H, d, J=6.7 Hz), 7.37(1H, d, J=9.1 Hz), 8.00(1H, m), 8.22(1H, m). |
| 8-5 | 1.94(4H, m), 3.68(2H, m), 3.98(2H, m), 7.05(3H, m), 7.12(1H, m), 7.35(2H, m), 7.41(1H, m). |
| 8-6 | 1.93(4H, m), 3.69(2H, m), 3.96(2H, m), 6.98(1H, d, J=8.3 Hz), 7.21(2H, m), 7.43(1H, d, J=8.9 Hz), 7.50(1H, m), 7.95(1H, d, J=8.0 Hz). |
| 8-7 | 1.96(4H, m), 3.70(2H, m), 4.00(2H, m), 6.83(1H, d, J=8.6 Hz), 7.16(1H, m), 7.29(1H, m), 7.48(2H, m), 7.67(1H, m). |
| 8-8 | 1.97(4H, m), 3.68(2H, m), 3.98(2H, m), 7.07(2H, d, J=9.1 Hz), 7.30(1H, d, J=6.6 Hz), 7.47(1H, d, J=8.8 Hz), 8.24(2H, d, J=9.1 Hz). |
| 8-9 | 1.94(4H, m), 3.66(2H, m), 3.68(2H, m), 3.98(2H, m), 6.66(2H, d, J=8.9 Hz), 6.86(1H, d, J=6.6 Hz), 6.90(2H, d, J=8.9 Hz), 7.38(1H, d, J=8.9 Hz). |
| 8-11 | 1.26(3H, t, J=7.1 Hz), 1.60(3H, d, J=6.8 Hz), 1.94(4H, m), 3.68(2H, m), 3.98(2H, m), 4.22(2H, q, J=7.1 Hz), 4.68(1H, q, J=6.8 Hz), 6.85(2H, d, J=8.8 Hz), 6.89(1H, d, J=6.5 Hz), 6.98(2H, d, J=8.9 Hz), 7.37(1H, d, J=8.9 Hz). |
| 8-12 | 1.99(4H, m), 3.71(2H, m), 4.02(2H, m), 6.95(1H, d, J=9.3 Hz), 7.42(1H, d, J=6.4 Hz), 7.51(1H, d, J=8.7 Hz), 8.37(1H, m), 8.59(1H, d, J=2.7 Hz). |
| 8-14 | 1.98(4H, m), 3.70(2H, m), 4.02(2H, m), 6.95(1H, d, J=9.1 Hz), 7.36(1H, d, J=6.4 Hz), 7.50(1H, d, J=8.8 Hz), 8.35(1H, m), 8.60(1H, d, J=2.5 Hz). |
| 8-15 | 1.97(4H, m), 3.74(2H, m), 3.79(2H, br), 4.02(2H, m), 6.46(1H, d), 6.72(1H, d), 7.13(1H, d), 7.64(1H, m), 7.73(1H, m). |
| 8-16 | 1.92(4H, m), 2.10(3H, s), 3.67(2H, m), 3.96(2H, m), 6.85(1H, d, J=9.1 Hz), 7.05(1H, d, J=6.3 Hz), 7.38(1H, d, J=8.9 Hz), 7.62(1H, m), 7.82(1H, s), 8.26(1H, s). |
| 8-17 | 1.90(4H, m), 3.66(2H, m), 3.97(2H, m), 6.97(2H, m), 7.33(1H, d, J=6.7 Hz), 7.39(1H, d, J=9.0 Hz), 7.68(1H, m), 8.10(1H, m). |
| 8-18 | 1.95(4H, m), 3.71(2H, m), 4.01(2H, m), 7.13(1H, m), 7.38(1H, d, J=6.7 Hz), 7.42(1H, d, J=9.0 Hz), 8.00(1H, m), 8.24(1H, m). |
| 8-19 | 1.97(4H, m), 3.71(2H, m), 4.01(2H, m), 7.21(1H, m), 7.40(1H, d, J=6.6 Hz), 7.42(1H, d, J=8.8 Hz), 8.30(1H, m), 8.39(1H, m). |
| 8-20 | 1.97(4H, m), 3.71(2H, m), 4.02(2H, m), 7.14(1H, m), 7.41(1H, d, J=6.6 Hz), 7.43(1H, d, J=8.9 Hz), 8.04(1H, m), 8.28(1H, m). |
| 8-21 | 1.96(4H, m), 3.38(3H, s), 3.69(2H, m), 4.00(2H, m), 7.24(1H, m), 7.44(2H, m), 8.32(1H, m), 8.38(1H, m). |
| 8-22 | 1.95(4H, m), 3.71(2H, m), 4.02(2H, m), 7.12(1H, d, J=8.6 Hz), 7.35(1H, d, J=6.6 Hz), 7.43(1H, d, J=8.9 Hz), 7.96(1H, m), 8.42(1H, d, J=2.4 Hz). |
| 8-23 | 1.97(4H, m), 3.71(2H, m), 4.02(2H, m), 7.12(1H, d, J=9.0 Hz), 7.38(1H, d; J=6.7 Hz), 7.43(1H, d, J=9.0 Hz), 8.53(1H, m), 8.99(1H, m). |
| 8-24 | 1.93(4H, m), 3.68(2H, m), 3.98(2H, m), 6.79(1H, d, J=8.7 Hz), 7.04(1H, m), 7.20(1H d, J=6.6 Hz), 7.34(1H, d, J=9.0 Hz), 7.59(1H, d, J=2.9 Hz). |
| 8-25 | 1.92(4H, m), 3.67(2H, m), 3.98(2H, m), 6.61(1H, d), 6.80(1H, m), 7.35(1H, d, J=6.7 Hz), 7.39(1H, d, J=9.0 Hz), 7.78(1H, m). |

TABLE 12-continued

$^1$H NMR data

| Compd No. | $^1$H NMR (CDCl$_3$, TMS) |
|---|---|
| 8-26 | 1.97(4H, m), 3.72(2H, m), 4.02(2H, m), 6.85(1H, m), 7.07(1H, m), 7.37(1H, d, J=6.6 Hz), 7.41(1H, d, J=8.9 Hz), 7.66(1H, m). |
| 8-27 | 1.95(4H, m), 3.68(2H, m), 4.00(2H, m), 6.98(1H, d, J=8.5 Hz), 7.38(1H, d, J=6.6 Hz), 7.43(1H, d, J=8.9 Hz), 8.01(1H, d, J=8.5 Hz). |
| 8-28 | 1.96(4H, m), 3.71(2H, m), 4.00(2H, m), 7.38(1H, d, J=6.9 Hz), 7.42(1H, d, J=8.8 Hz), 7.54(1H, m). |
| 8-29 | 1.92(4H, m), 3.69(2H, m), 3.99(2H, m), 7.05(1H, m), 7.37(1H, d, J=6.5 Hz), 7.39(1H d, J=9.0 Hz), 8.53(2H, d, J=4.8 Hz). |
| 8-30 | 1.96(4H, m), 3.71(2H, m), 4.00(2H, m), 7.41(1H, d, J=4.9 Hz), 8.77(1H, s). |
| 8-31 | 1.94(4H, m), 3.68(2H, m), 3.98(2H, m), 6.90(1H, d, J=5.7 Hz), 7.37(1H, d, J=6.5 Hz) 7.42(1H, d, J=8.9 Hz), 8.46(1H, d, J=5.7 Hz). |
| 8-32 | 1.94(4H, m), 3.69(2H, m), 3.80(3H, s), 3.93(3H, s), 3.97(2H, m), 5.88(1H, s), 7.31(1H, d, J=6.6 Hz), 7.38(1H, d, J=8.9 Hz). |
| 8-33 | 1.95(4H, m), 3.69(2H, m), 3.81(6H, s), 4.00(2H, m), 5.77(1H, s), 7.32(1H, d, J=6.7 Hz), 7.39(1H, d, J=8.9 Hz). |
| 8-34 | 1.94(4H, m), 3.67(2H, m), 3.93(2H, m), 3.95(6H, s), 7.33(1H, d, 6.6 Hz), 7.39(1H, d, 8.9 Hz). |
| 8-35 | 1.97(4H, m), 2.68(3H, s), 3.69(2H, m), 4.01(2H, m), 7.49(1H, d, J=8.7 Hz), 7.56(1H, d, J=6.3 Hz). |
| 8-36 | 1.98(4H, m), 3.71(2H, m), 4.02(2H, m), 7.47(1H, d, J=8.7 Hz), 7.57(1H, d, J=6.4 Hz), 8.06(1H, s). |
| 8-37 | 1.34(6H, 2d, J=5.8, 5.2 Hz), 1.94(4H, m), 3.67(2H, m), 3.97(1H, m), 3.99(2H, m), 7.21(1H, m), 7.39(1H, m), 7.41(1H, 2d, J=1.1, 4.3Hz), 8.27(1H, m), 8.33(1H, m). |
| 8-38 | 1.30(3H, t, J=7.1 Hz), 1.70(3H, d, J=6.7 Hz), 1.96(4H, m), 3.70(2H, m), 4.00(2H, m), 4.26(2H, q, J=7.2 Hz), 4.79(1H, q, J=6.9 Hz), 7.13(1H, d, J=10.4 Hz), 7.14(1H, m), 7.43(1H, d, J=8.8 Hz), 7.53(1H, s). |
| 8-39 | 1.27(3H, t, J=7.1 Hz), 1.63(3H, d, J=6.8 Hz), 1.94(4H, m), 3.67(2H, m), 3.97(2H, m), 4.22(2H q, J=7.1 Hz), 4.74(1H, q, J=6.7 Hz), 7.00(1H, d, J=9.0 Hz), 7.02(1H, d, J=6.4 Hz), 7.10(1H, dd, J=3.0, 9.2 Hz), 7.41(1H, d, J=8.8 Hz), 7.46(1H, d, J=3.0 Hz). |
| 8-40 | 1.27(3H t, J=7.1 Hz), 1.62(3H, d, J=6.8 Hz), 1.95(4H, m), 3.68(2H, m), 3.99(2H, m), 4.23(2H, q, J=7.2 Hz), 4.46(1H, q, J=6.8 Hz), 6.19(1H, dd, J=2.9, 8.8 Hz), 6.36(1H, d, J=2.9 Hz), 6.83(1H, d, J=8.6 Hz), 6.85(1H, d, J=5.9 Hz), 7.38(1H, d, J=8.8 Hz). |
| 8-41 | 1.29(3H, t, J=7.1 Hz), 1.65(3H, d, J=6.8 Hz), 1.85(4H, m), 3.61(4H, m), 4.24(2H, q, J=7.1 Hz), 4.76(1H, q, J=6.7 Hz), 6.98(1H, d, J=6.6 Hz), 6.99(1H, d, J=2.4 Hz), 7.12(1H, 2d, J=3.1, 9.1 Hz), 7.43(1H, d, J=8.9 Hz), 7.48(1H, d, J=3.1 Hz). |
| 8-42 | 1.94(4H, m), 3.69(2H, m), 4.01(2H, m), 5.52(2H, br), 6.85(1H, dd, J=4.9, 7.7 Hz), 7.03(1H, dd, J=1.6, 7.6 Hz), 7.39(1H, d, J=9.0 Hz), 7.43(1H, d, J=6.7 Hz), 7.48(1H, dd, J=1.6, 4.8 Hz). |
| 8-43 | 1.95(4H, m), 2.50(3H, s), 3.69(2H, m), 3.98(2H, m), 7.02(1H, dd, J=6.9, 7.5 Hz), 7.38(1H, d, J=6.9 Hz), 7.41(1H, d, J=9.2 Hz), 7.53(1H, dd, J=1.5, 7.6 Hz), 7.84(1H, dd, J=1.6, 4.9 Hz). |
| 8-47 | 1.63(3H, m), 1.89(1H, m, 2.10(1H, m), 2.37(1H, m), 2.12(1H, m), 4.11(1H, m), 4.89 (1H, d, J=13.5 Hz), 7.1(1H, t, J=4.8 Hz), 7.28–7.33(1H, 2xd) J=8.5, 7.0 Hz), 7.40(1H, d, J=8.9 Hz), 8.57(2H, d, J=4.9 Hz). |
| 8-48 | 1.50(3H, m), 1.70(1H, m), 1.89(1H, m), 2.06(1H, m), 3.98(1H, m), 4.22(1H, m), 7.35 (1H, t, J=4.8 Hz), 7.64(1H, d, J=6.9 Hz), 7.90(1H, d, J=9.47 Hz), 8.70(2H, d, J=4.8 Hz). |
| 8-49 | 1.63(3H, m), 1.89(1H, m), 2.10(1H, m), 2.37(1H, m), 2.12(1H, m), 4.11(1H, m), 4.89 (1H, d, J=13.5 Hz), 7.09(1H, t, J=4.8 Hz), 7.28–7.33(1H, 2xd, J=8.5, 7.0 Hz), 7.40(1H, d, J=8.9 Hz), 8.57(2H, d, J=4.9 Hz). |
| 8-50 | 1.88(1H, m), 2.35(3H, m), 3.66(1H, m), 4.08(1H, m), 4.42(1H, m), 7.09(1H, t, J=4.8 Hz), 7.28–7.32(1H, 2xd, J=6.1, 6.7 Hz), 8.57(2H, d, J=4.8 Hz). |
| 8-51 | 1.57(3H, m), 1.87(1H, m), 2.07(1H, m), 2.32(1H, m), 3.06(1H, m), 4.06(1H, m), 4.84 (1H, d, J=13.34 Hz), 7.18(7H, m). |
| 8-52 | 1.61(3H, m), 1.90(1H, m), 2.06(1H, m), 2.33(1H, m), 3.08(1H, m), 4.08(1H, m), 4.85 (1H, d, J=13.5 Hz), 6.98(1H, m), 7.20(2H, m), 7.42(1H, d, J=8.8 Hz), 7.54(1H, m), 7.98(1H, dd, J=1.6, 8.1 Hz). |
| 8-53 | 1.61(3H, m), 1.91(1H, m), 2.10(1H, m), 2.37(1H, m), 3.12(1H, m), 4.10(1H, m), 4.86 (1H, d, J=13.6 Hz), 6.82(1H, d, J=8.5 Hz), 7.21(2H, m), 7.48(2H, m), 7.68(1H, dd, J=1.6, 7.7 Hz). |
| 8-54 | 1.63(3H, m), 1.90(1H, m), 2.07(1H, m), 2.34(1H, m), 3.09(1H, m), 4.07(1H, m), 4.88 (1H, d, J=13.5 Hz), 7.29(1H, m), 7.41(1H, d, J=4.8 Hz), 8.09(1H, dd, J=2.5, 3.9 Hz), 8.30(1H, d, J=2.7 Hz), 8.51(1H, d, J=1.1 Hz). |
| 8-55 | 1.60(3H, m), 1.89(1H, m), 2.09(1H, m), 2.36(1H, m), 3.10(1H, m), 4.10(1H, m), 4.87 (1H, d, J=13.5 Hz), 7.01(2H, m), 7.26(1H, m), 7.38(1H, d, J=9.0 Hz), 7.71(1H, m), 8.15(1H, d, J=2.3 Hz). |
| 8-56 | 1.59(3H, m), 1.9(1H, m), 2.08(1H, m), 2.35(1H, m), 3.10(1H, m), 4.08(1H, m), 5.90 (1H, d, J=14.0 Hz), 6.99(1H, m), 7.32(2H, m), 7.76(1H, dd, J=1.68, 7.7 Hz), 8.00(1H, d, J=2.9 Hz). |
| 8-57 | 1.57(3H, m), 1.86(1H, m), 2.06(1H, m), 2.30(1H, m), 3.08(1H, m), 4.09(1H, m), 4.85 (1H, d, J=13.5 Hz), 7.32(2H, m), 7.99(1H, d, J=2.1 Hz), 8.25(1H, s). |
| 8-58 | 1.61(3H, m), 1.87(1H, m), 2.09(1H, m), 2.34(1H, m), 3.12(1H, m), 4.10(1H, m), 4.88 (1H, d, J=13.5 Hz), 7.12(1H, m), 7.26(1H, m), 7.38(1H, d, J=8.9 Hz), 8.00(1H, dd, J=1.1, 6.4 Hz), 8.26(1H, d, J=2.4 Hz). |
| 8-59 | 1.61(3H, m), 1.90(1H, m), 2.07(1H, m), 2.37(1H, m), 3.10(1H, m), 4.10(1H, m), 4.89(1H, d, J=13.5 Hz), 7.33(3H, m), 8.40(1H, d, J=1.4 Hz), 8.42(1H, d, J=1.30 Hz). |
| 8-60 | 1.61(3H, m), 1.89(1H, m), 2.06(1H, m), 2.37(1H, m), 3.10(1H, m), 4.11(1H, m). 4.90 (1H, d, J=15.4 Hz), 7.16(1H, m), 7.36(2H, m), 8.03(1H, dd, J=2.0, 7.3 Hz), 8.31(1H, m). |
| 8-61 | 1.60(3H, m), 1.87(1H, m), 2.07(1H, m), 2.35(1H, m), 3.10(1H, m), 4.00(2H, s), 4.11(1H, m), 4.87(1H, d, J=12.1 H), 6.85(1H, m), 7.02(1H, m), 7.49(3H, m). |
| 8-62 | 1.56(3H, m), 1.87(1H, m), 2.05(1H, m), 2.30(1H, m), 3.05(1H, m), 3, 86(2H, d, J=4.51 Hz), 4.09(1H, m), 4.83(1H, d, J=13.2 Hz), 6.87(5H, m), 7.37(1H, d, J=8.8 Hz). |
| 8-63 | 1.60(3H, m), 1.90(1H, m), 2.10(1H, m), 2.28(3H, s), 2.32(1H, m), 3.10(1H, m), 4.10(1H, m), 8.70(1H, d, J=14.0 Hz), 7.07(1H, m), 7.40(1H, m), 7.77(1H, m), 7.85(1H, s), 8.73(1H, dd, J=1.2, 7.9 Hz). |

TABLE 12-continued

¹H NMR data

| Compd No. | ¹H NMR (CDCl₃, TMS) |
|---|---|
| 8-64 | 1.56(3H, m), 1.88(1H, m), 2.07(1H, m), 2.33(1H, m), 3.06(1H, m), 4.09(1H, m), 4.84 (1H, d, J=13.0 Hz), 6.90(1H, d, J=8.2 Hz), 7.26(9H, m), 7.89(2H, d, J=7.0 Hz), 8.10(2H, m), 8.60(2H, m). |
| 9-1 | 4.62(2H, s), 6.27(1H, s), 7.21(1H, m), 7.25(1H, d, J=7.5 Hz), 7.42(1H, d, J=9.0 Hz), 8.32(1H, dd, J=4.8, 1.8 Hz), 8.41(1H, dd, J=7.9, 1.8 Hz). |
| 9-2 | 4.63(2H, s), 6.26(1H, s), 6, 93(1H, d, J=8.7 Hz), 7.17(1H, d, J=6.7 Hz), 7.39(1H, d, J=9.0 Hz), 7.80(1H, dd, J=8.7, 1.7 Hz), 8.14(1H, d, J=1.7 Hz). |
| 9-3 | 4.62(2H, s), 6.26(1H, s), 6.97(1H, d, J=8.7 Hz), 7.17(1H, d, J=6.7 Hz), 7.40(1H, d, J=9.0 Hz), 7.67(1H, dd, J=8.7, 2.6 Hz), 8.42(1H, d, J=2.6 Hz). |
| 9-4 | 4.63(2H, s), 6.25(1H, s), 6.63(1H, dd, J=1.9, 7.9 Hz), 6.83(1H, d, J=8 Hz), 7.21(1H, d, J=6.6 Hz), 7.40(1H, d, J=8.9 Hz), 7.79(1H, dd, J=7.7, 15.6 Hz). |
| 9-5 | 4.62(2H, s), 6.27(1H, s), 6.87(1H, m), 7.06(1H, m), 7.22(1H, m), 7.41(1H, m), 7.66(1H, m). |
| 9-6 | 4.65(2H, s), 6.26(1H, s), 7.23(1H, d, J=6.6 Hz), 7.41(1H, d, J=9.0 Hz), 7.55(1H, m). |
| 9-7 | 4.64(2H, s), 6.23(1H, s), 7.12(1H, dd, J=7.5, 5.0 Hz), 7.22(1H, d, J=6.7 Hz), 7.39(1H, d, J=9.0 Hz), 7.99(1H, dd, J=7.5, 1.0 Hz), 8.23(1H, dd, J=5.0, 1.0 Hz). |
| 9-8 | 4.61(2H, s), 6.28(1H, s), 7.23(3H, m), 7.43(1H, d, J=9 Hz), 8.27(1H, m). |
| 9-9 | 4.63(2H, s), 6.26(1H, s), 7.15(1H, dd, J=5.2, 7.1 Hz), 7.26(1H, d, J=6.4 Hz), 7.42(1H, d, J=8.9 Hz), 8.04(1H, d, J=7.1 Hz), 8.29(1H, d, J=3.8 Hz). |
| 9-10 | 4.64(2H, s), 6.27(1H, s), 7.13(1H, d, J=8.6 Hz), 7.2(1H, d, J=6.6 Hz), 7.43(1H, d, J=9 Hz), 7.97(1H, dd, J=2.3, 8.6 Hz), 8.41(1H, m). |
| 9-11 | 4.64(2H, s), 6.27(1H, s), 7.16(1H, d, J=9 Hz), 7.23(1H, d, J=6.6 Hz), 7.44(1H, d, J=8.8 Hz), 8.52(1H, dd, J=2.8, 9.1 Hz), 8.99(1H, d, J=2.2 Hz). |
| 9-12 | 4.64(2H, s), 6.25(1H, s), 7.13(1H, m), 7.13(1H, dd, J=9.4, 9.3 Hz), 7.24(1H, dd, J=7.5 7.4 Hz), 7.99(1H, m), 8.24(1H, m). |
| 9-13 | 1.34(3H, t), 3.56(2H, q), 4.61(2H, br.s), 6.27(1H, s), 7.22–7.27(2H, m), 7.43(1H, d), 8.31(1H, d), 8.36(1H, m). |
| 9-14 | 2.67(3H, s), 4.99(2H, s), 6.24(1H, s), 7.53(1H, d, J=6.3 Hz), 7.56(1H, d, J=8.7 Hz). |
| 9-15 | 4.66(2H, s), 6.23(1H, s), 6.98(2H, m), 7.18(1H, d, J=6.8 Hz), 7.38(1H, d, J=9.1 Hz), 7.70(1H, m), 8.07(1H, m). |
| 9-16 | 5.36(2H, s), 6.31(1H, s), 7.33(1H, t, J=4.8 Hz), 7.55(1H, d, J=6.9 Hz), 7.69(1H, d, J=9.3 Hz), 8.68(2H, d, J=4.8 Hz). |
| 9-17 | 5.04(2H, s), 6.23(1H, s), 7.03(1H, d, J=5.6 Hz), 7.34(1H, d, J=6.6 Hz), 7.48(1H, d, J=8.9 Hz), 8.55(1H, d, J=5.6 Hz). |
| 9-18 | 3.82(6H, s), 4.66(2H br s), 5.79(1H, s), 6.24(1H, s), 7.19(1H, d, J=6.7 Hz), 7.39(1H, d, J=9.0 Hz). |
| 9-19 | 3.33(3H, s), 5.61(2H, br.s), 6.43(1H, s), 7.44~7.48(1H, m), 7.69(1H, d,) 7.96(1H, d), 8.38(1H, d), 8.47(1H, d). |
| 9-20 | 1.30(6H, d), 3.87(1H, m), 5.50(2H, br.s), 6.27(1H, s), 7.40(1H, d), 7.56(1H, d), 7.73(1H, d), 7.35(1H, d), 7.43(1H, d). |
| 9-21 | 4.60(2H, s), 6.26(1H, s), 6.96(1H, d, J=7.5 Hz), 7.03(1H, d, J=5.8 Hz), 7.25(1H, t, J=7.9 Hz), 7.46(1H, d, J=8.8 Hz), 7.54(1H, ddd, J=7.9, 7.5, 1.4 Hz), 7.98(1H, d, J=7.9, 1.4 Hz). |
| 9-22 | 4.61(2H, s), 6.28(1H, s), 6.87(1H, d, J=9.2 Hz), 7.20(1H, d, J=6.5 Hz), 7.51(1H, d, J=8.7 Hz), 8.35(1H, dd, J=9.2, 2.8 Hz), 8.61(1H, d, J=2.8 Hz). |
| 9-23 | 4.60(2H, s), 6.28(1H, s). 7.15(1H, d, J=6.4 Hz), 7.51(1H, d, J=8.8 Hz), 7.57(1H, br s), 7.95(1H, t, J=2.2 Hz), 8.24(1H, br s). |
| 9-24 | 4.58(2H, s), 6.25(1H, s), 6.85(1H, d, J=8.4 Hz), 6.99(1H, d, J=6.5 Hz), 7.19(1H, t, J=7.7 Hz), 7.44(1H, d, J=8.8 Hz), 7.47(1H, t, J=7.4 Hz), 7.70(1H, d, J=7.7 Hz). |
| 9-25 | 4.60(2H, s), 6.26(1H, s), 6.96(1H, d, J=6.5 Hz), 7.13(1H, dd, J=8.1, 1.9 Hz), 7.30(1H, br s), 7.38(1H, d, J=7.7 Hz), 7.44(1H, d, J=8.9 Hz), 7.46(1H, t, J=8.0 Hz). |
| 9-26 | 4.58(2H, s), 6.23(1H, s), 6.86(1H, d, J=6.7 Hz), 7.02(2H, ddd, J=8.7, 2.0, 1.1 Hz), 7.14(1H, tt, J=7.5, 1.1 Hz), 7.36(2H, ddt, J=8.7, 7.5, 2.0 Hz), 7.40(1H, d, J=8.9 Hz). |
| 9-27 | 1.25(3H, t, J=7.14 Hz), 1.60(3H, d, J=6.81 Hz), 4.21(2H, q, J=7.14 Hz), 4.55(2H, s), 4.67(1H, q, J=6.09 Hz), 6.21(1H, s), 6.72(1H, d, J=6.51 Hz), 6.82(2H, d, J=6.75), 6.95(2H, d, J=6.54 Hz), 7.36(1H, d, J=8.94 Hz). |
| 9-28 | 4.62(2H, s), 6.94(2H, m), 7.14(1H, m), 7.39(1H, m), 7.66(1H, m), 8.07(1H, m). |
| 9-29 | 4.66(2H, s), 6.95(1H, s), 7.21(2H, m), 7.40(1H, m), 8.31(1H, m), 8.41(1H, m). |
| 9-30 | 4.59(2H, s), 6.27(1H, s), 6.79(1H, d, J=8.5 Hz), 7.12(1H, d, J=6.5 Hz), 7.17(1H, dt, J=7.6, 0.9 Hz), 7.45(1H, d, J=8.8 Hz), 7.50(1H, ddd, J=8.5, 7.6, 1.6 Hz), 7.68(1H, dd, J=7.6, 1.6 Hz). |
| 9-31 | 4.59(2H, s), 6.28(1H, s), 6.55(1H, d, J=8.5 Hz), 6.94(1H, t, J=8.5 Hz), 7.18(1H, d, J=6.6 Hz), 7.43–7.49(2H, m). |

The compounds of the present invention exhibit excellent herbicidal effects when used as an active ingredient (ai) of a herbicide. The herbicide can sometimes be used for a wide range of applications, for example on crop lands such as paddy fields, upland farms, orchards and mulberry fields, and non-crop lands such as forests, farm roads, playgrounds, and factory sites. The application method may be suitably selected for soil treatment application and foliar application.

The compounds of the present invention are capable of controlling noxious weeds including grass (gramineae) such as barnyardgrass (*Echinochloa crus-galli*), large crabgrass (*Digilaria sanguinalis*), green foxtail (*Setaria viridis*), goosegrass (*Eleusine indica* L.), wild oat (*Avena fatua* L.), Johnsongrass (*Sorghum halepense*), quackgrass (*Agropyron repens*), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), Japanese bulrush (*Scirpus Juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and narrowleaf waterplantain (*Alisma canaliculatum*); ponted-eriaceae such as monochoria (*Monochoria vaginalis*) and monochoria species (*Monochoria korsakowii*); scrophulari-aceae such as false pimpernel (*Lindernia pyxidaria*) and abunome (*Dopatriuni Junceum*); lythraceae such as tooth-cup (*Rotala indica*) and red stem (*Ammannia multiflora*);

and broadleaves such as redroot pigweed (*Amaranthus retroflexus*), velvetleaf (*Abutilon theophrasti*), momingglory (*Ipomoea hederacea*), lambsquarters (*Chenopodium album*), prickly sida (*Sida spinosa* L.), common pursiane (*Portulaca oleracea* L.), slender amaranth (*Amaranthus viridis* L.), sicklepod (*Cassia obtusifolia*), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). Accordingly, it is useful for controlling noxious weeds non-selectively or selectively in the cultivation of a crop plant such as corn (*Zea mays* L.), soybean (*Glycine max* Merr.), cotton (Gossypium spp.), wheat (Triticum spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica stend*), peanut (*Arachis hypogaea* L.) or flax (*Linum usitatissimum* L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the fornation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

Now, Formulation Examples of the present invention will be given as follows.

| Formulation example 1. Emulsifiable Concentrate | | | | |
|---|---|---|---|---|
| Ingredient Trade Name | Chemical Name | Supplier | Function | % wt./wt. |
| Compound 6-10 | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |

| Formulation example 2. Suspension Concentrate | | | | |
|---|---|---|---|---|
| Ingredient Trade Name | Chemical Name | Supplier | Function | % wt./wt. |
| Compound 8-29 | | | Active Ingredient | 10.00 |
| Proylene gylcol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D-425 | Napthalene formaldehyde condensate | Witco Corp. | Dispersant | 3.00 |
| Igepal CA-720 | Octylphenol ethoxylate | Rhone-Poulenc | Wetting agent | 3.00 |
| Proxel GXL | 1,2 benzisothiazolin-3-one | ICI Americas | Preservative | 0.25 |
| Water | | | Diluent | 68.00 |

| Formulation example 3. Wettable Powder | | | | |
|---|---|---|---|---|
| Ingredient Trade Name | Chemical Name | Supplier | Function | % wt./wt. |
| Compound 8-29 | | | Active Ingredient | 50.00 |
| Geropon T-77 | Sodium-N-methyl-N-oleoyl taurate | Rhone-Poulenc | Wetting agent | 3.00 |
| Lomar PW | Naphthalene Sulfonate | Henkel Corp. | Dispersant | 5.00 |
| Kaolin clay | Kaolin clay | J. M. Huber | Filler | 42.00 |

Formulation example 4. Water Dispersible Granule

| Ingredient Trade Name | Chemical Name | Supplier | Function | % wt./wt. |
|---|---|---|---|---|
| Compound 6-10 | | | Active Ingredient | 50.00 |
| Morwet EFW | | Witco Corp. | Wetting agent | 2.00 |
| Morwet D-425 | Naphthalene formaldehyde condensate | Witco Corp. | Dispersant | 10.00 |
| ASP 400 | Kaolin Clay | Engelhard Corp. | Filler | 38.00 |

Test Example

A standard greenhouse herbicide activity screening system was used to evaluate the herbicidal efficacy and crop safety of these test compounds. Six broadleaf weed species including redroot pigweed (*Amaranthus retroflexus*, AMARE), velvetleaf (*Abutilon theophrasti*, ABUTH), sicklepod (*Cassia obtusifolia*, CASOB), ivyleaf morningglory (*Ipomoea hederacea*, IPOHE), lambsquarters (*Chenopodium album*, CHEAL) and common ragweed (*Ambrosia artemisiifolia* L., AMBEL) were used as test species. Four grass weed species including green foxtail (*Setaria viridis*, SETVI), barnyardgrass (*Echinociloa crusgalli*, ECHCG), Johnsongrass (*Sorghum halepense*, SORHA), and large crabgrass (*Digitaria sanguinalis*, DIGSA) were also used. In addition, three crop species, field corn (*Zea mays* L., var. Dekalb 535, CORN), soybean (*Glycine max* L., var. Pella 86, SOY), and upland rice (Oryza sp., var.Tebonnet, RICE) were included.

Test Example 1. Pre-emerge test

All plants were grown in 10 cm square plastic pots which were filled with a sandy loam soil mix. For pre-emerge tests, seeds were planted one day prior to application of the test compounds. Immediately after application, test units of the pre-emerge applications were watered at the soil surface to incorporate the test materials. Subsequently, these test units were bottom-watered.

All test compounds were dissolved in acetone and applied to the test units in a volume of 187 l/ha. Test materials were applied at rates ranging from 125 g ai/ha to 1000 g ai/ha using a track sprayer equipped with a TJ8001E even flow flat fan spray nozzle. Plants were arranged on a shelf so that the top of the canopy (post-emerge) or top of the soil surface (pre-emerge) was 40–45 cm below the nozzle. Pressurized air was used to force the test solution through the nozzle as it was mechanically advanced (via electrically driven chain drive) over the top of all test plants/pots. This application simulates a typical commercial field herbicide application.

Test Example 2. Post-emerge test

In the post-emerge test, a commercial non-ionic surfactant was also included (0.25% v/v) to enhance wetting of the leaf surfaces of target plants at rates ranging from 63 g ai/ha to 1000 g ai/ha. For post-emerge tests, seeds were planted 8–21 days prior to the test to allow emergence and good foliage development prior to application of the test substances. At the time of the post-emerge application, plants of all species were usually at the 2–3 leaf stage of development. Post-emerge test units were always bottom-watered.

At 14 days after application of the test materials, phytotoxicity ratings were recorded. A rating scale of 0–100 was used as previously described in *Research Methods in Weed Science*, 2nd edition, B. Truelove, Ed., Southern Weed Science Society, Auburn University, Auburn, 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound number in Tables 1–9, are shown in Tables 13 and 14. The data demonstrate significant differences between compounds for both efficacy against weeds and selectivity for crop species. For selected compounds, excellent activity against a majority of the weed species was observed with minimal damage to at least one of the crop species.

TABLE 13

Pre-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-1 | 125 | — | — | — | — | — | — | — | — | — | — | — | — | — |
|  | 500 | 100 | 60 | 20 | 10 | 100 | 50 | 100 | 50 | 70 | 90 | 10 | 20 | 20 |
| 1-2 | 125 | 80 | 0 | 80 | 0 | 50 | 80 | 90 | 20 | 30 | 40 | 0 | 10 | 30 |
|  | 500 | 100 | 70 | 0 | 60 | 99 | 80 | 99 | 50 | 50 | 95 | 10 | 90 | 40 |
| 1-3 | 125 | 100 | 20 | 0 | 0 | 90 | 50 | 95 | 0 | 0 | 20 | 0 | 0 | 0 |
|  | 500 | 100 | 0 | 80 | 30 | 100 | 50 | — | 100 | 40 | 0 | 95 | 40 | 30 |
| 1-4 | 125 | 100 | 0 | 0 | 0 | 90 | 0 | 90 | 0 | 20 | 50 | 10 | 10 | 30 |
|  | 500 | 100 | 80 | 0 | 30 | 95 | 20 | 99 | 0 | 20 | 95 | 50 | 0 | 0 |
| 1-5 | 125 | 100 | 70 | 50 | 30 | 100 | 50 | 100 | 50 | 50 | 100 | 0 | 20 | 30 |
|  | 500 | 100 | 90 | 100 | 70 | 100 | 90 | 100 | 90 | 95 | 90 | 0 | 30 | 20 |
| 1-6 | 125 | 95 | 50 | 0 | 30 | 40 | 100 | 60 | 30 | 0 | 20 | 0 | 0 | 0 |
|  | 500 | 99 | 80 | 0 | 50 | 99 | 100 | 99 | 30 | 70 | 90 | 10 | 0 | 0 |

TABLE 13-continued

Pre-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-7 | 125 | 100 | 90 | 95 | 40 | 100 | 100 | 100 | 100 | 100 | 100 | 0 | 40 | 70 |
|  | 500 | 100 | 99 | 90 | 70 | 100 | 100 | 100 | 100 | 100 | 100 | 0 | 70 | 90 |
| 1-8 | 125 | 70 | 0 | 0 | 0 | 0 | 0 | 50 | 0 | 0 | 20 | 0 | 0 | 0 |
|  | 500 | 100 | 20 | 0 | 0 | 100 | 10 | 100 | 0 | 35 | 90 | 0 | 0 | 10 |
| 2-1 | 125 | 100 | 0 | 0 | 10 | 60 | 0 | 90 | 0 | 0 | 0 | 0 | 0 | 0 |
|  | 500 | 100 | 30 | 30 | 10 | 100 | 50 | 99 | 20 | 30 | 70 | 70 | 0 | 0 |
| 2-2 | 125 | — | — | — | — | — | — | — | — | — | — | — | — | — |
|  | 500 | 100 | 10 | 0 | 60 | 60 | 20 | 100 | 0 | 30 | 20 | 15 | 0 | 0 |
| 2-3 | 125 | 100 | 100 | 30 | 20 | 100 | 35 | 95 | 80 | 100 | 100 | 50 | 25 | 30 |
|  | 500 | 100 | 100 | 100 | 100 | 100 | 90 | 100 | 100 | 100 | 100 | 25 | 35 | 55 |
| 2-4 | 125 | 70 | 10 | 0 | 10 | 70 | 10 | 20 | 0 | 0 | 0 | 0 | 0 | 0 |
|  | 500 | 100 | 70 | 10 | 0 | 100 | 0 | 95 | 0 | 40 | 50 | 20 | 0 | 0 |
| 3-1 | 125 | 100 | 100 | 100 | 100 | 100 | 100 | 100 | 100 | 100 | 100 | 90 | 90 | 99 |
|  | 500 | 100 | 100 | 100 | 100 | 100 | 100 | 100 | 100 | 100 | 100 | 100 | 100 | 100 |
| 4-2 | 125 | — | — | — | — | — | — | — | — | — | — | — | — | — |
|  | 500 | 100 | 95 | 0 | 0 | 100 | 100 | 40 | 0 | 0 | 0 | 0 | 0 | 0 |
| 5-1 | 125 | — | — | — | — | — | — | — | — | — | — | — | — | — |
|  | 1000 | 99 | 100 | 40 | 70 | 100 | — | 99 | 95 | 90 | 100 | 55 | 5 | 70 |
| 5-2 | 125 | — | — | — | — | — | — | — | — | — | — | — | — | — |
|  | 1000 | 40 | 100 | 0 | 50 | 100 | — | 90 | 50 | 80 | 70 | 10 | 0 | 50 |
| 5-3 | 125 | — | — | — | — | — | — | — | — | — | — | — | — | — |
|  | 1000 | 100 | 99 | 10 | 0 | 0 | — | 20 | 0 | 40 | 70 | 40 | 0 | 20 |
| 5-5 | 125 | — | — | — | — | — | — | — | — | — | — | — | — | — |
|  | 500 | 95 | 50 | 0 | 0 | 100 | — | 0 | 0 | 0 | 0 | 10 | 0 | 0 |
| 5-6 | 125 | — | — | — | — | — | — | — | — | — | — | — | — | — |
|  | 1000 | 100 | 100 | 40 | 100 | 100 | — | 100 | 70 | 50 | 70 | 60 | 40 | 80 |
| 5-8 | 125 | — | — | — | — | — | — | — | — | — | — | — | — | — |
|  | 1000 | 100 | 100 | 0 | 80 | 100 | — | 95 | 85 | 95 | 100 | 50 | 15 | 50 |
| 5-9 | 125 | — | — | — | — | — | — | — | — | — | — | — | — | — |
|  | 1000 | 80 | 100 | 30 | 100 | 100 | — | 90 | 0 | 90 | 90 | 50 | 0 | 50 |
| 5-10 | 125 | — | — | — | — | — | — | — | — | — | — | — | — | — |
|  | 1000 | 100 | 100 | 0 | 100 | 100 | — | 100 | 100 | 100 | 100 | 80 | 70 | 80 |
| 5-11 | 125 | — | — | — | — | — | — | — | — | — | — | — | — | — |
|  | 1000 | 80 | 100 | 30 | 80 | 100 | — | 95 | 95 | 99 | 90 | 60 | 30 | 80 |
| 5-12 | 125 | 100 | 100 | 50 | 80 | 100 | — | 100 | 20 | 40 | 100 | 40 | 10 | 60 |
|  | 500 | 100 | 100 | 100 | 100 | 100 | — | 100 | 100 | 100 | 100 | 80 | 40 | 100 |
| 6-2 | 125 | 95 | 90 | 20 | 10 | 100 | 30 | 30 | 0 | 0 | 0 | 10 | 0 | 20 |
|  | 500 | 99 | 100 | 0 | 40 | 100 | 40 | 70 | 10 | 0 | 60 | 15 | 0 | 10 |
| 6-3 | 125 | 0 | 40 | 30 | 0 | 0 | 100 | 99 | 60 | 30 | 10 | 0 | 30 | 20 |
|  | 500 | 90 | 30 | 40 | 20 | 90 | 40 | 70 | 0 | 0 | 50 | 0 | 10 | 20 |
| 6-4 | 125 | 100 | 100 | 50 | 40 | 100 | 0 | 100 | 0 | 20 | 70 | 0 | 0 | 15 |
|  | 500 | 100 | 100 | 30 | 100 | 100 | 40 | 100 | 95 | 100 | 100 | 20 | 10 | 35 |
| 6-5 | 125 | 90 | 0 | 70 | 40 | 90 | 0 | 95 | 0 | 30 | 30 | 10 | 20 | 20 |
|  | 500 | 100 | 90 | 50 | 40 | 100 | 50 | 100 | 0 | 70 | 70 | 0 | 20 | 10 |
| 6-6 | 125 | 95 | 80 | 10 | 30 | 100 | 30 | 95 | 20 | 30 | 20 | 0 | 0 | 0 |
|  | 500 | 100 | 100 | 0 | 50 | 100 | 60 | 100 | 60 | 95 | 100 | 10 | 0 | 30 |
| 6-7 | 125 | 80 | 0 | 0 | 0 | 80 | 30 | 80 | 0 | 20 | 40 | 80 | 0 | 0 |
|  | 500 | 100 | 20 | 60 | 30 | 90 | 0 | 100 | 50 | 40 | 70 | 90 | 30 | 40 |
| 6-8 | 125 | — | — | — | — | — | — | — | — | — | — | — | — | — |
|  | 500 | 85 | 80 | 0 | 0 | 100 | 0 | 100 | 0 | 80 | 75 | 0 | 0 | 10 |
| 6-9 | 125 | 0 | 0 | 0 | 0 | 0 | 0 | 0 | 0 | 0 | 0 | 0 | 0 | 0 |
|  | 500 | 0 | 0 | 0 | 0 | 0 | 0 | 0 | 0 | 0 | 0 | 0 | 0 | 0 |
| 6-10 | 125 | 100 | 100 | 40 | 100 | 100 | 100 | 100 | 100 | 100 | 100 | 0 | 70 | 80 |
|  | 500 | 100 | 100 | 100 | 100 | 100 | 100 | 100 | 100 | 100 | 100 | 20 | 90 | 100 |
| 6-14 | 125 | 100 | 100 | 60 | 60 | 100 | 20 | 100 | 60 | 80 | 90 | 10 | 20 | 30 |
|  | 500 | 100 | 100 | 90 | 95 | 100 | 95 | 100 | 99 | 100 | 100 | 80 | 40 | 80 |
| 6-15 | 125 | 30 | 20 | 0 | 0 | 20 | 0 | 10 | 0 | 0 | 10 | 0 | 0 | 0 |
|  | 500 | 100 | 100 | 30 | 10 | 100 | 0 | 90 | 0 | 10 | 60 | 0 | 10 | 10 |
| 6-16 | 125 | 100 | 100 | 50 | 50 | 100 | 0 | 80 | 0 | 40 | 80 | 0 | 0 | 0 |
|  | 500 | 100 | 100 | 30 | 30 | 100 | 70 | 100 | 90 | 80 | 100 | 10 | 15 | 50 |
| 6-17 | 125 | 0 | 0 | 0 | 0 | 0 | 0 | 0 | 0 | 0 | 0 | 0 | 0 | 0 |
|  | 500 | 0 | 0 | 0 | 0 | 0 | 0 | 0 | 0 | 0 | 0 | 0 | 0 | 0 |
| 7-1 | 125 | 100 | 90 | 50 | 0 | 100 | 80 | 90 | 0 | 0 | 60 | 10 | 0 | 0 |
|  | 500 | 100 | 100 | 10 | 0 | 100 | 90 | 100 | 0 | 60 | 90 | 20 | 10 | 20 |
| 7-2 | 125 | 100 | 100 | 60 | 100 | 100 | 100 | 100 | 99 | 95 | 100 | 0 | 45 | 90 |
|  | 500 | 100 | 100 | 100 | 100 | 100 | 100 | 100 | 100 | 100 | 100 | 80 | 70 | 100 |
| 8-1 | 125 | — | — | — | — | — | — | — | — | — | — | — | — | — |
|  | 500 | 100 | 95 | 70 | 30 | 100 | — | 85 | 40 | 60 | 100 | 0 | 0 | 30 |
| 8-2 | 125 | 100 | 100 | 0 | 100 | 100 | 95 | 95 | 10 | 20 | 90 | 0 | 0 | 40 |
|  | 500 | 100 | 100 | 80 | 90 | 100 | 100 | 100 | 100 | 100 | 100 | 20 | 50 | 90 |
| 8-3 | 125 | 10 | 20 | 0 | 10 | 80 | 20 | 0 | 0 | 0 | 0 | 0 | 0 | 0 |
|  | 500 | 100 | 70 | 0 | 60 | 100 | 60 | 70 | 10 | 40 | 90 | 10 | 5 | 30 |
| 8-4 | 125 | 100 | 100 | 30 | 0 | 70 | 20 | 50 | 10 | 20 | 30 | 0 | 0 | 0 |
|  | 500 | 100 | 100 | 90 | 0 | 100 | 0 | 100 | 30 | 70 | 90 | 0 | 0 | 30 |

TABLE 13-continued

Pre-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 8-5 | 125 | 95 | 100 | 30 | 0 | 100 | 40 | 80 | 0 | 20 | 40 | 0 | 0 | 0 |
|  | 500 | 100 | 100 | 95 | 70 | 100 | 100 | 100 | 60 | 30 | 85 | 40 | 5 | 25 |
| 8-6 | 125 | 100 | 100 | 100 | 50 | 100 | 40 | 95 | 20 | 20 | 40 | 20 | 0 | 10 |
|  | 500 | 100 | 100 | 95 | 90 | 100 | 100 | 100 | 50 | 50 | 100 | 40 | 0 | 40 |
| 8-7 | 125 | 90 | 100 | 70 | 30 | 100 | 70 | 70 | 100 | 20 | 60 | 0 | 0 | 20 |
|  | 500 | 100 | 100 | 100 | 100 | 100 | 100 | 90 | 100 | 70 | 99 | 20 | 10 | 50 |
| 8-8 | 125 | 100 | 90 | 0 | 0 | 0 | 0 | 60 | 0 | 30 | 40 | 0 | 5 | 0 |
|  | 500 | 100 | 100 | 80 | 10 | 10 | 20 | 95 | 20 | 30 | 40 | 20 | 0 | 0 |
| 8-9 | 125 | 100 | 60 | 0 | 0 | 70 | 30 | 0 | 0 | 0 | 0 | 0 | 0 | 0 |
|  | 500 | 95 | 100 | 40 | 10 | 100 | 30 | 30 | 0 | 0 | 0 | 0 | 0 | 0 |
| 8-11 | 125 | 100 | 100 | 70 | 70 | 100 | 95 | 90 | 60 | 70 | 20 | 20 | 0 | 50 |
|  | 500 | 100 | 100 | 60 | 100 | 100 | 100 | 100 | 70 | 40 | 80 | 30 | 0 | 80 |
| 8-12 | 125 | 90 | 95 | 0 | 0 | 100 | 90 | 0 | 0 | 0 | 0 | 0 | 0 | 20 |
|  | 500 | 100 | 100 | 0 | 70 | 100 | 90 | 70 | 0 | 40 | 50 | 0 | 0 | 50 |
| 8-14 | 125 | 70 | 30 | 0 | 0 | 80 | 0 | 0 | 0 | 0 | 0 | 0 | 0 | 0 |
|  | 500 | 95 | 60 | 0 | 0 | 100 | 30 | 50 | 0 | 0 | 20 | 0 | 0 | 0 |
| 8-15 | 125 | 0 | 0 | 0 | 0 | 0 | 0 | 0 | 0 | 0 | 0 | 0 | 0 | 0 |
|  | 500 | 40 | 50 | 0 | 0 | 100 | 0 | 0 | 0 | 0 | 0 | 0 | 0 | 0 |
| 8-16 | 125 | 80 | 90 | 0 | 0 | 100 | 40 | 0 | 0 | 0 | 0 | 0 | 0 | 0 |
|  | 500 | 90 | 100 | 0 | 0 | 100 | 100 | 70 | 0 | 10 | 30 | 10 | 0 | 0 |
| 8-17 | 125 | 100 | 100 | 100 | 80 | 100 | 100 | 100 | 85 | 50 | 100 | 0 | 10 | 50 |
|  | 500 | 100 | 100 | 80 | 99 | 100 | 100 | 100 | 100 | 100 | 100 | 95 | 30 | 95 |
| 8-18 | 125 | 100 | 100 | 20 | 20 | 100 | 100 | 95 | 40 | 40 | 50 | 15 | 0 | 35 |
|  | 500 | 100 | 100 | 40 | 45 | 100 | 95 | 100 | 80 | 100 | 100 | 30 | 60 | 80 |
| 8-19 | 125 | 100 | 100 | 20 | 40 | 100 | 50 | 100 | 50 | 80 | 50 | 20 | 15 | 50 |
|  | 500 | 100 | 100 | 100 | 90 | 100 | 100 | 100 | 95 | 95 | 100 | 40 | 30 | 80 |
| 8-20 | 125 | 100 | 100 | 90 | 95 | 100 | 90 | 95 | 60 | 40 | 40 | 20 | 5 | 20 |
|  | 500 | t00 | 100 | 100 | 100 | 100 | 100 | 100 | 80 | 90 | 100 | 25 | 10 | 40 |
| 8-21 | 125 | 100 | 100 | 70 | 90 | 100 | 70 | 99 | 40 | 80 | 70 | 0 | 0 | 40 |
|  | 500 | 100 | 100 | 100 | 100 | 100 | 90 | 100 | 90 | 100 | 100 | 80 | 10 | 95 |
| 8-22 | 125 | 100 | 100 | 20 | 40 | 100 | 100 | 40 | 0 | 0 | 20 | 50 | 0 | 0 |
|  | 500 | 100 | 100 | 90 | 10 | 100 | 100 | 100 | 30 | 20 | 90 | 70 | 60 | 40 |
| 8-23 | 125 | 90 | 95 | 0 | 30 | 100 | 0 | 10 | 0 | 0 | 0 | 0 | 0 | 0 |
|  | 500 | 100 | 100 | 50 | 60 | 100 | 60 | 100 | 10 | 30 | 50 | 20 | 0 | 0 |
| 8-24 | 125 | 95 | 100 | 70 | 0 | 99 | 80 | 30 | 0 | 20 | 0 | 0 | 0 | 0 |
|  | 500 | 100 | 100 | 50 | 70 | 100 | 100 | 80 | 40 | 20 | 30 | 30 | 0 | 20 |
| 8-25 | 125 | 100 | 100 | 70 | 20 | 100 | 40 | 100 | 40 | 70 | 85 | 0 | 0 | 15 |
|  | 500 | 100 | 100 | 100 | 20 | 100 | 90 | 100 | 100 | 90 | 100 | 20 | 40 | 70 |
| 8-26 | 125 | — | — | — | — | — | — | — | — | — | — | — | — | — |
|  | 500 | 0 | 0 | 0 | 0 | 0 | 0 | 0 | 0 | 0 | 0 | 0 | 0 | 0 |
| 8-27 | 125 | 100 | 50 | 0 | 0 | 80 | 0 | 60 | 0 | 0 | 10 | 0 | 0 | 0 |
|  | 500 | 100 | 100 | 80 | 30 | 100 | 0 | 100 | 0 | 30 | 50 | 0 | 0 | 10 |
| 8-28 | 125 | 100 | 100 | 100 | 30 | 100 | 80 | 100 | 60 | 90 | 100 | 10 | 15 | 25 |
|  | 500 | 100 | 100 | 90 | 40 | 100 | 100 | 100 | 95 | 95 | 100 | 10 | 15 | 70 |
| 8-29 | 125 | 100 | 100 | 100 | 100 | 100 | 100 | 100 | 100 | 100 | 100 | 90 | 80 | 90 |
|  | 500 | 100 | 100 | 100 | 100 | 100 | 100 | 100 | 100 | 100 | 100 | 100 | 95 | 100 |
| 8-30 | 125 | 100 | 100 | 100 | 100 | 100 | 100 | 100 | 40 | 40 | 70 | 80 | 10 | 20 |
|  | 500 | 100 | 100 | 100 | 90 | 100 | 99 | 100 | 99 | 99 | 100 | 80 | 20 | 90 |
| 8-31 | 125 | 100 | 100 | 30 | 0 | 90 | 30 | 0 | 0 | 0 | 0 | 40 | 0 | 0 |
|  | 500 | 100 | 100 | 90 | 70 | 100 | 0 | 90 | 20 | 20 | 70 | 0 | 0 | 10 |
| 8-32 | 125 | 50 | 95 | 30 | 40 | 90 | 0 | 10 | 0 | 10 | 20 | 0 | 0 | 0 |
|  | 500 | 100 | 100 | 80 | 90 | 100 | 50 | 100 | 20 | 30 | 90 | 0 | 10 | 40 |
| 8-33 | 125 | 100 | 100 | 40 | 0 | 100 | 0 | 80 | 0 | 0 | 10 | 0 | 0 | 10 |
|  | 500 | 100 | 100 | 90 | 70 | 100 | 40 | 100 | 20 | 40 | 90 | 30 | 0 | 10 |
| 8-34 | 125 | 100 | 100 | 0 | 0 | 100 | 40 | 80 | 0 | 20 | 10 | 10 | 0 | 20 |
|  | 500 | 100 | 100 | 40 | 80 | 100 | 100 | 99 | 40 | 80 | 80 | 0 | 5 | 50 |
| 8-35 | 125 | 100 | 100 | 30 | 50 | 100 | 50 | 90 | 10 | 20 | 10 | 0 | 0 | 30 |
|  | 500 | 100 | 100 | 100 | 100 | 100 | 90 | 100 | 90 | 90 | 80 | 30 | 30 | 70 |
| 8-36 | 125 | 100 | 100 | 90 | 90 | 100 | 90 | 80 | 0 | 20 | 70 | 0 | 0 | 30 |
|  | 250 | 100 | 100 | 70 | 70 | 100 | 100 | 99 | 70 | 50 | 80 | 100 | 20 | 70 |
| 8-37 | 125 | 100 | 100 | 0 | 30 | 100 | 100 | 100 | 30 | 20 | 80 | 50 | 0 |  |
|  | 500 | 100 | 100 | 80 | 85 | 100 | 100 | 100 | 100 | 80 | 100 | 80 | 25 | 80 |
| 8-38 | 125 | 30 | 100 | 0 | 0 | 80 | 0 | 0 | 0 | 0 | 0 | 0 | 0 |  |
|  | 250 | 80 | 100 | 0 | 30 | 90 | 0 | 70 | 0 | 0 | 0 | 0 | 0 | 0 |
| 8-39 | 125 | 100 | 20 | 95 | 0 | 99 | — | 0 | 0 | 0 | 0 | 0 | 0 | 0 |
|  | 250 | 100 | 100 | 0 | 0 | 100 | — | 40 | 0 | 0 | 0 | 0 | 0 | 20 |
| 8-40 | 125 | 60 | 50 | 0 | 0 | 50 | — | 0 | 0 | 0 | 0 | 0 | 0 | 0 |
|  | 250 | 100 | 30 | 20 | 0 | 100 | — | 0 | 0 | 0 | 0 | 0 | 0 | 0 |
| 8-41 | 125 | 80 | 0 | 0 | 0 | 70 | — | 10 | 0 | 0 | 0 | 0 | 0 | 0 |
|  | 250 | 100 | 70 | 0 | 0 | 90 | — | 50 | 0 | 0 | 0 | 0 | 0 | 0 |
| 8-42 | 125 | 100 | 100 | 100 | 30 | 80 | 0 | 0 | 0 | 0 | 0 | 0 | 0 | 0 |
|  | 250 | 100 | 100 | 80 | 50 | 100 | 30 | 0 | 0 | 0 | 0 | 20 | 0 | 0 |
| 8-43 | 125 | 20 | 10 | 20 | 0 | 100 | — | 100 | 0 | 0 | 90 | 0 | 0 | 20 |
|  | 250 | 70 | 30 | 30 | 20 | 100 | — | 100 | 0 | 0 | 100 | 0 | 0 | 20 |

TABLE 13-continued

Pre-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 9-1 | 125 | 100 | 100 | 30 | 100 | 100 | | 99 | 95 | 95 | 95 | 40 | 5 | 40 |
| | 500 | 100 | 100 | 90 | 100 | 100 | | 100 | 100 | 99 | 100 | 80 | 60 | 90 |
| 9-2 | 125 | 80 | 30 | 0 | 0 | 100 | | 80 | 20 | 60 | 95 | 0 | 0 | 10 |
| | 500 | 100 | 100 | 50 | 100 | 100 | | 100 | 95 | 90 | 100 | 80 | 70 | 60 |
| 9-3 | 125 | 100 | 100 | 0 | 40 | 100 | | 100 | 30 | 70 | 95 | 0 | 10 | 20 |
| | 500 | 100 | 100 | 70 | 100 | 100 | | 100 | 99 | 99 | 100 | 50 | 70 | 80 |
| 9-4 | 125 | 100 | 100 | 60 | 100 | 100 | | 100 | 100 | 99 | 100 | 80 | 60 | 40 |
| | 500 | 100 | 100 | 100 | 100 | 100 | | 100 | 100 | 100 | 100 | 95 | 95 | 99 |
| 9-5 | 125 | 100 | 100 | 10 | 70 | 100 | | 100 | 90 | 95 | 95 | 40 | 15 | 50 |
| | 500 | 100 | 100 | 80 | 80 | 100 | | 100 | 100 | 100 | 100 | 40 | 70 | 90 |
| 9-6 | 125 | 100 | 100 | 90 | 90 | 100 | | 100 | 90 | 90 | 100 | 20 | 50 | 50 |
| | 500 | 100 | 100 | 100 | 95 | 100 | | 100 | 100 | 90 | 100 | 75 | 70 | 85 |
| 9-7 | 125 | 100 | 100 | 40 | 70 | 100 | | 100 | 90 | 90 | 100 | 50 | 30 | 60 |
| | 500 | 100 | 100 | 100 | 100 | 100 | | 100 | 100 | 100 | 100 | 90 | 99 | 80 |
| 9-8 | 125 | 100 | 100 | 80 | 95 | 100 | | 40 | 30 | 50 | 20 | 60 | 50 | 50 |
| | 500 | 100 | 100 | 90 | 100 | 100 | | 100 | 99 | 99 | 100 | 50 | 70 | 80 |
| 9-9 | 125 | 100 | 100 | 100 | 100 | 100 | | 100 | 100 | 100 | 100 | 100 | 90 | 90 |
| | 500 | 100 | 100 | 100 | 100 | 100 | | 100 | 100 | 100 | 100 | 100 | 99 | 99 |
| 9-10 | 125 | 100 | 100 | 100 | 100 | 100 | | 100 | 90 | 95 | 90 | 100 | 80 | 50 |
| | 500 | 100 | 100 | 100 | 100 | 100 | | 100 | 100 | 100 | 100 | 100 | 90 | 90 |
| 9-11 | 125 | 100 | 100 | 10 | 10 | 100 | | 70 | 10 | 20 | 30 | 0 | 5 | 10 |
| | 500 | 100 | 100 | 20 | 100 | 100 | | 100 | 80 | 90 | 95 | 50 | 10 | 60 |
| 9-14 | 125 | 100 | 100 | 100 | 100 | 100 | | 100 | 95 | 95 | 100 | 80 | 80 | 65 |
| | 500 | 100 | 100 | 90 | 100 | 100 | | 100 | 90 | 100 | 100 | 15 | 40 | 50 |
| 9-15 | 125 | 100 | 100 | 95 | 100 | 100 | | 100 | 100 | 100 | 100 | 80 | 70 | 80 |
| | 500 | 100 | 100 | 100 | 100 | 100 | | 100 | 100 | 100 | 100 | 95 | 90 | 100 |
| 9-16 | 125 | 100 | 100 | 100 | 100 | 100 | | 100 | 100 | 100 | 100 | 100 | 100 | 100 |
| | 500 | 100 | 100 | 100 | 100 | 100 | | 100 | 100 | 100 | 100 | 100 | 100 | 100 |
| 9-17 | 125 | 100 | 100 | 20 | 20 | 100 | | 90 | 20 | 30 | 30 | 0 | 0 | 10 |
| | 500 | 100 | 100 | 70 | 100 | 100 | | 100 | 100 | 90 | 100 | 90 | 50 | 70 |
| 9-21 | 125 | 100 | 100 | 30 | 60 | 100 | | 100 | 90 | 90 | 100 | 30 | 25 | 80 |
| | 500 | 100 | 100 | 90 | 100 | 100 | | 100 | 100 | 100 | 100 | 90 | 60 | 90 |
| 9-22 | 125 | 100 | 100 | 30 | 90 | 100 | | 90 | 50 | 50 | 80 | 10 | 5 | 15 |
| | 500 | 100 | 100 | 80 | 80 | 100 | | 100 | 90 | 95 | 100 | 70 | 30 | 75 |
| 9-23 | 125 | 100 | 40 | 0 | 0 | 95 | | 40 | 10 | 10 | 10 | 10 | 10 | 10 |
| | 500 | 100 | 100 | 10 | 0 | 100 | | 100 | 70 | 70 | 95 | 15 | 5 | 60 |
| 9-24 | 125 | 95 | 99 | 30 | 30 | 100 | | 100 | 60 | 30 | 90 | 30 | 10 | 15 |
| | 500 | 100 | 100 | 0 | 30 | 100 | | 100 | 70 | 90 | 100 | 60 | 30 | 80 |
| 9-25 | 125 | 100 | 100 | 30 | 70 | 100 | | 100 | 70 | 80 | 80 | 50 | 20 | 40 |
| | 500 | 100 | 100 | 80 | 90 | 100 | | 100 | 95 | 100 | 100 | 80 | 40 | 90 |
| 9-26 | 125 | 100 | 100 | 95 | 100 | 100 | | 100 | 95 | 90 | 100 | 70 | 15 | 70 |
| | 500 | 100 | 100 | 100 | 60 | 100 | | 100 | 100 | 100 | 100 | 70 | 75 | 90 |
| 9-28 | 125 | 100 | 100 | 50 | 40 | 100 | | 100 | 20 | 20 | 70 | 20 | 0 | 10 |
| | 500 | 100 | 100 | 50 | 70 | 100 | | 100 | 80 | 80 | 100 | 50 | 60 | 50 |

TABLE 14

Post-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 1-1 | 63 | — | — | — | — | — | — | — | — | — | — | — | — | — |
| | 500 | 100 | 100 | — | 100 | 100 | 100 | 100 | 100 | 90 | 95 | 100 | 60 | 90 |
| 1-2 | 63 | 80 | 30 | — | 30 | 70 | 30 | 0 | 0 | 20 | 0 | 10 | 0 | 0 |
| | 500 | 100 | 100 | — | 90 | 100 | 90 | 40 | 80 | 40 | 50 | 50 | 10 | 0 |
| 1-3 | 63 | 100 | 70 | — | 90 | 95 | 0 | 0 | 0 | 20 | 0 | 30 | 0 | 20 |
| | 500 | 100 | 100 | — | 10 | 100 | 80 | 90 | 70 | 80 | 80 | 90 | 10 | 70 |
| 1-4 | 63 | 100 | 30 | — | 70 | 0 | 20 | 0 | 0 | 40 | 20 | 0 | 0 | 20 |
| | 500 | 100 | 90 | — | 100 | 100 | 70 | 70 | 50 | 80 | 40 | 80 | 0 | 50 |
| 1-5 | 63 | 100 | 30 | — | 95 | 95 | 30 | 0 | 30 | 30 | 50 | 40 | 10 | 40 |
| | 500 | 100 | 100 | — | 100 | 100 | 90 | 100 | 100 | 95 | 99 | 90 | 30 | 80 |
| 1-6 | 63 | 99 | 50 | — | 50 | 30 | 0 | 20 | 20 | 30 | 0 | 30 | 10 | — |
| | 500 | 100 | 100 | — | 100 | 100 | 90 | 60 | 70 | 70 | — | 50 | 10 | — |
| 1-7 | 63 | 100 | 100 | — | 100 | 100 | 95 | 100 | 100 | 90 | 90 | 100 | 90 | 100 |
| | 500 | 100 | 100 | 100 | 100 | 100 | 100 | 100 | 100 | 100 | 100 | 100 | 70 | 80 |
| 1-8 | 63 | 20 | 0 | 0 | 10 | 0 | 0 | 50 | 0 | 0 | 0 | 0 | 0 | 0 |
| | 500 | 100 | 35 | 10 | 80 | 95 | 10 | 20 | 0 | 10 | 20 | 20 | 20 | 0 |
| 2-1 | 63 | 90 | 40 | 0 | 60 | 80 | 10 | 30 | 0 | 0 | 0 | 50 | 15 | 0 |
| | 500 | 100 | 85 | 30 | 65 | 99 | 40 | 65 | 30 | 10 | 20 | 75 | 20 | 20 |

TABLE 14-continued

Post-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 2-2 | 63 | — | — | — | — | — | — | — | — | — | — | — | — | — |
|  | 500 | 95 | 70 | 0 | 75 | 90 | 25 | 30 | 30 | 40 | 10 | 35 | 20 | 40 |
| 2-3 | 63 | 100 | 95 | 30 | 100 | 90 | 30 | 100 | 30 | 80 | 0 | 90 | 30 | 40 |
|  | 500 | 100 | 100 | 70 | 100 | 100 | 60 | 100 | 95 | 95 | 80 | 90 | 80 | 90 |
| 2-4 | 63 | 0 | 0 | 0 | 0 | 0 | 0 | 0 | 0 | 0 | 0 | 0 | 0 | 0 |
|  | 500 | 90 | 80 | 0 | 75 | 70 | 0 | 50 | 0 | 50 | 10 | 25 | 20 | 10 |
| 3-1 | 63 | 95 | 100 | 90 | 100 | 95 | 70 | 95 | 70 | 80 | 80 | 100 | 25 | 70 |
|  | 500 | 100 | 100 | 100 | 100 | 100 | 100 | 100 | 100 | 100 | 100 | 100 | 100 | 100 |
| 4-2 | 63 | — | — | — | — | — | — | — | — | — | — | — | — | — |
|  | 500 | 100 | 70 | 20 | 99 | 90 | 75 | 10 | 0 | 0 | 0 | 30 | 5 | 10 |
| 5-1 | 63 | — | — | — | — | — | — | — | — | — | — | — | — | — |
|  | 1000 | 30 | 100 | 10 | 90 | 80 | — | 20 | 30 | 10 | 0 | 40 | 0 | 10 |
| 5-2 | 63 | — | — | — | — | — | — | — | — | — | — | — | — | — |
|  | 1000 | 20 | 70 | 0 | 40 | 40 | — | 10 | 0 | 0 | 0 | 15 | 0 | 10 |
| 5-3 | 63 | — | — | — | — | — | — | — | — | — | — | — | — | — |
|  | 1000 | 0 | 0 | 0 | 0 | 0 | — | 0 | 0 | 0 | 0 | 0 | 0 | 0 |
| 5-5 | 63 | — | — | — | — | — | — | — | — | — | — | — | — | — |
|  | 500 | 0 | 0 | 0 | 0 | 0 | — | 0 | 0 | 0 | 0 | 0 | 0 | 0 |
| 5-6 | 63 | — | — | — | — | — | — | — | — | — | — | — | — | — |
|  | 1000 | 90 | 100 | 40 | 100 | 100 | — | 50 | 95 | 95 | 40 | 80 | 80 | 60 |
| 5-8 | 63 | — | — | — | — | — | — | — | — | — | — | — | — | — |
|  | 1000 | 40 | 100 | 30 | 80 | 60 | — | 10 | 0 | 0 | 0 | 20 | 0 | 0 |
| 5-9 | 63 | — | — | — | — | — | — | — | — | — | — | — | — | — |
|  | 1000 | 50 | 100 | 30 | 90 | 70 | — | 10 | 0 | 0 | 0 | 30 | 5 | 25 |
| 5-10 | 63 | — | — | — | — | — | — | — | — | — | — | — | — | — |
|  | 1000 | 80 | 100 | 30 | 70 | 80 | — | 20 | 80 | 70 | 10 | 15 | 30 | 30 |
| 5-11 | 63 | — | — | — | — | — | — | — | — | — | — | — | — | — |
|  | 1000 | 70 | 100 | 10 | 90 | 90 | — | 10 | 20 | 20 | 0 | 40 | 15 | 25 |
| 5-12 | 63 | 30 | 60 | 10 | 40 | 60 | — | 0 | 0 | 0 | 0 | 50 | 0 | 0 |
|  | 500 | 80 | 95 | 50 | 30 | 75 | — | 50 | 40 | 20 | 40 | 100 | 20 | 70 |
| 6-2 | 63 | 40 | 98 | 0 | 20 | 50 | 10 | 10 | 0 | 0 | 0 | 20 | 5 | 0 |
|  | 500 | 95 | 100 | 10 | 90 | 90 | 30 | 10 | 30 | 20 | 0 | 30 | 5 | 30 |
| 6-3 | 63 | 20 | 0 | — | 20 | 0 | 0 | 0 | 0 | 0 | 0 | 0 | 0 | 0 |
|  | 500 | 80 | 20 | — | 70 | 80 | 0 | 30 | 20 | 30 | 0 | 30 | 0 | 40 |
| 6-4 | 63 | 75 | 90 | 15 | 65 | 85 | 20 | 20 | 0 | 0 | 0 | 20 | 10 | 20 |
|  | 500 | 99 | 100 | 50 | 85 | 100 | 20 | 40 | 60 | 80 | 0 | 60 | 20 | 35 |
| 6-5 | 63 | 40 | 0 | — | 0 | 20 | 0 | 0 | 0 | 0 | 0 | 20 | 0 | 20 |
|  | 500 | 80 | 20 | — | 0 | 80 | 0 | 30 | 0 | 20 | 10 | 30 | 0 | 30 |
| 6-6 | 63 | 70 | 50 | 0 | 60 | 90 | 20 | 10 | 20 | 0 | 0 | 10 | 5 | 20 |
|  | 500 | 95 | 95 | 30 | 95 | 100 | 20 | 40 | 70 | 70 | 10 | 50 | 15 | 40 |
| 6-7 | 63 | 70 | 0 | — | 0 | 50 | 0 | 20 | 0 | 0 | 0 | 0 | 0 | 0 |
|  | 500 | 80 | 70 | — | 50 | 80 | 30 | 30 | 50 | 30 | 10 | 30 | 10 | 50 |
| 6-8 | 63 | — | — | — | — | — | — | — | — | — | — | — | — | — |
|  | 500 | 80 | 98 | 40 | 60 | 95 | 20 | 90 | 10 | 10 | 20 | 60 | 5 | 35 |
| 6-9 | 63 | 0 | 0 | 0 | 0 | 0 | 0 | 0 | 0 | 0 | 0 | 0 | 0 | 0 |
|  | 250 | 0 | 0 | 0 | 0 | 0 | 0 | 0 | 0 | 0 | 0 | 0 | 0 | 0 |
| 6-10 | 63 | 90 | 100 | 30 | 100 | 90 | 30 | 30 | 30 | 0 | 50 | 70 | 10 | 10 |
|  | 500 | 100 | 100 | 100 | 100 | 100 | 100 | 100 | 100 | 100 | 100 | 100 | 80 | 90 |
| 6-14 | 63 | 20 | 70 | — | 50 | 70 | 0 | 0 | 0 | 30 | 0 | 50 | 0 | 20 |
|  | 500 | 100 | 100 | — | 100 | 95 | 50 | 70 | 60 | 90 | 30 | 90 | 20 | 50 |
| 6-15 | 63 | 20 | 60 | 20 | 20 | 50 | 0 | 0 | 0 | 0 | 0 | 0 | 0 | 0 |
|  | 500 | 95 | 99 | 40 | 70 | 90 | 20 | 40 | 0 | 10 | 0 | 40 | 5 | 5 |
| 6-16 | 63 | 70 | 100 | 0 | 95 | 80 | 15 | 20 | 0 | 0 | 0 | 40 | 10 | 30 |
|  | 500 | 100 | 100 | 30 | 95 | 100 | 20 | 50 | 30 | 20 | 0 | 60 | 20 | 40 |
| 6-17 | 63 | 0 | 0 | 0 | 0 | 0 | 0 | 0 | 0 | 0 | 0 | 0 | 0 | 0 |
|  | 500 | 0 | 0 | 0 | 0 | 0 | 0 | 0 | 0 | 0 | 0 | 0 | 0 | 0 |
| 7-1 | 63 | 100 | 90 | 70 | 100 | 100 | 95 | 20 | 0 | — | 30 | 20 | 20 | 0 |
|  | 500 | 100 | 100 | 20 | 100 | 100 | 100 | 60 | 20 | 30 | 60 | 80 | 35 | 50 |
| 7-2 | 63 | 100 | 100 | 100 | 100 | 100 | 100 | 90 | 40 | 60 | 30 | 95 | 35 | 80 |
|  | 500 | 100 | 100 | 100 | 100 | 100 | 100 | 100 | 95 | 100 | 85 | 100 | 90 | 95 |
| 8-1 | 63 | — | — | — | — | — | — | — | — | — | — | — | — | — |
|  | 500 | 40 | 90 | 30 | 70 | 85 | — | 10 | 0 | 0 | 0 | 50 | 0 | 0 |
| 8-2 | 63 | 60 | 60 | 20 | 70 | 80 | 30 | 10 | 10 | 0 | 0 | 40 | 5 | 0 |
|  | 500 | 100 | 100 | 50 | 100 | 100 | 95 | 30 | 50 | 20 | 20 | 90 | 15 | 70 |
| 8-3 | 63 | 20 | 10 | 0 | 60 | 50 | 20 | 0 | 0 | 0 | 0 | 10 | 0 | 0 |
|  | 500 | 75 | 75 | 0 | 90 | 85 | 60 | 0 | 0 | 0 | 0 | 50 | 50 | 0 |
| 8-4 | 63 | 60 | 70 | 20 | 50 | 70 | 0 | 10 | 0 | — | 0 | 20 | 5 | 0 |
|  | 500 | 100 | 85 | 40 | 60 | 75 | 0 | 10 | 0 | 0 | 0 | 30 | 10 | 0 |
| 8-5 | 63 | 100 | 100 | 55 | 90 | 100 | 55 | 30 | 20 | 10 | 0 | 50 | 5 | 0 |
|  | 500 | 100 | 100 | 100 | 100 | 100 | 100 | 65 | 55 | 60 | 70 | 85 | 20 | 10 |
| 8-6 | 63 | 100 | 100 | 60 | 90 | 90 | 60 | 30 | 10 | 0 | 0 | 70 | 5 | 5 |
|  | 500 | 100 | 100 | 100 | 100 | 99 | 90 | 90 | 30 | 30 | 30 | 90 | 20 | 50 |
| 8-7 | 63 | 100 | 100 | — | 100 | 90 | 60 | 0 | 0 | 0 | 0 | 20 | 20 | 10 |
|  | 500 | 100 | 100 | — | 100 | 100 | 80 | 0 | 20 | 70 | 50 | 70 | 0 | 50 |

TABLE 14-continued

Post-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 8-8 | 63 | 95 | 95 | 40 | 90 | 99 | 30 | 20 | 10 | 10 | 0 | 25 | 10 | 0 |
|  | 500 | 100 | 100 | 40 | 50 | 100 | 40 | 30 | 0 | 0 | 0 | 75 | 10 | 10 |
| 8-9 | 63 | 90 | 50 | 0 | 40 | 60 | 30 | 0 | 0 | 0 | 0 | 20 | 0 | 0 |
|  | 500 | 100 | 100 | 100 | 100 | 95 | 80 | 30 | 0 | 30 | 10 | 70 | 10 | 0 |
| 8-11 | 63 | 100 | 100 | — | 100 | 100 | 100 | 30 | 100 | 90 | 50 | 90 | 20 | 40 |
|  | 500 | 100 | 100 | — | 100 | 100 | 100 | 60 | 100 | 99 | 90 | 100 | 95 | 50 |
| 8-12 | 63 | 70 | 100 | — | 80 | 80 | 50 | 0 | 0 | 0 | 0 | 50 | 0 | 0 |
|  | 500 | 100 | 100 | — | 70 | 70 | 70 | 30 | 40 | 50 | 0 | 60 | 0 | 30 |
| 8-14 | 63 | 70 | 95 | 40 | 80 | 80 | 40 | 30 | 0 | 0 | 0 | 30 | 5 | 0 |
|  | 500 | 90 | 95 | 30 | 85 | 90 | 60 | 20 | 0 | 0 | 0 | 30 | 5 | 0 |
| 8-15 | 63 | 40 | 50 | 0 | 40 | 70 | 30 | 0 | 0 | 0 | 0 | 20 | 0 | 0 |
|  | 500 | 70 | 80 | 50 | 80 | 90 | 70 | 0 | 0 | 0 | 0 | 50 | 0 | 0 |
| 8-16 | 63 | 90 | 80 | 0 | 90 | 85 | 40 | 10 | 0 | 0 | 0 | 10 | 0 | 0 |
|  | 500 | 100 | 100 | 70 | 75 | 95 | 40 | 30 | 0 | 10 | 0 | 20 | 5 | 0 |
| 8-17 | 63 | 100 | 100 | — | 100 | 99 | 60 | 50 | 90 | 50 | 30 | 90 | 20 | 40 |
|  | 500 | 100 | 100 | — | 100 | 100 | 100 | 90 | 100 | 100 | 90 | 100 | 10 | 90 |
| 8-18 | 63 | 100 | 100 | 70 | 100 | 100 | 95 | 40 | 70 | 50 | 0 | 80 | 15 | 60 |
|  | 5400 | 100 | 100 | 100 | 100 | 100 | 60 | 70 | 70 | 90 | 10 | 70 | 20 | 40 |
| 8-19 | 63 | 100 | 100 | 70 | 100 | 100 | 90 | 60 | 50 | 50 | 30 | 65 | 30 | 40 |
|  | 500 | 100 | 100 | 90 | 100 | 100 | 90 | 90 | 50 | 50 | 30 | 80 | 30 | 60 |
| 8-20 | 63 | 100 | 100 | 90 | 100 | 95 | 90 | 70 | 20 | 90 | 30 | 90 | 15 | 15 |
|  | 500 | 100 | 100 | 100 | 100 | 100 | 100 | 95 | 40 | 100 | 30 | 100 | 20 | 60 |
| 8-21 | 63 | 100 | 100 | — | 90 | 99 | 60 | 0 | 0 | 10 | 0 | 90 | 10 | 50 |
|  | 500 | 100 | 100 | — | 100 | 100 | 90 | 40 | 70 | 70 | 60 | 100 | 0 | 60 |
| 8-22 | 63 | 95 | 100 | 50 | 80 | 100 | 80 | 20 | 70 | 0 | 0 | 65 | 5 | 5 |
|  | 500 | 100 | 100 | 80 | 100 | 100 | 100 | 75 | 30 | 30 | 30 | 95 | 15 | 10 |
| 8-23 | 63 | 95 | 100 | 70 | 50 | 95 | 50 | 0 | 0 | 0 | 0 | 25 | 0 | 0 |
|  | 500 | 99 | 100 | 100 | 100 | 99 | 100 | 20 | 0 | 20 | 0 | 60 | 5 | 0 |
| 8-24 | 63 | 100 | 95 | — | 70 | 50 | 0 | 0 | 10 | 0 | 50 | 0 | 10 | 20 |
|  | 500 | 100 | 100 | — | 80 | 80 | 50 | 20 | 0 | 50 | 20 | 40 | 10 | 30 |
| 8-25 | 63 | 100 | 100 | 70 | 100 | 90 | 90 | 70 | 20 | 40 | 10 | 70 | 10 | 10 |
|  | 500 | 100 | 100 | 100 | 100 | 100 | 90 | 95 | 65 | 60 | 40 | 90 | 25 | 60 |
| 8-26 | 63 | — | — | — | — | — | — | — | — | — | — | — | — | — |
|  | 500 | 0 | 0 | 0 | 0 | 0 | 0 | 0 | 0 | 0 | 0 | 0 | 0 | 0 |
| 8-27 | 63 | 90 | 80 | 30 | 50 | 90 | 60 | 50 | 0 | 30 | 10 | 70 | 5 | 0 |
|  | 500 | 100 | 100 | 100 | 80 | 100 | 85 | 50 | 10 | 20 | 20 | 80 | 10 | 5 |
| 8-28 | 63 | 100 | 100 | 50 | 90 | 90 | 50 | 30 | 10 | 40 | 20 | 50 | 10 | 10 |
|  | 500 | 100 | 100 | 100 | 95 | 100 | 90 | 90 | 80 | 60 | 30 | 90 | 20 | 40 |
| 8-29 | 63 | 100 | 100 | 100 | 100 | 100 | 90 | 90 | 80 | 90 | 50 | 90 | 40 | 60 |
|  | 500 | 100 | 100 | 100 | 100 | 100 | 100 | 100 | 100 | 100 | 100 | 100 | 70 | 100 |
| 8-30 | 63 | 90 | 100 | 100 | 100 | 95 | 90 | 60 | 10 | 20 | 0 | 95 | 15 | 5 |
|  | 500 | 100 | 100 | 100 | 100 | 100 | 99 | 95 | 40 | 95 | 10 | 100 | 40 | 80 |
| 8-31 | 63 | 70 | 70 | 0 | 80 | 90 | 50 | 10 | 0 | 0 | 0 | 70 | 5 | 0 |
|  | 500 | 100 | 100 | 80 | 80 | 80 | 95 | 40 | 20 | 30 | 50 | 70 | 10 | 5 |
| 8-32 | 63 | 90 | 100 | 10 | 100 | 95 | 50 | 10 | 0 | 0 | 0 | 30 | 5 | 0 |
|  | 500 | 100 | 100 | 100 | 100 | 100 | 90 | 40 | 10 | 20 | 0 | 80 | 5 | 10 |
| 8-33 | 63 | 95 | 100 | 55 | 90 | 90 | 60 | 20 | 20 | 10 | 0 | 55 | 5 | 0 |
|  | 500 | 100 | 100 | 95 | 100 | 100 | 100 | 80 | 40 | 30 | 50 | 70 | 15 | 10 |
| 8-34 | 63 | 50 | 95 | 30 | 100 | 95 | 50 | 20 | 10 | 0 | 0 | 50 | 5 | 0 |
|  | 500 | 100 | 100 | 100 | 100 | 100 | 95 | 65 | 0 | 50 | 40 | 90 | 15 | 40 |
| 8-35 | 63 | 95 | 100 | — | 40 | 80 | 10 | 40 | 0 | 40 | 0 | 20 | 10 | 20 |
|  | 500 | 100 | 100 | — | 95 | 99 | 10 | 60 | 80 | 80 | 10 | 90 | 10 | 50 |
| 8-36 | 63 | 100 | 100 | — | 100 | 95 | 20 | 0 | 50 | 30 | 30 | 30 | 10 | 40 |
|  | 250 | 100 | 100 | — | 95 | 99 | 20 | 30 | 40 | 90 | 60 | 90 | 10 | 30 |
| 8-37 | 63 | 90 | 100 | 100 | 95 | 90 | 30 | 0 | 0 | 0 | 0 | 90 | 0 | 0 |
|  | 500 | 95 | 100 | 95 | 80 | 90 | 60 | 30 | 10 | 50 | 0 | 100 | 40 | 35 |
| 8-38 | 63 | 60 | 100 | 30 | 40 | 40 | 20 | 0 | 0 | 0 | 0 | 10 | 0 | 20 |
|  | 250 | 70 | 100 | 30 | 40 | 50 | 50 | 20 | 0 | 0 | 0 | 20 | 20 | 50 |
| 8-39 | 63 | 70 | 100 | 100 | 100 | 50 | 60 | 10 | 0 | 0 | 0 | 60 | 15 | 15 |
|  | 250 | 80 | 100 | 30 | 90 | 70 | 80 | 10 | 30 | 10 | 10 | 80 | 10 | 15 |
| 8-40 | 63 | 80 | 100 | 30 | 40 | 60 | 80 | 0 | 0 | 0 | 0 | 80 | 0 | 0 |
|  | 250 | 90 | 100 | 75 | 100 | 80 | 20 | 10 | 0 | 0 | 0 | 60 | 10 | 0 |
| 8-41 | 63 | 40 | 95 | 30 | 30 | 40 | 90 | 0 | 0 | 0 | 0 | 30 | 0 | 0 |
|  | 250 | 40 | 100 | 100 | 100 | 50 | 30 | 0 | 0 | 0 | 0 | 60 | 0 | 0 |
| 8-42 | 63 | 50 | 100 | 0 | 60 | 50 | 40 | 0 | 0 | 0 | 0 | 20 | 0 | 0 |
|  | 250 | 95 | 100 | 0 | 70 | 80 | 90 | 0 | 0 | 0 | 0 | 60 | 0 | 0 |
| 8-43 | 63 | 60 | 100 | 95 | 100 | 90 | 100 | 40 | 20 | 20 | 0 | 80 | 20 | 10 |
|  | 250 | 90 | 100 | 100 | 100 | 100 | 100 | 60 | 30 | 30 | 20 | 100 | 30 | 30 |
| 9-1 | 63 | 100 | 100 | 30 | 100 | 95 |  | 20 | 30 | 70 | 20 | 90 | 10 | 20 |
|  | 500 | 100 | 100 | 30 | 100 | 100 |  | 90 | 100 | 99 | 50 | 100 | 70 | 80 |
| 9-2 | 63 | 100 | 100 | 30 | 100 | 100 |  | 10 | 10 | 10 | 0 | 40 | 5 | 15 |
|  | 500 | 100 | 100 | 95 | 80 | 95 |  | 60 | 80 | 70 | 30 | 80 | 60 | 30 |
| 9-3 | 63 | 100 | 100 | 20 | 100 | 95 |  | 20 | 0 | 10 | 30 | 80 | 10 | 20 |
|  | 500 | 100 | 100 | 95 | 100 | 100 |  | 95 | 90 | 90 | 95 | 100 | 80 | 90 |

TABLE 14-continued

Post-emerge Herbicide Activity

| Compound No. | Rate g ai/ha | AMARE | ABUTH | CASOB | IPOHE | CHEAL | AMBEL | SETVI | ECHCG | SORHA | DIGSA | SOY | CORN | RICE |
|---|---|---|---|---|---|---|---|---|---|---|---|---|---|---|
| 9-4 | 63 | 95 | 100 | 90 | 100 | 80 | | 30 | 70 | 70 | 10 | 95 | 40 | 80 |
|  | 500 | 100 | 100 | 100 | 90 | 100 | | 95 | 100 | 98 | 95 | 100 | 80 | 70 |
| 9-5 | 63 | 100 | 90 | 40 | 100 | 90 | | 30 | 20 | 50 | 0 | 50 | 10 | 50 |
|  | 500 | 100 | 100 | 100 | 90 | 100 | | 90 | 100 | 100 | 80 | 95 | 70 | 80 |
| 9-6 | 63 | 100 | 100 | 40 | 100 | 100 | | 20 | 90 | 100 | 90 | 80 | 40 | 30 |
|  | 500 | 100 | 100 | 100 | 100 | 100 | | 100 | 100 | 100 | 100 | 100 | 75 | 70 |
| 9-7 | 63 | 100 | 100 | 90 | 100 | 100 | | 40 | 60 | 80 | 10 | 80 | 30 | 20 |
|  | 500 | 100 | 100 | 90 | 100 | 100 | | 70 | 70 | 90 | 30 | 90 | 80 | 80 |
| 9-8 | 63 | 100 | 100 | 30 | 95 | 95 | | 30 | 10 | 30 | 10 | 50 | 15 | 30 |
|  | 500 | 100 | 100 | 30 | 100 | 100 | | 75 | 95 | 90 | 30 | 75 | 80 | 80 |
| 9-9 | 63 | 100 | 100 | 90 | 90 | 90 | | 20 | 10 | 40 | 10 | 95 | 30 | 70 |
|  | 500 | 100 | 100 | 100 | 100 | 100 | | 90 | 100 | 100 | 90 | 100 | 95 | 98 |
| 9-10 | 63 | 100 | 100 | 40 | 100 | 100 | | 20 | 20 | 60 | 10 | 100 | 25 | 50 |
|  | 500 | 80 | 100 | 50 | 100 | 100 | | 70 | 95 | 95 | 20 | 80 | 90 | 70 |
| 9-11 | 63 | 100 | 100 | 30 | 100 | 80 | | 20 | 0 | 20 | 40 | 95 | 15 | 20 |
|  | 500 | 100 | 100 | 80 | 100 | 100 | | 40 | 50 | 80 | 80 | 100 | 40 | 50 |
| 9-14 | 63 | 100 | 100 | 60 | 95 | 80 | | 80 | 10 | 40 | 30 | 90 | 20 | 15 |
|  | 500 | 100 | 100 | 100 | 100 | 100 | | 100 | 100 | 100 | 100 | 95 | 98 | 90 |
| 9-15 | 125 | 100 | 100 | 100 | 100 | 100 | | 95 | 90 | 95 | 90 | 100 | 70 | 90 |
|  | 500 | 100 | 100 | 100 | 100 | 100 | | 100 | 99 | 100 | 100 | 100 | 90 | 95 |
| 9-16 | 63 | 100 | 100 | 100 | 100 | 100 | | 100 | 100 | 100 | 100 | 100 | 100 | 100 |
|  | 500 | 100 | 100 | 100 | 100 | 100 | | 100 | 100 | 100 | 100 | 100 | 100 | 100 |
| 9-17 | 63 | 95 | 100 | 0 | 100 | 80 | | 10 | 0 | 0 | 10 | 100 | 10 | 15 |
|  | 500 | 95 | 100 | 0 | 95 | 90 | | 10 | 60 | 80 | 10 | 100 | 60 | 70 |
| 9-21 | 63 | 100 | 100 | 100 | 100 | 100 | | 90 | 70 | 60 | 30 | 99 | 25 | 60 |
|  | 500 | 100 | 100 | 100 | 100 | 100 | | 100 | 100 | 90 | 90 | 100 | 60 | 80 |
| 9-22 | 63 | 100 | 100 | 30 | 100 | 90 | | 10 | 20 | 0 | 10 | 80 | 5 | 0 |
|  | 500 | 100 | 100 | 70 | 100 | 100 | | 80 | 90 | 80 | 50 | 80 | 30 | 40 |
| 9-23 | 63 | 85 | 45 | 10 | 50 | 70 | | 0 | 0 | 0 | 0 | 10 | 0 | 0 |
|  | 500 | 95 | 90 | 30 | 75 | 95 | | 10 | 50 | 30 | 0 | 50 | 15 | 20 |
| 9-24 | 63 | 100 | 100 | 30 | 100 | 100 | | 70 | 30 | 30 | 40 | 70 | 20 | 10 |
|  | 500 | 100 | 100 | 80 | 100 | 100 | | 95 | 90 | 70 | 75 | 90 | 30 | 50 |
| 9-25 | 63 | 100 | 95 | 50 | 100 | 100 | | 30 | 10 | 10 | 0 | 60 | 15 | 5 |
|  | 500 | 100 | 100 | 100 | 100 | 100 | | 80 | 90 | 70 | 60 | 80 | 35 | 35 |
| 9-26 | 63 | 100 | 100 | 100 | 100 | 100 | | 100 | 80 | 90 | 80 | 100 | 40 | 40 |
|  | 500 | 100 | 100 | 100 | 100 | 100 | | 100 | 100 | 100 | 80 | 100 | 70 | 60 |
| 9-28 | 63 | 90 | 90 | 10 | 95 | 80 | | 25 | 0 | 0 | 0 | 40 | 5 | 5 |
|  | 500 | 100 | 100 | 50 | 100 | 100 | | 50 | 10 | 30 | 0 | 80 | 40 | 15 |

The compositions of the present invention may be used in admixture with or in combination with other agricultural chemicals, fertilizers or phytotoxicity-reducing agents. In such a case, they may exhibit even better effects or activities. As other agricultural chemicals, herbicides, fungicides, antibiotics, plant hormones, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha. The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

1. Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin or quinclorac.

2. Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetryn, ametryn, prometryn or dimethametryn, a uracil type such as bromacil, terbacil or lenacil, an anilide type such as propanil or cypromid, a carbamate type such as swep desmedipham or phenmedipham, a hydroxybenzonitrile type such as bromoxynil or ioxynil, and others such as pyridate, bentazon and methazole.

3. A quaternary ammonium salt type such as paraquat, diquat or difenzoquat, which is believed to be converted to free radicals by itself to form active oxygen in the plant and thus to exhibit quick herbicidal effects.

4. Those which are believed to exhibit herbicidal effects by inhibiting chlorophyll biosynthesis in plants and abnormally accumulating a photsensitizing peroxide substance in the plant body, including a diphenyl ether type such as nitrofen, lactofen, acifluorfen-sodium, oxyfluorfen, fomesafen, bifenox, or chlomethoxyfen, a cyclic amide type such as chlorphthalim, flumioxadine or flumicloracpentyl, and others such as oxadiazon, sulfentrazone or thidiazimin.

5. Those which are believed to exhibit herbicidal effects characterized by whitening activities by inhibiting chromogenesis of plants such as carotenoids including a pyridazinone type such as norflurazon, chioridazon or metflurazon, a pyrazol type such as pyrazolate, pyrazoxyfen or benzofenap, and others such as fluridone, fluramone, diflufencam, methoxyphenone, clomazone, amitrole, sulcotrione or isoxaflutole.

6. Those which exhibit herbicidal effects specifically to gramineous plants including an aryloxyphenoxypropionic acid type such as diclofop-methyl, pyrofenop-sodium, fluazifop-butyl, haloxyfop-methyl, quizalofop-ethyl, fenoxaprop ethyl, or cyhalofop-butyl and a cyclohexanedione type such as alloxydim-sodium, sethoxydim, clethodim or tralkoxydim.

7. Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron-methyl, thifensulfuron-methyl, rimsulfuron, azimsulfuron, flazasulfuron, imazosulfuron, cyclosulfamuron, flupyrsulfuron, a triazolopyrimidine-sulfonamide type such as flumetsulam or metosulam, an imidazolinone type such as imazapyr, imazethapyr, imazaquin, imazamox, imazameth, imazamethabenz methyl, a pyrimidinesalicylic acid type such as pyrthiobac-sodium, bispyribac-sodium or pyriminobac-metbyl, and others such as glyphosate, glyphosate-ammonium, glyphosate-isopropylamine or sulfosate.

8. Those which are believed to exhibit herbicidal effects by interfering with the normal metabolism of inorganic nitrogen assimilation such as glufosinate, glufosinate-ammonium, phosphinothricin or bialophos.

9. Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbamate type such as propham, chlorpropham, barban, and asulam, an organophosphorous type such as amiprofos-methyl or butamifos and others such as DCPA and dithiopyr.

10. Those which are believed to exhibit herbicidal effects by inhibiting protein sysnthesis of plant cells, including a acetanilide type such as alachlor, metolachor, propachlor, acetochlor (including combinations with herbicide safeners) and dimethenamid.

11. Those in which the mode of action causing the herbicidal effects are not well understood including the dithiocarbamates such as thiobencarb, EPTC, diallate, triallate, molinate, pebulate, cycloate, butylate, vernolate or pro-sulfocarb and miscellaneous herbicides such as MSMA, DSMA, endothall, ethofumesate, sodium chlorate, pelargonic acid and fosamine.

Examples of combinations with Other Herbicides (Note: Weed species abbreviations are from the *Composite List of Weeds* published by the Weed Science Society of America, 1989.)

The following examples illustrate the utility of combinations of compounds of this invention and existing herbicides. The methods used are identical to those for the application of single compounds except the commercial formulations of existing herbicides were added to the spray mixture in the appropriate amounts before spraying.

Combination Example 1. Pre-emergent application of Compound 9-1 with metolachlor

| | | Percent Control of Broadleaf Weeds | | | | | |
|---|---|---|---|---|---|---|---|
| Treatment | Rate (g ai/ha) | AMARE | ABUTH | CASOB | IPOHE | CHEAL | AMBEL |
| Comp. 9-1 | 62.5 | 100 | 95 | 10 | 50 | 100 | 40 |
| Metolachlor | 1121 | 100 | 20 | 10 | 20 | 90 | 30 |
| Comp. 9-1 + Metolachlor | 62.5 + 1121 | 100 | 100 | 100 | 70 | 100 | 80 |

| | | Percent Control of Grass Weeds | | | |
|---|---|---|---|---|---|
| Treatment | Rate (g ai/ha) | SETVI | ECHCG | SORHA | DIGSA |
| Comp. 9-1 | 62.5 | 90 | 0 | 0 | 20 |
| Metolachlor | 1121 | 100 | 100 | 100 | 100 |
| Comp. 9-1 + Metolachlor | 62.5 + 1121 | 100 | 100 | 100 | 100 |

Combination Example 2. Pre-emergent application of Compound 9-1 with dimethenamid

| | | Percent Control of Broadleaf Weeds | | | | | |
|---|---|---|---|---|---|---|---|
| Treatment | Rate (g ai/ha) | AMARE | ABUTH | CASOB | IPOHE | CHEAL | AMBEL |
| Comp. 9-1 | 62.5 | 100 | 95 | 10 | 50 | 100 | 40 |
| Dimethenamid | 520 | 100 | 40 | 40 | 0 | 30 | 40 |
| Comp. 9-1 + Dimethenamid | 62.5 + 520 | 100 | 100 | 70 | 100 | 100 | 100 |

| | | Percent Control of Grass Weeds | | | |
|---|---|---|---|---|---|
| Treatment | Rate (g ai/ha) | SETVI | ECHCG | SORHA | DIGSA |
| Comp. 9-1 | 62.5 | 90 | 0 | 0 | 20 |
| Dimethenamid | 1121 | 100 | 100 | 100 | 100 |
| Comp. 9-1 + Dimethenamid | 62.5 + 1121 | 100 | 100 | 100 | 100 |

Combination Example 3. Post-emergent application of Compound 9-1 with nicosulfuron

| | | Percent Control of Broadleaf Weeds | | | | | |
|---|---|---|---|---|---|---|---|
| Treatment | Rate (g ai/ha) | AMARE | ABUTH | CASOB | IPOHE | CHEAL | AMBEL |
| Comp. 9-1 | 31.25 | 60 | 60 | 0 | 80 | 90 | 40 |
| Nicosulfuron | 23 | 70 | 55 | 30 | 70 | 70 | 0 |
| Comp. 9-1 + Nicosulfuron | 62.5 + 23 | 95 | 80 | 10 | 85 | 95 | 40 |

| | | Percent Control of Grass Weeds | | | |
|---|---|---|---|---|---|
| Treatment | Rate (g ai/ha) | SETVI | ECHCG | SORHA | DIGSA |
| Comp. 9-1 | 31.25 | 10 | 0 | 10 | 10 |
| Nicosulfuron | 23 | 85 | 95 | 85 | 80 |
| Comp. 9-1 + Nicosulfuron | 31.25 + 23 | 90 | 90 | 95 | 60 |

Combination Example 4. Postemergent application of Compound 9-1 with pyridate

| | | Percent Control of Broadleaf Weeds | | | | | |
|---|---|---|---|---|---|---|---|
| Treatment | Rate (g ai/ha) | AMARE | ABUTH | CASOB | IPOHE | CHEAL | AMBEL |
| Comp. 9-1 | 31.25 | 60 | 60 | 0 | 80 | 90 | 40 |
| Pyridate | 527 | 90 | 60 | 10 | 80 | 85 | 40 |
| Comp. 9-1 + Pyridate | 31.25 + 527 | 95 | 100 | 40 | 100 | 90 | 85 |

| | | Percent Control of Grass Weeds | | | |
|---|---|---|---|---|---|
| Treatment | Rate (g ai/ha) | SETVI | ECHCG | SORHA | DIGSA |
| Comp. 9-1 | 31.25 | 10 | 0 | 10 | 10 |
| Pyridate | 527 | 95 | 50 | 10 | 10 |
| Comp. 9-1 + Pyridate | 31.25 + 527 | 85 | 60 | 30 | 60 |

Those compounds also may show utility as chemical desiccants to be used as harvest aids for crops such as cotton and potatoes. Preliminary studies are conducted in a greenhouse in which potato plant foliage was sprayed with solutions containing different compounds described in this invention. Greater than 90% necrosis of leaf tissue was observed within 1 week after application, when 100 g to 1000 g ai/ha were included in the treatment. Likewise, when cotton plants were treated, 100% necrosis of leaf tissue was observed within 48 hours after treatment.

What is claimed is:

1. A compound represented by the formula (1) or its salts:

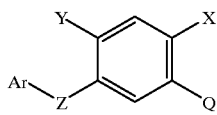
(I)

wherein X is hydrogen, halogen, cyano, nitro, or $(C_{1-6})$ haloalkyl;

Y is halogen, nitro or $(C_{1-6})$haloalkyl;

Z is oxygen or sulfur;

Q is

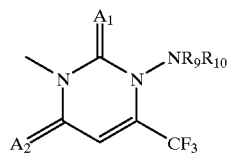

$A_1$ and $A_2$ are independently oxygen or sulfur;

$R_9$ and $R_{10}$ are hydrogen, $(C_{1-6})$alkyl, acyl, or $(C_{1-6})$ alkylsulfonyl or $R_9$ and $R_{10}$ may form a ring consisting of polymethylene, $(CH_2)m$ groups, where m is an integer of 2, 3, 4, or 5, together with the nitrogen atom of $NR_9R_{10}$, which may or may not have a $(C_{1-6})$alkyl substituent; and Ar is a substituted or unsubstituted aryl or heteroaryl ring.

2. The compound or its salt according to claim 1, wherein

X is hydrogen or halogen, and

Y is halogen, and

Z is oxygen or sulfur, and

Ar is pyridyl, pyrimidyl, pyridazinyl, triazolyl, thiazolyl, isothiazolyl, or phenyl, or pyridyl, pyrimidyl, triazolyl, thiazolyl, isothiazolyl , or phenyl substituted with up to five substituents independently selected from halogen, $(C_{1-6})$alkyl, halo$(C_{1-6})$alkyl, $(C_{1-6})$alkoxy, $(C_{1-6})$ alkylthio, halo$(C_{1-6})$alkoxy, $(C_{1-6})$alkylsulfonyl, $(C_{1-6})$ alkylsulfinyl, di$(C_{1-6})$alkylaminocarbonyl, cyano, nitro, amino, hydroxy, $(C_{1-6})$alkylsulfonylamino, $(C_{1-6})$alkoxycarbonyl$(C_{1-6})$alkoxy, $(C_{1-6})$ alkxylcarbonylamino, bisbenzoylamino, aminoacetyl, aminotrifluoroacetyl, or amino$(C_{1-6})$alkylsulfonate.

3. The compound or its salt according to claim 1, wherein

X is fluorine, and

Y is chlorine, and

Ar is 2-pyridyl, 3-pyridyl , 4-pyridyl , 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 5-amino-2-pyridyl, 3-dimethylaminocarbonyl-2-pyridyl, 3-methylsulfonyl-2-pyridyl, 3-isopropylsulfonyl-2-pyridyl, 6-chloro-3-trifluoromethyl-2-pyridyl, 3,5,6-trifluoropyridyl, 2-pyrimidyl, 4-pyrimidyl, 5-bromo-2-pyrimidyl, 4-chloro-2-pyrimidyl, 4-trifluoromethyl-2-pyrimidyl, 4,6-dimethoxy-2-pyrimidyl, 4,6-dimethoxy-2-pyrimidyl, 2,6-dimethoxy-4-pyrimidyl, 4,6-dimethoxy-2-triazinyl, phenyl, 2-iodophenyl, 2-trifluoromethoxyphenyl, 2-nitrophenyl, 4-nitrophenyl, 4-aminophenyl, 4-hydroxyphenyl, 4-methylsulfonylaminophenyl, 4-(1-ethoxycarbonylethoxy)phenyl, 2-cyanophenyl, 2-cyano-3-fluorophenyl, 2-cyano-4-fluorophenyl, 2-amino-4-(1-ethoxycarbonylethoxy)-phenyl, 2-cyano-4-nitrophenyl, 4-amino-2-cyanophenyl, 4-nitro-2-trifluoromethylphenyl, 4-amino-2-trifluoromethylphenyl, 4-acetylamino-2-trifluoromethylphenyl 4-(1-ethoxycarbonylethoxy)-2-nitrophenyl, 5-chloro-4-(1-ethoxycarbonylethoxy)-2-nitrophenyl, 3-methyl-4-nitro-5-isothiazolyl, or 5-nitro-2-thiazolyl.

4. The compound or its salt according to claim 1 wherein Ar is 2-pyridyl, 3-pyridyl, 4-pyridyl, 2-pyrimidyl, 4-pyrimidyl, phenyl, 2-nitrophenyl, 4-nitrophenyl, or 2-cyanophenyl.

5. The compound or its salt according to claim 1 wherein Ar is 2-pyridyl, 3-pyridyl, 4-pyridyl , 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 5-amino-2-pyridyl, 3-dimethylaminocarbonyl-2-pyridyl, 3-methylsulfonyl-2-pyridyl, 3-isopropylsulfonyl-2-pyridyl, 6-chloro-3-trifluoromethyl-2-pyridyl, 3,5,6-trifluoropyridyl, 2-pyrimidyl, 4-pyrimidyl, 5-bromo-2-pyrimidyl, 4-chloro-2-pyrimidyl, 4-trifluoromethyl-2-pyrimidyl, 4,6-dimethoxy-2-pyrimidyl, 2,6-dimethoxy-4-pyrimidyl, 4,6-dimethoxy-2-triazinyl, phenyl, 2-iodophenyl, 2-trifluoromethoxyphenyl, 2-nitrophenyl, 4-nitrophenyl, 4-aminophenyl, 4-hydroxyphenyl, 4-methylsulfonylaminophenyl, 4-(1-ethoxycarbonylethoxy)phenyl, 2-cyanophenyl, 2-cyano-3-fluorophenyl, 2-cyano-4-fluorophenyl, 2-amino-4-(1-ethoxycarbonylethoxy)-phenyl, 2-cyano-4-nitrophenyl, 4-amino-2-cyanophenyl, 4-nitro-2-trifluoromethylphenyl, 4-amino-2-trifluoromethylphenyl, 4-acetylamino-2-trifluoromethylphenyl, 4-(1-ethoxycarbonylethoxy)-2-nitrophenyl, 5-chloro-4-(1-ethoxycarbonylethoxy)-2-nitrophenyl, 3-methyl-4-nitro-5-isothiazolyl, or 5-nitro-2-thiazolyl.

6. A process for producing a compound represented by the formula (I) in claim 1 or its salt, said process comprising reacting a compound represented by the formula:

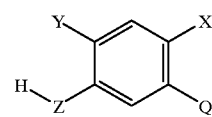

with a compound of the formula: Ar-Hal wherein Hal is a halogen atom, in the presence of a base.

7. A process for producing a compound or its salt represented by the formula (I) in claim 1 and having the formula (XXXIII)

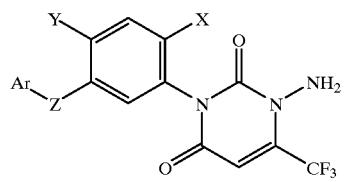

XXXIII wherein said process comprising reacting the isocyanate of formula (III):

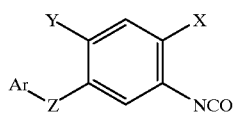

III with the hydrazono-ester (XLIII) of the formula:

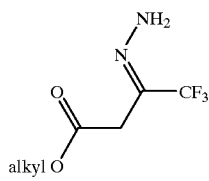

XLIII wherein alkyl is an alkyl group.

8. A process for producing a compound or its salt represented by the formula (I) in claim 1 and having the formula (XXXIII):

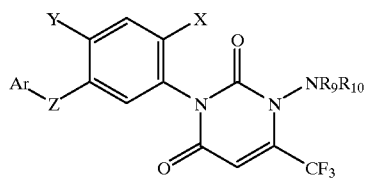

(XXXIII)

said process comprising reacting a compound represented by formula (III):

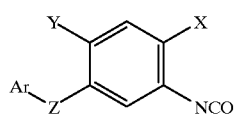

(III)

with alkyl 3-amino-4,4,4-trifluorocrotonate in the presence of a base and quenching the reaction with an animating agent.

9. A process for producing a compound or its salt represented by the formula (XXXV)

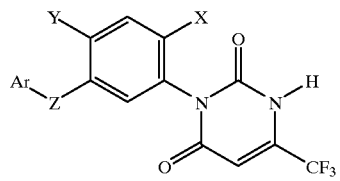

XXXV said process comprising reacting a haloaryl uracil of formula (XXXVIII):

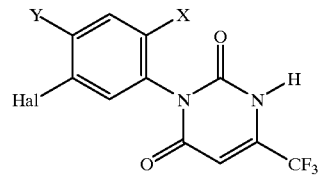

XXXVIII with the salt of an Ar—Z—H;

wherein X is hydrogen, halogen, cyano, nitro, or $C_{1-6}$ haloalkyl; Y is halogen, nitro or $C_{1-6}$ haloalky; Ar is a substituted or unsubstituted aryl or heteroaryl ring; Hal is a halogen atom and Z is oxygen or sulfur.

10. A herbicidal composition, characterized in that it contains at least one compound or its salt according to claim 1.

11. A herbicidal composition which comprises an effective amount of a compound or its salt of claim 1 and an agricultural adjuvant.

12. A method for controlling weeds, which comprises applying to the locus to be protected a herbicidally effective amount of a compound or its salt of claim 1.

13. A method for controlling weeds in a corn field which comprises applying a herbicidally effective amount of a compound or its salt of claim 1 to the corn field.

14. A method for controlling weeds in a soybean field which comprises applying a herbicidally effective amount of a compound or its salt of claim 1 to the soybean field.

15. A method for controlling weeds, which comprises applying to the locus to be protected a herbicidally effective amount of a compound or its salt of claim 1 in combination with another herbicide for providing an additive or synergistic herbicidal effect.

16. A method for controlling weeds of claim 15 wherein the another herbicide is an acetanilide or sulfonylurea.

17. A method to desiccate a plant which comprises applying to the plant a compound or its salt of claim 1.

18. A method to desiccate a plant of claim 17 wherein the plant to which the compound or its salt is applied is a potato plant or a cotton plant.

19. A method for controlling weeds as in claim 12 wherein the compound or its salt is applied to the soil as a preemergent herbicide.

20. A method for controlling weeds as in claim 12 wherein the compound or its salt is applied to plant foliage.

* * * * *